(12) United States Patent
Wallach et al.

(10) Patent No.: US 6,734,174 B1
(45) Date of Patent: May 11, 2004

(54) MODULATORS OF THE FUNCTION OF RECEPTORS OF THE TNF/NGF RECEPTOR

(75) Inventors: David Wallach, Rehovot (IL); Andrei Kovalenko, Rehovot (IL); Marshall S. Horwitz, Larchmont, NY (US); Yongan Li, Apex, NC (US)

(73) Assignees: Yeda Research and Development Co. Ltd., Rehovot (IL); Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/646,403

(22) PCT Filed: Mar. 18, 1999

(86) PCT No.: PCT/IL99/00158

§ 371 (c)(1),
(2), (4) Date: Feb. 21, 2001

(87) PCT Pub. No.: WO99/47672

PCT Pub. Date: Sep. 23, 1999

(30) Foreign Application Priority Data

Mar. 19, 1998 (IL) .................................................. 123758
Sep. 1, 1998 (IL) .................................................. 126024

(51) Int. Cl.$^7$ .......................... A61K 31/70; C07K 2/00; C07H 21/04
(52) U.S. Cl. .............................. 514/44; 514/2; 530/350; 536/23.1; 536/23.5; 435/69.1; 435/320.1; 435/455; 435/456; 435/471; 435/476; 435/325; 435/243
(58) Field of Search .............................. 435/69.1, 320.1, 435/455, 456, 471, 476, 325, 243; 536/23.1, 23.5; 530/350; 514/2, 44

(56) References Cited

FOREIGN PATENT DOCUMENTS

| WO | 96 25941 | 8/1996 |
| WO | 96 36730 | 11/1996 |
| WO | 97 15586 | 5/1997 |
| WO | 97 45542 | 12/1997 |

OTHER PUBLICATIONS

Anderson, WF. Human gene therapy. Apr. 30, 1998. Nature 392: 25–30.*
Kmiec, EB. Gene Therapy. May–Jun. 1999. American Scientist 87: 240–247.*
Mountain, A. Gene therapy: the first decade. Mar. 2000. Trends in Biotechnology 18: 119–128.*
Nagase et al, Data DNA Sequence Database 2 Online, "Prediction of the coding sequencesof unidentified human genes, XII. The complete sequence of 100 new cDNA clones from brain which code for large proteins in vitro", (1998), pp. 355–364.
Rothwarf et al., "IKK—is an essential regulatory subunit of the $I_\kappa B$ kinase complex", Nature, (1998) vol. 395, No. 17, pp. 297–300.
Yamaoka et al., "Complementation Cloning of NEMO, a Component of $I_\kappa B$ Kinase Complex Essential for NF–$\kappa B$ Activation", CELL, (1998), vol. 93, pp. 1231–1240.
Li et al., "Identification of a cell protein (FIP–3) as a modulator of NF–$_\kappa$B activity and as a target of an adenovirus inhibitor of tumor necrosis factor α–induced apoptosis", Proc. Natl. Acad. Sci. USA, vol. 96, pp. 1042–1047.
Li et al., "Interaction of an Adenovirus E3 14.7–Kilodalton Protein with a Novel Tumor Necrosis Factory Alpha–Inducible Cellular Protein Containing Leucine Zipper Domains", Molecular and Cellular Biology, (1998), vol. 18, No. 3, pp. 1601–1610.

* cited by examiner

Primary Examiner—David Guzo
Assistant Examiner—David A. Lambertson
(74) Attorney, Agent, or Firm—Browdy and Neimark, P.L.L.C.

(57) ABSTRACT

A protein capable of modulating or mediating the intracellular activity of RIP in inflammation, cell survival and cell death pathways is provided. DNA encoding it, a method for its production and its uses are also provided.

14 Claims, 27 Drawing Sheets

FIG. 1(A)

|  | 10 | 20 | 30 | 40 | 50 | 60 |  |
|---|---|---|---|---|---|---|---|
| 1 | GAAGATTCCA | TTGTGGGCCT | GSGAGGCCTA | GCAAGGGCGG | ACCGCGAAAC | TGGGACTTTT | 60 |
| 61 | TTCGGAGCGC | CGGGCCCTA | CCAGCGTTCA | CAGTCCGCCG | CTCCCACCCT | TCTCACGTCT | 120 |
| 121 | GACGGACTCT | GCTGACAGCC | CTTGCCCTGT | TGGATGAATA | GGCACCTCTG | GAAGAGCCAA | 180 |
| 181 | CTGTGTGAGA | TGGTGCAGCC | CAGTGGTGGC | CCGGCAGCAG | ATCAGGACGT | ACTGGGCGAA | 240 |
| 241 | GAGTCTCCTC | TGGGAAGCC | AGCCATGCTG | CACCTGCCTT | CAGAACAGGG | CGCTCCTGAG | 300 |
| 301 | ACCCTCCAGC | GCTGCCTGA | GAGAATCAA | GAGCTCCGAG | ATGCCATCCG | GCAGAGCAAC | 360 |
| 361 | CAGATTCTGC | GGGAGCGCTG | CGAGGAGCTT | CTGCATTTCC | AAGCCAGCCA | GAGGGAGGAG | 420 |
| 421 | AAGGAGTTCC | TCATGTGCAA | GTTCCAGGAG | GCCAGGAAAC | TGGTGGAGAG | ACTCGGCCTG | 480 |
| 481 | GAGAAGCTCG | ATCTGAAGAG | GCAGAAGGAG | CAGGCTCTGC | GGGAGGTGGA | GCACCTGAAG | 540 |
| 541 | AGATGCCAGC | AGCAGATGGC | TGAGGACAAG | GCCTCTGTGA | AAGCCCAGGT | GACGTCCTTG | 600 |
| 601 | CTCGGGGAGC | TGCAGGAGAG | CCAGAGTCGC | TTGGAGGCTG | CCACTAAGGA | ATGCCAGGCT | 660 |
| 661 | CTGGAGGGTC | GGGCCCGGGC | GGCCAGCGAG | CAGGCGGGC | AGCTGGAGAG | TGAGCGCGAG | 720 |
| 721 | GCGCTGCAGC | AGCAGCACAG | CGTGCAGGTG | GACCAGCTGC | GCATGCAGGG | CCAGAGCGTG | 780 |
| 781 | GAGGCCGCGC | TCCGCATGGA | GCGCCAGGCC | GCCTCGGAGG | AGAAGAGGAA | GCTGGCCCAG | 840 |
| 841 | TTGCAGGTGG | CCTATCACCA | GCTCTTCCAA | GAATACGACA | ACCACATCAA | GAGCAGCGTG | 900 |
| 901 | GTGGGCAGTG | AGCGGAAGCG | AGGAATGCAG | CTGGAAGATC | TCAAACAGCA | GCTCCAGCAG | 960 |
| 961 | GCCGAGGAGG | CCCTGGTGGC | CAAACAGGAA | GTGATCGATA | AGCTGAAGGA | GGAGGCCGAG | 1020 |
| 1021 | CAGCACAAGA | TTGTGATGGA | GACCGTTCCG | GTGCTGAAGG | CCCAGGCGGA | TATCTACAAG | 1080 |
| 1081 | GCGGACTTCC | AGGCTGAGAG | GCAGGCCCGG | GAGAAGCTGG | CCGAGAAGAA | GGAGCTCCTG | 1140 |

FIG. 1(B)

|  | 10 | 20 | 30 | 40 | 50 | 60 |
|---|---|---|---|---|---|---|
| 1141 | CAGGAGCAGC | TGGAGCAGCT | GCAGAGGGAG | TACAGCAAAC | TGAAGGCCAG | CTGTCAGGAG | 1200 |
| 1201 | TCGGCCAGGA | TCGAGGACAT | GAGGAAGCGG | CATGTCGAGG | TCTCCCAGGC | CCCCTTGCCC | 1260 |
| 1261 | CCCGCCCCTG | CCTACCTCTC | CTCTCCCCTG | GCCCTGCCCA | GCCAGAGGAG | GAGCCCCCCC | 1320 |
| 1321 | GAGGAGCCAC | CTGACTTCTG | CTGTCCCAAG | TGCCAGTATC | AGGCCCCTGA | TATGGACACC | 1380 |
| 1381 | CTGCAGATAC | ATGTCATGGA | GTGCATTGAG | TAGGGCCGGC | CAGTGCAAGG | CCACTGCCTG | 1440 |
| 1441 | CCGAGGACGT | GCCCGGGACC | GTGCAGTCTG | CGCTTTCCTC | TCCCGCCTGC | CTAGCCCCAGG | 1500 |
| 1501 | ATGAAGGGCT | GGGTGGCCAC | AACTGGGATG | CCACCTGGAG | CCCCACCCAG | GAGCTGGCCG | 1560 |
| 1561 | CGGCACCTTA | CGCTTCAGCT | GTTGATTCCG | CTGGTCCCCT | CTTTTGGGGT | AGATGCGGCC | 1620 |
| 1621 | CCGATCAGGC | CTGACTCGCT | GCTCTTTTTG | TTCCCTTCTG | TCTGCTCGAA | CCACTTGCCT | 1680 |
| 1681 | CGGGCTAATC | CCTCCCCTCT | CCTCCACCCG | GCACTGGGGA | AGTCAAGAAT | GGGGCCTGGG | 1740 |
| 1741 | GCTCTCAGGG | AGAACTGCTT | CCCCTGGCAG | AGCTGGGTGG | CAGCTCTTCC | TCCCACCGGA | 1800 |
| 1801 | CACCGACCCG | CCCGCTGCTG | TGCCCTGGGA | GTGCTGCCCT | CTTACCATGC | ACACGGGTGC | 1860 |
| 1861 | TCTCCTTTTG | GGCTGCATGC | TATTCCATTT | TGCAGCCAGA | CCGATGTGTA | TTTAACCAGT | 1920 |
| 1921 | CACTATTGAT | GGACATTTGG | GTTGTTTCCC | ATCTTTTTGT | TACCATMAAT | ARTGGCMTAG | 1980 |
| 1981 | AKAAAAATCC | TTGTGCATTA | AAAAAAAAA |  |  |  | 2009 |

FIG. 2(A)

|  | 10 | 20 | 30 | 40 | 50 | 60 |
|---|---|---|---|---|---|---|
| 1 | TTCTACTCCT | CCCTCCTCCT | CACTGCGGGG | TCTGACCCTA | CTCCTTGTGT | GAGGACTCCT | 60 |
| 61 | CTAGTTCAGA | GACATATTCT | GTTCACCAAA | CTTGACTGCG | CTCTATCGAG | GTCGTTAAAT | 120 |
| 121 | TCTTCGGAAA | TGCCTCACAT | ATAGTTTGGC | AGCTAGCCCT | TGCCCTGTTG | GATGAATAGG | 180 |
| 181 | CACCCTCTGA | AGAGCCAACT | GTGTGAGATG | GTGCAGCCCA | GTGGTGGCCC | GGCAGCAGAT | 240 |
| 241 | CAGGACGTAC | TGGGCGAAGA | GTCTCCTCTG | GGGAAGCCAG | CCATGCTGCA | CCTGCCTTCA | 300 |
| 301 | GAACAGGGCG | CTCCTGAGAC | CCTCCAGCGC | TGCCTGGGAG | GAGAATCAAG | AGCTCCGAGA | 360 |
| 361 | TGCCATCCGG | CAGTAGCAAC | CAGATTCTTG | CGGGAGCTGC | CGAAGGGAGC | TTTCTGCATT | 420 |
| 421 | TTCCAAGCCA | GCCAGAGGGA | GGAGAAGGAG | TTCCTCATGT | GCAAGTTCCA | GGAGGCCAGG | 480 |
| 481 | AAACTGGTGG | AGAGACTCGG | CCTGGAGAAG | CTCGATCTGA | AGAGGCAGAA | GGAGCAGGCT | 540 |
| 541 | CTGCGGGAGG | TGGAGCACCT | GAAGAGATGC | CAGCAGCAGA | TGGCTGAGGA | CAAGGCCTCT | 600 |
| 601 | GTGAAAGCCC | AGGTGACGTC | CTTGCTCGGG | GAGCTGCAGG | AGAGCCAGAG | TCGCTTGGAG | 660 |
| 661 | GCTGCCACTA | AGGAATGCAA | GGCTCTGGAG | GGTCGGCCC | GGGCGGCCAG | CGAGCAGGCG | 720 |
| 721 | CGGCAGCTGG | AGAGTGAGCG | CGAGGCGCTG | CAGCAGCAGC | ACAGCGTGCA | GGTGGACCAG | 780 |
| 781 | CTGCGCATGC | AGGGCCAGAG | CGTGCAGGCC | GCGCTCCGCA | TGGAGCGCCA | GGCCGCCTCG | 840 |
| 841 | GAGGAGAAGA | GGAAGCTGGC | CCAGTTGCAG | GTGGCCTATC | ACCAGCTCTT | CCAAGAATAC | 900 |
| 901 | GACAACCACA | TCAAGAGCAG | CGTGGTGGGC | AGTGAGCGGA | AGCGAGGAAT | GCAGCTGGAA | 960 |
| 961 | GATCTCAAAC | AGCAGCTCCA | GCAGGCCGAG | GAGGCCCTGG | TGGCCAAACA | GGAGGTGATC | 1020 |
| 1021 | GATAAGCTGA | AGGAGGAGGC | CGAGCAGCAC | AAGATTGTGA | TGGAGACCGT | TCCGGTGCTG | 1080 |
| 1081 | AAGGCCCAGG | CGGATATCTA | CAAGGCGGAC | TTCCAGGCTG | AGAGGCAGGC | CGGGAGAAG | 1140 |

FIG. 2(B)

```
1141 CTGGCCGAGA AGAAGGAGCT CAGCTGGAGC CCTGCAGGAG AGCTGCAGAG GGAGTACAGC  1200
1201 AAACTGAAGG CCAGCTGTCA GGAGTCGGCC AGGATCGAGG ACATGAGGAA GCGGCATGTC  1260
1261 GAGGTCTCCC AGGCCCCCTT GCCCCCCGCC CCTGCCTACC TCTCCTCTCC CCTGGCCCTG  1320
1321 CCCAGCCAGA GGAGGAGCCC CCCCGAGGAG CCACCTGACT TCTGCTGTCC CAAGTGCCAG  1380
1381 TATCAGGCCC CTGATATGGA CACCCTGACT ATACATGTCA TGGAGTGCAT TGAGTAGGGC  1440
1441 CGGCCAGTGC AAGGCCACTG CCTGCCGAGG ACGTGCCCGG GACCGTGCAG TCTGCGCTTT  1500
1501 CCTCTCCCGC CTGCCTAGCC CAGGATGAAG GGCTGGGTGG CCACAACTGG GATGCCACCT  1560
1561 GGAGCCCCAC CCAGGAGCTG GCGCGGCAC CTTACGCTTC AGCTGTTGAT TCCGCTGGTC  1620
1621 CCCTCTTTTG GGGTAGATGC GCCCCCGATC AGGCCTGACT CGCTGCTCTT TTTGTTCCCT  1680
1681 TCTGTCTGCT CGAACCACTT AATCCCCTCC TCTTCCTCCA CCCGGCACTG CCCGGCACTG  1740
1741 GGGAAGTCAA GAATGGGGCC TGGGGCTCTC AGGGAGAACT GCTTCCCCTG GCAGAGCTGG  1800
1801 GTGGCAGCTC TTCCTCCCAC CGGACACCGA CCCGCCCGCT GCTGTGCCCT GGGAGTGCTG  1860
1861 CCCTCTTACC ATGCACACGG GTGCTCTCCT TTTGGGCTGC ATGCTATTCC ATTTTGCAGC  1920
1921 CAGACCGATG CAGTCACTAT CAGTCACTAT TGATGGACAT TGGGTTGTT TCCCATCTTT  1980
1981 TTGTTACCAT MAATARTGGC MTAGAKAAAA ATCCTTGTGC ATTAAAAAAA AAAA         2034
              |         |          |          |          |          |
              10        20         30         40         50         60
```

```
20.4 full    208  SVEPAMPRMDPRQAANSFEKRKLAQLQQVAAYHQLFQEQY D
NEMO full    210  SVEAVIRMEIRQAASETAASEEKRKLAQLQQVAQYHQLFQDY D
Mouse part.  141  AWRLPCEWSGRLLQRSGTGLDLQAAXHQLFQDY D
Human shrt    60  -------------------------------- -

20.4 full    243  NHIKSS    VVGSERK    RPGMQLEDLKQQQQQVEALVAK
NEMO full    245  SHIKSS                KGMQLEDLRQQQQQAEALVAR
Mouse part.  176  SHIKRS                KGMQLEDIRQQLQQAEALVAK
Human shrt    60  --------              --------------------

20.4 full    278  QEYIHD KQKLKTKEAEQLKTKLVMETY P VLKAQADIYKADF
NEMO full    273  QELLDL KCKEELEQHKLVMETY E VLKAQADIYKADE
Mouse part.  204  QELQDIKTKELEQHAEQHKLCD ERM   VLKAQADIYKADE
Human shrt    60  ------------------------     --------------

20.4 full    313  QAERQAREKLAEKKELLQEQLQREYS KLKASQ
NEMO full    308  QAERHAREKLVEKKEKLQEQLQREEN KLKVGQ
Mouse part.    0  
Human shrt    60

20.4 full    348  QESARIEDMRKKRHV V SQAPLPPAPAYL SPLALP
NEMO full    343  HESARIEDMRKKRHV E - TQPPLPAPAH SFHLALS
Mouse part.    0  
Human shrt    60

20.4 full    383  SQRRSPPEEPPPDF CCCPKCQYQ A EDMDTLQIHVME
NEMO full    377  NQRRSPPEEPPPDF SGPKCQYQ A EDMDTLQIHVME
Mouse part.    0  
Human shrt    60  LQMHTG AILQGMLEHFAA 20.4 full    416  --- GIL
NEMO full    411  ---
Mouse part.    0  RPM CIL
Human shrt    82  
```

FIG.3(B)1

```
20.4 full      1   MNRHLWKSQLCE V- SGPAADQVLG ESPLG
FIP-2 full     1    -   -     - SH LTEKEDSPS GN 20.4 full     35   KRAM LHLPS QT GPAT -Q PAADEE IM
FIP-2 full    24    P PHAH PNL ED TE LQMKTEL QH RDAI
                                                 KEAM 20.4 full     66   RQS NOIR GC LHE QASKR EKE MCKFQ ESEA
FIP-2 full    59    K AM EMKG RF SAW TEKRQR EL EIQ AK 20.4 full    101   RKV ERT GLE KLV DKRQ ALRE VEHKRC QMRS
FIP-2 full    94    K ER  -  - MA HEN KKOKLK LGKQQ GKSERS 20.4 full    136   ATED KA   - - KA PT PRAEAE QEKD LRTQVV RLQAEK GEAEGS AD
FIP-2 full   122    S      - -    DDSRLP 20.4 full    141    -  -  -  -  - - LLGIVSELQLKLNS SEDSFVEIRMAEGEEGS
FIP-2 full   157

20.4 full    141    -  -  -  -  - - VKEIKHSPGSTRTVSTGTALSHYRRSADGAKNYF
FIP-2 full   192

20.4 full    141    -  -  -  -  - - EHEELTVSQLLCLREGNQKVERLEVALKEAKERV
FIP-2 full   227

20.4 full    141    -  -  -  -  - - SDFEKKTSNRSEIETQTEGSTEKENDEERGPETVG
FIP-2 full   262
```

FIG.3(B)2

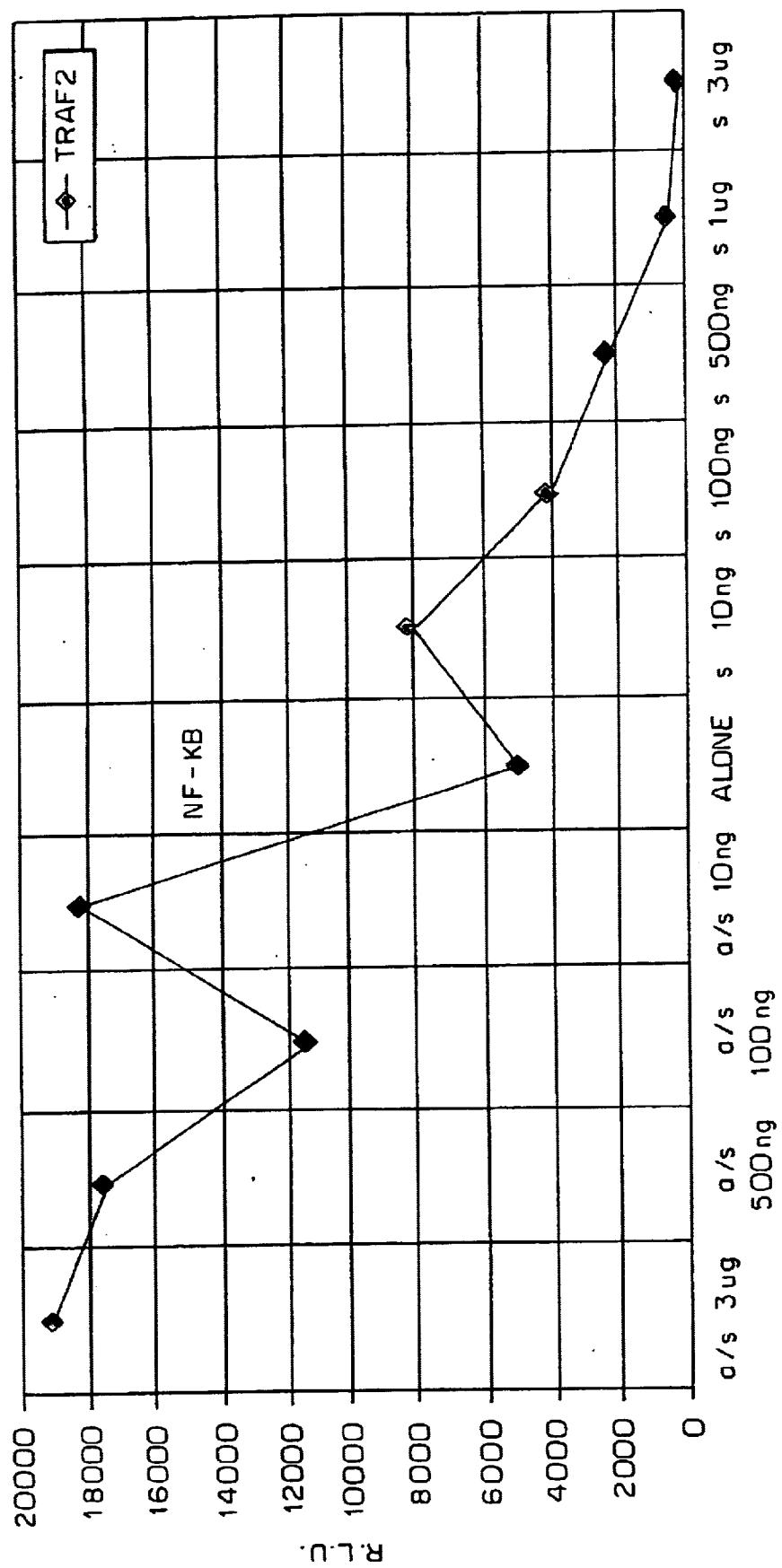

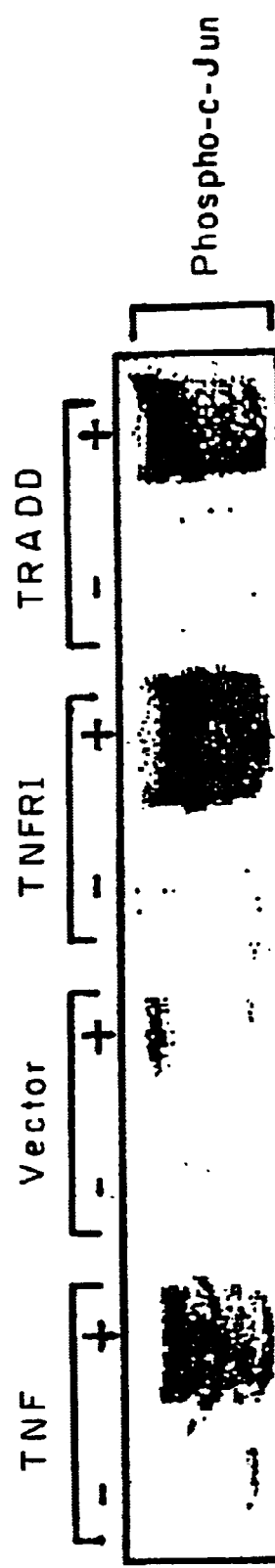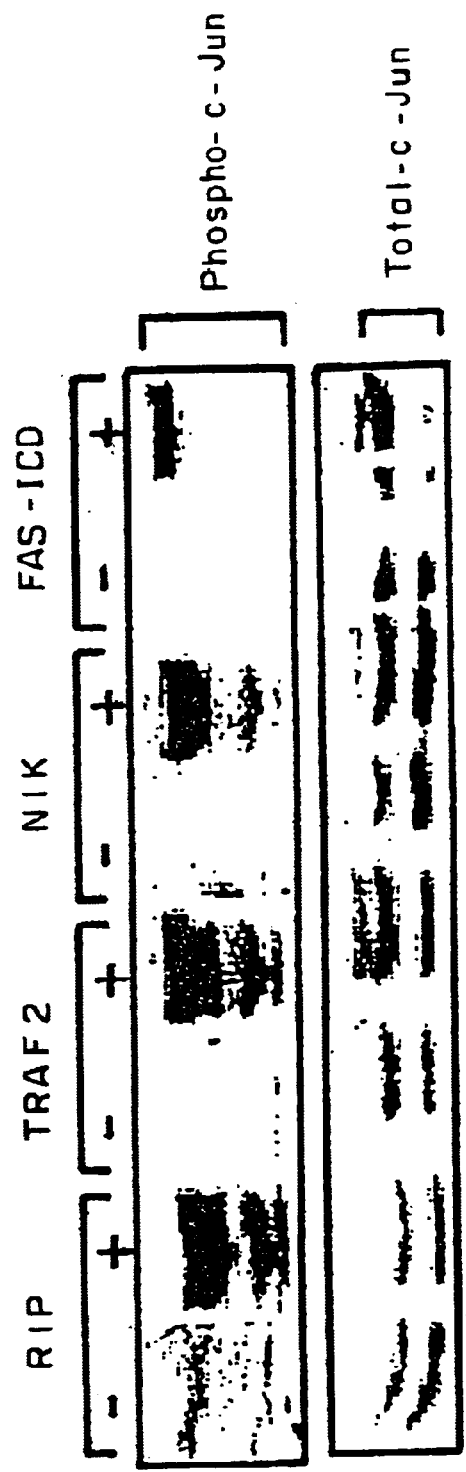
FIG. 7A(1)
FIG. 7A(2)

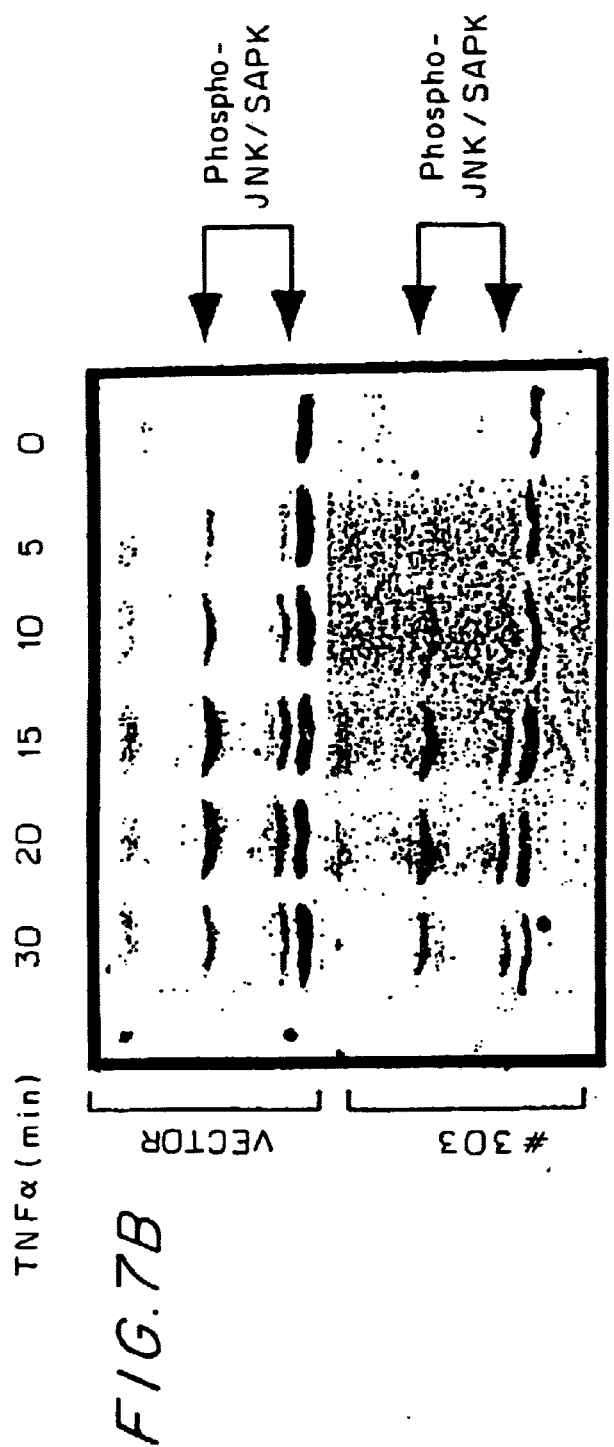
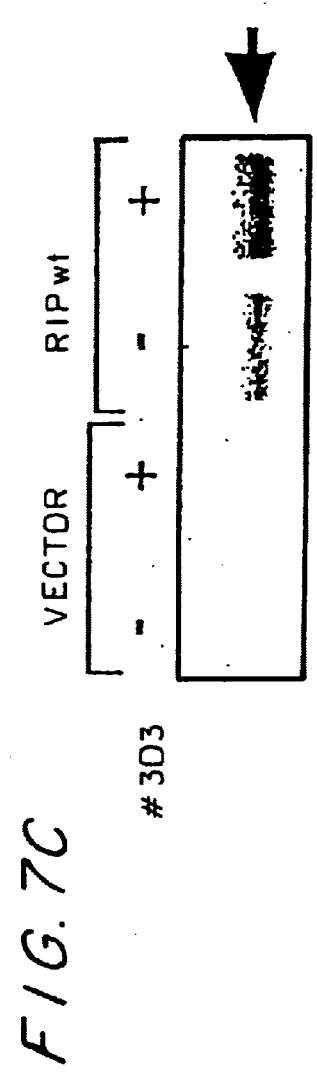
FIG.7B
FIG.7C

FIG. 10A

```
         10         20         30         40         50         60         70         80         90        100
          |          |          |          |          |          |          |          |          |          |
   1  GCCACGAAGG CCCAGACTTT GACCGTTCTT CACCACCACT CCAGCCTCCT CCTGTGAACT CACTGACCAC CGAGAACAGA TTCCACTCTT TACCATTCAG  100
 101  TCTCACCAAG ATGCCCAATA CCAATGGAAG TATTGGCCAC AGTCCACTTT CTCTGTCAGC CCAGTCTGTA ATGAAGAGC TAAACACTGC ACCCGTCCAA  200
 201  GAGAGTCCAC CCTTGGCCAT GCCTCCTGGG AACTCACATG GTCTAGAAGT GCTGAAGTTA AGGAGAACCC TCCTTTCTAT GGGGTAATCC  300
 301  GTTGGATCGG TCAGCCACCA GGACTGAATG AAGTGCTCGC TGGACTGGAA CTGGAAGATG CTGGAGCAGG CTGTACGGAT GAAACCTTCA GAGGCACTCG  400
 401  GTATTCACC TGTGCCCTGA AGAAGGGGCT GTTTGTGTAA CTGAAGTGAAA GCAGGCCTGA CTCTAGGTTT GCATCATTGC AGCCGGTTTC CAATCAAGAT  500
 501  TGAGCGCTGT AACTCTTTAG CATTGGAAGG CTACTTAAGT GAAGTAGT:G AAGAAAATAC T:CCA:CCAA AAATGGAAAA AGAAAGCTTG GAGATAATGA  600
 601  TTGGGGAAAG AAGAAAGGCA TCCAAGGGTC ATTACAATTC TTGKTACTTA G:ACTCAACC TTATTCTKGC TTATTTKGT TTTAGTTCTG TTCTNGGACA  700
 701  CTGGTGTTAC TTTAGACCCC AAAGAAAAAG AGATAATATGTT WKWGMACCC AAGAGCTACT GAGGACAGAA ATTGTTAATC CTCTGAGAAT  800
 801  ATATGGATAT GTGTGTGCCA CAAAAATTAT GAAACTGAGG AAAATACTTG AAAAGGTGGA GGCTGCATCA GGATTTACCT CTGAAGAAAA AGATCCTGAG  900
 901  GAATTCTTGA ATATTCTGTT TCATCATATT AAAGTTGGCG AAAATAAGA TCAGCAGGTC TTTTTATCAA AAAAGGTACA AGATTGTTAC TTTCTATCAAA 1000
1001  TTTTATGGA AAAAAKTGAG AAAGTTGGCG TTCCACAAT TCAGCAGTTG TTAGAATGGT CTTTTATCAA AATTTGCAG AGGCACCATC 1100
1101  ATGTCTGATT ATTCAGATGC CTCGATTTGG AAAAGACTTT AAACTATTTA AAAAATTTTT CCTTCTCTGG AATTAGATAT AACAGATTTA CTTGAAGACA 1200
1201  CCCCAGACAG TGCCGGATAT GTGGAGGGCT TGCAATGTAT GAGTGTAAGA ATGCTACGAC GATCCGGACA CCAGCTGAAA AAACAAGCAG TTTTGTAAAA 1300
```

FIG. 10B

```
1301 CCTGCAACAC TCAAGTCCAC CTTCATCCGA AGAGGCTGAA TCATAAATAT AACCCAGTGT CACTTCCCAA AGACTTACCC CGACTGGGAG ATTGGAGACA 1400
1401 CGGCTGCATC CCTTGCCAGA ATATGGAGTT ATTTGCTGTT CTCTGCATAG AAACAAGCCA CTATGTTGCT TTTGTGAAGT ATGGAAGGA CGATTCTGCC 1500
1501 TGGCTCTTCT TTGGACAGCA TGGCCGATCC GGGATGGTGG TCAGAATGGC TCAACATTCC CCCAAGTCMC CCMTGSCCCA GAAGTAGGAG AGTACTTGGA 1600
1601 AGATGTCTCC TGGAAGACCC TGSAWTYCCT TGGACTCCCA AAGGCTGTGC ACGAAGACTG CTTTGTGATG CCATATATGT GCCATGTACC 1700
1701 CAGAGTCCAA CAATGAGTTT GTACAAATAA CTGGGGGTCA TCGGGAAAGG CAAAGAAACT GGAAGGCAGA GTCCCTAACG TTGCATCTTA TTCGGAGCTG 1800
1801 GCAGTTCTGT TCACGGTCCA TTGCCGGCAA TGGATGTCTT TGTGGTGATG ATCCTTCAGA AAAGGATGCC TCTGTTTAAA AACAAATTGC TTTTGTGTCC 1900
1901 CTGAAGTATT TAATAAGAAG CATTTTTGCAC TCTAGAAAGT ATGTTTGTGT TGGTTTTTTA AGAAGTCTAA ATGAAGTTAT TAATACCTGA AGCTTTAAGT 2000
2001 TAAGTGCATT GATCATATGA TATTTTTGGA AGCATACACT TTTAATTGTG GAAGTTTAAA GCCTCTTTTA GTCCATTGAG AATGTAAATA AATGTGTCTT 2100
2101 CTTTATGGAA AAAAAA 2116
           |        |        |        |        |        |        |        |        |        |        |
           10       20       30       40       50       60       70       80       90       100
```

FIG. 12A

```
                         SEQUENCE LISTING

<160> NUMBER OF SEQ ID NOS: 8

<210> SEQ ID NO 1
<211> LENGTH: 2009
<212> TYPE: DNA
<213> ORGANISM: Homo sapiens

<400> SEQUENCE: 1
gaagattcca ttgtgggcct gsgaggccta gcaagggcgg accgcgaaac tgggactttt      60
ttcggagcgc cggggcccta ccagcgttca cagtccgccg ctcccaccct tctcacgtct     120
gacggactct gctgacagcc cttgccctgt tggatgaata ggcacctctg gaagagccaa     180
ctgtgtgaga tggtgcagcc cagtggtggc ccggcagcag atcaggacgt actgggcgaa     240
gagtctcctc tggggaagcc agccatgctg cacctgcctt cagaacaggg cgctcctgag     300
accctccagc gctgcctgga ggagaatcaa gagctccgag atgccatccg gcagagcaac     360
cagattctgc gggagcgctg cgaggagctt ctgcatttcc aagccagcca gagggaggag     420
aaggagttcc tcatgtgcaa gttccaggag gccaggaaac tggtggagag actcggcctg     480
gagaagctcg atctgaagag gcagaaggag caggctctgc gggaggtgga gcacctgaag     540
agatgccagc agcagatggc tgaggacaag gcctctgtga agcccaggt gacgtccttg     600 ctcggggagc tgcaggagag ccagagtcgc ttggaggctg ccactaagga atgccaggct     660
ctggagggtc gggcccgggc ggccagcgag caggcgcggc agctggagag tgagcgcgag     720
gcgctgcagc agcagcacag cgtgcaggtg gaccagctgc gcatgcaggg ccagagcgtg     780
gaggccgcgc tccgcatgga gcgccaggcc gcctcggagg agaagaggaa gctggcccag     840
ttgcaggtgg cctatcacca gctcttccaa gaatacgaca accacatcaa gagcagcgtg     900
gtgggcagtg agcggaagcg aggaatgcag ctggaagatc tcaaacagca gctccagcag     960
gccgaggagg ccctggtggc caaacaggag gtgatcgata agctgaagga ggaggccgag    1020
cagcacaaga ttgtgatgga gaccgttccg gtgctgaagg cccaggcgga tatctacaag    1080
gcggacttcc aggctgagag gcaggccgg gagaagctgg ccgagaagaa ggagctcctg    1140
caggagcagc tggagcagct gcagagggag tacagcaaac tgaaggccag ctgtcaggag    1200
```

| | |
|---|---|
| tcggccagga tcgaggacat gaggaagcgg catgtcgagg tctcccaggc cccttgccc | 1260 |
| cccgcccctg cctacctctc ctctcccctg gccctgccca gccagaggag gagccccccc | 1320 |
| gaggagccac ctgacttctg ctgtcccaag tgccagtatc aggcccctga tatggacacc | 1380 |
| ctgcagatac atgtcatgga gtgcattgag tagggccggc cagtgcaagg ccactgcctg | 1440 |
| ccgaggacgt gcccgggacc gtgcagtctg cgctttcctc tcccgcctgc ctagcccagg | 1500 |
| atgaagggct gggtggccac aactgggatg ccacctggag ccccacccag gagctggccg | 1560 |
| cggcacctta cgcttcagct gttgattccg ctggtcccct cttttggggt agatgcggcc | 1620 |
| ccgatcaggc ctgactcgct gctcttttg ttcccttctg tctgctcgaa ccacttgcct | 1680 |
| cgggctaatc cctccctctt cctccacccg gcactgggga agtcaagaat ggggcctggg | 1740 |
| gctctcaggg agaactgctt cccctggcag agctgggtgg cagctcttcc tcccaccgga | 1800 |
| caccgacccg cccgctgctg tgccctggga gtgctgccct cttaccatgc acacgggtgc | 1860 |
| tctccttttg ggctgcatgc tattccattt tgcagccaga ccgatgtgta tttaaccagt | 1920 |
| cactattgat ggacatttgg gttgtttccc atcttttgt taccatmaat artggcmtag | 1980 |
| akaaaaatcc ttgtgcatta aaaaaaaaa | 2009 |

<210> SEQ ID NO 2
<211> LENGTH: 2034
<212> TYPE: DNA
<213> ORGANISM: Homo sapiens

<400> SEQUENCE: 2

| | |
|---|---|
| ttctactcct ccctcctcct cactgcgggg tctgaccta ctccttgtgt gaggactcct | 60 |
| ctagttcaga gacatattct gttcaccaaa cttgactgcg ctctatcgag gtcgttaaat | 120 |
| tcttcggaaa tgcctcacat atagtttggc agctagccct tgccctgttg gatgaatagg | 180 |
| cacctctgga gagccaact gtgtgagatg gtgcagccca gtggtggccc ggcagcagat | 240 |
| caggacgtac tgggcgaaga gtctcctctg gggaagccag ccatgctgca cctgccttca | 300 |
| gaacagggcg ctcctgagac cctccagcgc tgcctgggag gagaatcaag agctccgaga | 360 |
| tgccatccgg cagtagcaac cagattcttg cgggagctgc cgaagggagc tttctgcatt | 420 |
| ttccaagcca gccagaggga ggagaaggag ttcctcatgt gcaagttcca ggaggccagg | 480 |
| aaactggtgg agagactcgg cctggagaag ctcgatctga gaggcagaa ggagcaggct | 540 |
| ctgcgggagt ggagcacct gaagagatgc cagcagcaga tggctgagga caaggcctct | 600 |
| gtgaaagccc aggtgacgtc cttgctcggg gagctgcagg agagccagag tcgcttggag | 660 |
| gctgccacta aggaatgcca ggctctggag gtcgggccc gggcggccag cgagcaggcg | 720 |
| cggcagctgg agagtgagcg cgaggcgctg cagcagcagc acagcgtgca ggtggaccag | 780 |
| ctgcgcatgc agggccagag cgtggaggcc gcgctccgca tggagcgcca ggccgcctcg | 840 |
| gaggagaaga ggaagctggc ccagttgcag gtggcctatc accagctctt ccaagaatac | 900 |
| gacaaccaca tcaagagcag cgtggtgggc agtgagcgga agcgaggaat gcagctggaa | 960 |
| gatctcaaac agcagctcca gcaggccgag gaggccctgg tggccaaaca ggaggtgatc | 1020 |
| gataagctga aggaggaggc cgagcagcac aagattgtga tggagaccgt tccggtgctg | 1080 |
| aaggcccagg cggatatcta caaggcggac ttccaggctg agaggcaggc ccgggagaag | 1140 |
| ctggccgaga gaaggagct cctgcaggag cagctggagc agctgcagag ggagtacagc | 1200 |
| aaactgaagg ccagctgtca ggagtcgcc aggatcgagg acatgaggaa gcggcatgtc | 1260 |
| gaggtctccc aggccccctt gccccccgcc cctgcctacc tctcctctcc cctggccctg | 1320 |

```
cccagccaga ggaggagccc ccccgaggag ccacctgact tctgctgtcc caagtgccag    1380
tatcaggccc ctgatatgga caccctgcag atacatgtca tggagtgcat tgagtagggc    1440
cggccagtgc aaggccactg cctgccgagg acgtgcccgg gaccgtgcag tctgcgcttt    1500
cctctcccgc ctgcctagcc caggatgaag ggctgggtgg ccacaactgg gatgccacct    1560
ggagccccac ccaggagctg gccgcggcac cttacgcttc agctgttgat tccgctggtc    1620
ccctcttttg gggtagatgc ggccccgatc aggcctgact cgctgctctt tttgttccct    1680
tctgtctgct cgaaccactt gcctcgggct aatccctccc tcttcctcca cccggcactg    1740
gggaagtcaa gaatgggggcc tggggctctc agggagaact gcttcccctg gcagagctgg    1800
gtggcagctc ttcctcccac cggacaccga cccgcccgct gctgtgccct gggagtgctg    1860
ccctcttacc atgcacacgg gtgctctcct tttgggctgc atgctattcc attttgcagc    1920
cagaccgatg tgtatttaac cagtcactat tgatggacat ttgggttgtt tcccatcttt    1980
ttgttaccat maatartggc mtagakaaaa atccttgtgc attaaaaaaa aaaa    2034

<210> SEQ ID NO 3
<211> LENGTH: 2116
<212> TYPE: DNA
<213> ORGANISM: Homo sapiens
<220> FEATURE:
<221> NAME/KEY: misc_feature
<222> LOCATION: (691)..(691)
<223> OTHER INFORMATION: n is unknown.

<400> SEQUENCE: 3
gccacgaagg cccagacttt gaccgttctt caccaccact ccagcctcct cctgtgaact      60
cactgaccac cgagaacaga ttccactctt taccattcag tctcaccaag atgcccaata     120
ccaatggaag tattggccac agtccacttt ctctgtcagc ccagtctgta atggaagagc     180
taaacactgc acccgtccaa gagagtccac ccttggccat gcctcctggg aactcacatg     240
gtctagaagt gggctcattg gctgaagtta aggagaaccc tccttttctat ggggtaatcc     300 gttggatcgg tcagccacca ggactgaatg aagtgctcgc tggactggaa ctggaagatg     360
agtgtgcagg ctgtacggat ggaaccttca gaggcactcg gtatttcacc tgtgccctga     420
agaaggcgct gtttgtgaaa ctgaagagct gcaggcctga ctctaggttt gcatcattgc     480
agccggtttc caatcaagat tgagcgctgt aactctttag catttggagg ctacttaagt     540
gaagtagtga agaaaatact ccaccaaaaa tggaaaaaga argcttggag ataatgattg     600
gggaaagaag aaaggcatcc aagggtcatt acaattcttg ktacttagac tcaaccttat     660
tctkgcttat ttkgctttta gttctgttct nggacactgg tgttacttta gaccccaaag     720
aaaaagaaac gatgttagaa tattwtwkwg mmacccaaga gctactgagg acagaaattg     780
ttaatcctct gagaatatat ggatatgtgt gtgccacaaa aattatgaaa ctgaggaaaa     840
tacttgaaaa ggtggaggct gcatcaggat ttacctctga agaaaaagat cctgaggaat     900
tcttgaatat tctgtttcat catattttaa gggtagaacc tttgctaaaa ataagatcag     960
caggtcaaaa ggtacaagat tgttacttct atcaaatttt tatggaaaaa aatgagaaag    1020
ttggcgttcc cacaattcag cagttgttag aatggtcttt tatcaacagt aacctgaaat    1080
ttgcagaggc accatcatgt ctgattattc agatgcctcg atttggaaaa gactttaaac    1140
tatttaaaaa attttttcctt ctctggaatt agatataaca gatttacttg aagacacccc    1200
agacagtgcc ggatatgtgg agggcttgca atgtatgagt gtaagaatgc tacgacgatc    1260
```

-continued

```
cggacaccag ctggaaaaac aagcagtttt gtaaaacctg caacactcaa gtccaccttc      1320
atccgaagag gctgaatcat aaatataacc cagtgtcact tcccaaagac ttaccccgac      1380
tgggagattg gagacacggc tgcatccctt gccagaatat ggagttattt gctgttctct      1440
gcatagaaac aagccactat gttgcttttg tgaagtatgg gaaggacgat tctgcctggc      1500
tcttctttgg acagcatggc cgatccggga tggtggtcag aatggctcaa cattccccca      1560
agtcmcccmt gscccagaag taggagagta cttggaagat gtctcctgga agaccctgsa      1620
wtyccttgga ctcccaggag aatcccaagg ctgtgcacga agactgcttt gtgatgccat      1680
atatgtgcca tgtacccaga gtccaacaat gagtttgtac aaataactgg gggtcatcgg      1740
gaaaggcaaa gaaactggaa ggcagagtcc ctaacgttgc atcttattcg gagctggcag      1800
ttctgttcac ggtccattgc cggcaatgga tgtctttgtg gtgatgatcc ttcagaaaag      1860
gatgcctctg tttaaaaaca aattgctttt gtgtccctga agtatttaat aagaagcatt      1920
ttgcactcta gaaagtatgt ttgtgttggt tttttaagaa gtctaaatga agttattaat      1980
acctgaagct ttaagttaag tgcattgatc atatgatatt tttggaagca tacaattta      2040 attgtggaag tttaaagcct cttttagtcc attgagaatg taaataaatg tgtcttcttt      2100
atggaaaaaa aaaaaa                                                      2116
```

<210> SEQ ID NO 4
<211> LENGTH: 419
<212> TYPE: PRT
<213> ORGANISM: Homo sapiens

<400> SEQUENCE: 4

```
Met Asn Arg His Leu Trp Lys Ser Gln Leu Cys Glu Met Val Gln Pro
1               5                   10                  15

Ser Gly Gly Pro Ala Ala Asp Gln Asp Val Leu Gly Glu Ser Pro
            20                  25                  30

Leu Gly Lys Pro Ala Met Leu His Leu Pro Ser Glu Gln Gly Ala Pro
        35                  40                  45

Glu Thr Leu Gln Arg Cys Leu Glu Glu Asn Gln Glu Leu Arg Asp Ala
    50                  55                  60

Ile Arg Gln Ser Asn Gln Ile Leu Arg Glu Arg Cys Glu Glu Leu Leu
65                  70                  75                  80

His Phe Gln Ala Ser Gln Arg Glu Glu Lys Glu Phe Leu Met Cys Lys
                85                  90                  95

Phe Gln Glu Ala Arg Lys Leu Val Glu Arg Leu Gly Leu Glu Lys Leu
            100                 105                 110

Asp Leu Lys Arg Gln Lys Glu Gln Ala Leu Arg Glu Val Glu His Leu
        115                 120                 125

Lys Arg Cys Gln Gln Gln Met Ala Glu Asp Lys Ala Ser Val Lys Ala
    130                 135                 140

Gln Val Thr Ser Leu Leu Gly Glu Leu Gln Glu Ser Gln Ser Arg Leu
145                 150                 155                 160

Glu Ala Ala Thr Lys Glu Cys Gln Ala Leu Glu Gly Arg Ala Arg Ala
                165                 170                 175

Ala Ser Glu Gln Ala Arg Gln Leu Glu Ser Glu Arg Glu Ala Leu Gln
            180                 185                 190

Gln Gln His Ser Val Gln Val Asp Gln Leu Arg Met Gln Gly Gln Ser
        195                 200                 205

Val Glu Ala Ala Leu Arg Met Glu Arg Gln Ala Ala Ser Glu Glu Lys
    210                 215                 220
```

```
Arg Lys Leu Ala Gln Leu Gln Val Ala Tyr His Gln Leu Phe Gln Glu
225                 230                 235                 240

Tyr Asp Asn His Ile Lys Ser Ser Val Val Gly Ser Glu Arg Lys Arg
                245                 250                 255

Gly Met Gln Leu Glu Asp Leu Lys Gln Leu Gln Gln Ala Glu Glu
            260                 265                 270

Ala Leu Val Ala Lys Gln Glu Val Ile Asp Lys Leu Lys Glu Glu Ala
            275                 280                 285

Glu Gln His Lys Ile Val Met Glu Thr Val Pro Val Leu Lys Ala Gln
        290                 295                 300

Ala Asp Ile Tyr Lys Ala Asp Phe Gln Ala Glu Arg Gln Ala Arg Glu
305                 310                 315                 320

Lys Leu Ala Glu Lys Lys Glu Leu Leu Gln Glu Gln Leu Glu Gln Leu
                325                 330                 335

Gln Arg Glu Tyr Ser Lys Leu Lys Ala Ser Cys Gln Glu Ser Ala Arg
            340                 345                 350

Ile Glu Asp Met Arg Lys Arg His Val Glu Val Ser Gln Ala Pro Leu
            355                 360                 365

Pro Pro Ala Pro Ala Tyr Leu Ser Ser Pro Leu Ala Leu Pro Ser Gln
        370                 375                 380

Arg Arg Ser Pro Pro Glu Pro Pro Asp Phe Cys Cys Pro Lys Cys
385                 390                 395                 400

Gln Tyr Gln Ala Pro Asp Met Asp Thr Leu Gln Ile His Val Met Glu
            405                 410                 415

Cys Ile Glu

<210> SEQ ID NO 5
<211> LENGTH: 412
<212> TYPE: PRT
<213> ORGANISM: Mouse

<400> SEQUENCE: 5

Met Asn Lys His Pro Trp Lys Asn Gln Leu Ser Glu Thr Val Gln Glu
1               5                   10                  15

Ser Gly Gly Pro Ala Glu Asp Gln Asp Met Leu Gly Glu Glu Ser Ser
            20                  25                  30

Leu Gly Lys Pro Ala Met Leu His Leu Pro Ser Glu Gln Gly Thr Pro
        35                  40                  45

Glu Thr Leu Gln Arg Cys Leu Glu Glu Met Gln Glu Leu Arg Asp Ala
    50                  55                  60

Ile Arg Gln Ser Asn Gln Met Leu Arg Glu Arg Cys Glu Glu Leu Leu
65                  70                  75                  80

His Phe Gln Val Ser Gln Arg Trp Lys Glu Phe Leu Met Cys Lys Phe
                85                  90                  95

Gln Glu Ala Arg Lys Leu Val Glu Arg Leu Ser Leu Glu Lys Leu Glu
            100                 105                 110

Lys Leu Asp Leu Arg Ser Gln Glu Gln Ala Leu Lys Glu Leu Glu
            115                 120                 125

Gln Leu Lys Lys Cys Gln Gln Gln Met Ala Glu Asp Lys Ala Ser Val
    130                 135                 140

Lys Ala Gln Val Thr Ser Leu Leu Gly Glu Leu Gln Glu Ser Gln Ser
145                 150                 155                 160

Arg Leu Glu Ala Ala Thr Lys Asp Arg Gln Ala Leu Glu Gly Arg Ile
                165                 170                 175
```

```
Arg Ala Val Ser Glu Gln Val Arg Gln Leu Glu Ser Glu Arg Glu Val
            180                 185                 190

Leu Gln Gln Gln His Ser Val Gln Val Asp Gln Leu Arg Met Gln Asn
        195                 200                 205

Gln Ser Val Glu Ala Ala Leu Arg Met Glu Arg Gln Ala Ala Ser Glu
    210                 215                 220

Glu Lys Arg Lys Leu Ala Gln Leu Gln Ala Ala Tyr His Gln Leu Phe
225                 230                 235                 240

Gln Asp Tyr Asp Ser His Ile Lys Ser Ser Lys Gly Met Gln Leu Glu
                245                 250                 255

Asp Leu Arg Gln Gln Leu Gln Gln Ala Glu Glu Ala Leu Val Ala Lys
            260                 265                 270

Gln Glu Leu Ile Asp Lys Leu Lys Glu Glu Ala Glu Gln His Lys Ile
        275                 280                 285

Val Met Glu Thr Val Glu Val Leu Lys Ala Gln Ala Asp Ile Tyr Lys
    290                 295                 300

Ala Asp Phe Gln Ala Glu Arg His Ala Arg Glu Lys Leu Val Glu Lys
305                 310                 315                 320

Lys Glu Tyr Leu Gln Glu Gln Leu Glu Gln Leu Gln Arg Glu Phe Asn
                325                 330                 335

Lys Leu Lys Val Gly Cys His Glu Ser Ala Arg Ile Glu Asp Met Arg
            340                 345                 350

Lys Arg His Val Glu Thr Gln Pro Pro Leu Leu Pro Ala Pro Ala His
        355                 360                 365

His Ser Phe His Leu Ala Leu Ser Asn Gln Arg Arg Ser Pro Pro Glu
    370                 375                 380

Glu Pro Pro Asp Phe Cys Cys Pro Lys Cys Gln Tyr Gln Ala Pro Asp
385                 390                 395                 400

Met Asp Thr Leu Gln Ile His Val Met Glu Cys Ile
                405                 410

<210> SEQ ID NO 6
<211> LENGTH: 224
<212> TYPE: PRT
<213> ORGANISM: Mouse

<400> SEQUENCE: 6

Leu Ser Gln Met Leu Arg Glu Arg Cys Glu Glu Leu His Phe Gln
1               5                   10                  15

Val Ser Gln Arg Glu Glu Lys Glu Phe Leu Met Cys Lys Phe Gln Glu
            20                  25                  30

Ala Arg Lys Leu Val Glu Arg Leu Ser Leu Glu Lys Leu Asp Leu Arg
        35                  40                  45

Ser Gln Arg Glu Gln Ala Leu Lys Glu Leu Glu Gln Leu Lys Lys Cys
    50                  55                  60

Gln Gln Gln Met Ala Glu Asp Lys Ala Ser Val Lys Ala Gln Val Thr
65                  70                  75                  80

Ser Leu Leu Gly Glu Leu Gln Glu Ser Gln Ser Arg Leu Glu Ala Ala
                85                  90                  95

Thr Lys Asp Arg Gln Ala Leu Glu Gly Arg Ile Arg Ala Val Ser Glu
            100                 105                 110

Gln Val Arg Gln Leu Glu Ser Glu Arg Glu Val Leu Gln Gln Gln His
        115                 120                 125

Ser Val Gln Val Asp Gln Leu Arg Met Arg Thr Arg Ala Trp Arg Leu
```

```
        130                 135                 140
Pro Cys Glu Trp Ser Gly Arg Leu Leu Gln Arg Arg Ser Gly Thr Gly
145                 150                 155                 160

Leu Gln Leu Gln Ala Ala Tyr His Gln Leu Phe Gln Asp Tyr Asp Ser
                165                 170                 175

His Ile Lys Ser Ser Lys Gly Met Gln Leu Glu Asp Leu Arg Gln Gln
            180                 185                 190

Leu Gln Gln Ala Glu Glu Ala Leu Val Ala Lys Gln Glu Leu Ile Asp
        195                 200                 205

Lys Leu Lys Glu Glu Ala Glu Gln His Lys Ile Cys Asp Glu Thr Val
    210                 215                 220

<210> SEQ ID NO 7
<211> LENGTH: 85
<212> TYPE: PRT
<213> ORGANISM: Homo sapiens

<400> SEQUENCE: 7

Met Asn Arg His Leu Trp Lys Ser Gln Leu Cys Glu Met Val Gln Pro
1               5                   10                  15

Ser Gly Gly Pro Ala Ala Asp Gln Asp Val Leu Gly Glu Glu Ser Pro
            20                  25                  30

Leu Gly Glu Asp Lys Ala Ser Val Lys Ala Gln Val Thr Ser Leu Leu
        35                  40                  45

Gly Glu Leu Gln Glu Ser Gln Ser Arg Trp Glu Cys Cys Pro Leu Thr
    50                  55                  60

Met His Thr Gly Ala Leu Leu Gly Cys Met Leu Phe His Phe Ala Ala
65                  70                  75                  80

Arg Pro Met Cys Ile
                85

<210> SEQ ID NO 8
<211> LENGTH: 576
<212> TYPE: PRT
<213> ORGANISM: Unknown
<220> FEATURE:
<223> OTHER INFORMATION: Unknown

<400> SEQUENCE: 8

Met Ser His Gln Pro Leu Ser Cys Leu Thr Glu Lys Glu Asp Ser Pro
1               5                   10                  15

Ser Glu Ser Thr Gly Asn Gly Pro Pro His Leu Ala His Pro Asn Leu
            20                  25                  30

Asp Thr Phe Thr Pro Glu Glu Leu Leu Gln Gln Met Lys Glu Leu Leu
        35                  40                  45

Thr Glu Asn His Gln Leu Lys Glu Ala Met Lys Leu Asn Asn Gln Ala
    50                  55                  60

Met Lys Gly Arg Phe Glu Glu Leu Ser Ala Trp Thr Glu Lys Gln Lys
65                  70                  75                  80

Glu Glu Arg Gln Phe Phe Glu Ile Gln Ser Lys Glu Ala Lys Glu Arg
                85                  90                  95

Leu Met Ala Leu Ser His Glu Asn Glu Lys Leu Lys Glu Glu Leu Gly
            100                 105                 110

Lys Leu Lys Gly Lys Ser Glu Arg Ser Ser Glu Asp Pro Thr Asp Asp
        115                 120                 125

Ser Arg Leu Pro Arg Ala Glu Ala Gln Glu Lys Asp Gln Leu Arg
        130                 135                 140
```

-continued

```
Thr Gln Val Val Arg Leu Gln Ala Glu Lys Ala Asp Leu Leu Gly Ile
145                 150                 155                 160

Val Ser Glu Leu Gln Leu Lys Leu Asn Ser Ser Gly Ser Ser Glu Asp
            165                 170                 175

Ser Phe Val Glu Ile Arg Met Ala Glu Gly Ala Glu Gly Ser Val
            180                 185                 190

Lys Glu Ile Lys His Ser Pro Gly Ser Thr Arg Thr Val Ser Thr Gly
            195                 200                 205

Thr Ala Leu Ser His Tyr Arg Arg Ser Ala Asp Gly Ala Lys Asn
        210                 215                 220

Tyr Phe Glu His Glu Glu Leu Thr Val Ser Gln Leu Leu Cys Leu
225                 230                 235                 240

Arg Glu Gly Asn Gln Lys Val Glu Arg Leu Glu Val Ala Leu Lys Glu
            245                 250                 255

Ala Lys Glu Arg Val Ser Asp Phe Glu Lys Lys Thr Ser Asn Arg Ser
            260                 265                 270

Glu Ile Glu Thr Gln Thr Glu Gly Ser Thr Glu Lys Glu Asn Asp Glu
            275                 280                 285

Glu Lys Gly Pro Glu Thr Val Gly Ser Glu Val Glu Ala Leu Asn Leu
            290                 295                 300

Gln Val Thr Ser Leu Phe Lys Glu Leu Gln Glu Ala His Thr Lys Leu
305                 310                 315                 320

Ser Glu Ala Glu Leu Met Lys Lys Arg Leu Gln Glu Lys Cys Gln Ala
            325                 330                 335

Leu Glu Arg Lys Asn Ser Ala Ile Pro Ser Glu Leu Asn Glu Lys Gln
            340                 345                 350

Glu Leu Val Tyr Pro Asn Lys Lys Leu Glu Leu Gln Val Glu Ser Met
            355                 360                 365

Leu Ser Glu Ile Lys Met Glu Gln Ala Lys Thr Glu Asp Gly Lys Ser
370                 375                 380

Lys Leu Thr Val Leu Gln Met Thr His Asn Lys Leu Leu Gln Glu His
385                 390                 395                 400

Asn Asn Ala Leu Lys Thr Ile Glu Glu Leu Thr Arg Lys Glu Ser Glu
                405                 410                 415

Lys Val Asp Arg Ala Val Leu Lys Glu Leu Ser Glu Lys Leu Glu Leu
            420                 425                 430

Ala Glu Lys Ala Leu Ala Ser Lys Gln Leu Gln Met Asp Glu Met Lys
            435                 440                 445

Gln Thr Ile Ala Lys Gln Glu Glu Asp Leu Glu Thr Met Thr Ile Leu
            450                 455                 460

Arg Ala Gln Met Glu Val Tyr Cys Ser Asp Phe His Ala Glu Arg Ala
465                 470                 475                 480

Ala Arg Glu Lys Ile His Glu Glu Lys Glu Gln Leu Ala Leu Gln Leu
            485                 490                 495

Ala Val Leu Leu Lys Glu Asn Asp Ala Phe Glu Asp Gly Gly Arg Gln
            500                 505                 510

Ser Leu Met Glu Met Gln Ser Arg His Gly Ala Arg Thr Ser Asp Ser
            515                 520                 525

Asp Gln Gln Ala Tyr Leu Val Gln Arg Gly Ala Glu Asp Arg Asp Trp
            530                 535                 540
```

```
-continued

Arg Gln Gln Arg Asn Ile Pro Ile His Ser Cys Pro Lys Gly Glu Val
545             550             555             560

Leu Pro Asp Ile Asp Thr Leu Gln Ile His Val Met Asp Cys Ile Ile
            565             570             575
```

MODULATORS OF THE FUNCTION OF RECEPTORS OF THE TNF/NGF RECEPTOR

CROSS REFERENCE TO RELATED APPLICATION

The present application is the national stage under 35 U.S.C. 371 of PCT/IL99/00158, filed Mar. 18, 1999.

1. Field of the Invention

The present invention is generally in the field of receptors belonging to the TNF/NGF superfamily of receptors and the control of their biological functions. The TNF/NGF superfamily of receptors includes receptors such as the p55 and p75 tumor necrosis factor receptors (TNF-Rs, hereinafter called p55-R and p75-R) and the FAS ligand receptor (also called FAS/APO1 or FAS-R and hereinafter will be called FAS-R) and others. Specifically, the present invention concerns novel proteins which bind to other proteins which themselves bind directly or indirectly to members of the TNF/NGF receptor family and other intracellular modulatory proteins.

More specifically, it relates to one such protein, herein designated RAP-2 (for RIP-associated protein-2), and its isoforms, fragments, derivatives, and as well as to proteins binding to RAP-2.

RAP-2 binds to RIP ("receptor interacting protein") and is capable of modulating or mediating the function of RIP and thereby also capable of modulating or mediating, directly or indirectly, the function of other proteins which bind to RIP directly or indirectly. RAP-2 binding proteins are modulators/mediators of RAP-2 function.

2. Background of the Related Art

Tumor Necrosis Factor (TNF-α) and Lymphotoxin (TNF-β) (hereinafter, TNF, refers to both TNF-α and TNF-β) are multifunctional pro-inflammatory cytokines formed mainly by mononuclear phagocytes, which have many effects on cells (Wallach, D. (1986) In: Interferon 7 (Ion Gresser, ed.), pp. 83–122, Academic Press, London; and Beutler and Cerami (1987). Both TNF-α and TNF-β initiate their effects by binding to specific cell surface receptors. Some of the effects are likely to be beneficial to the organism: they may destroy, for example, tumor cells or virus infected cells and augment antibacterial activities of granulocytes. In this way, ELF contributes to the defense of the organism against tumors and infectious agents and contributes to the recovery from injury. Thus, TNF can be used as an anti-tumor agent in which application it binds to its receptors on the surface of tumor cells and thereby initiates the events leading to the death of the tumor cells. TNF can also be used as an anti-infectious agent.

However, both TNF-α and TNF-β also have deleterious effects. There is evidence that overproduction of TNF-α can play a major pathogenic role in several diseases. For example, effects of TNF-α, primarily on the vasculature, are known to be a major cause for symptoms of septic shock (Tracey et al., 1986). In some diseases, TNF may cause excessive loss of weight (cachexia) by suppressing activities of adipocytes and by causing anorexia, and TNF-α was thus called cachetin. It was also described as a mediator of the damage to tissues in rheumatic diseases (Beutler and Cerami, 1987) and as a major mediator of the damage observed in graft-versus-host reactions (Piquet et al., 1987). In addition, TNF is known to be involved in the process of inflammation and in many other diseases.

Two distinct, independently expressed, receptors, the p55 and p75 TNF-Rs, which bind both TNF-α and TNF-β specifically, initiate and/or mediate the above noted biological effects of TNF. These two receptors have structurally dissimilar intracellular domains suggesting that they signal differently (See Hohmann et al., 1989; Engelmann et al., 1990; Brockhaus et al., 1990; Leotscher et al., 1990; Schall et al., 1990; Nophar et al., 1990; Smith et al., 1990; and Heller et al., 1990). However, the cellular mechanisms, for example, the various proteins and possibly other factors, which are involved in the intracellular signaling of the p55 and p75 TNF-Rs have yet to be elucidated. It is this intracellular signaling, which occurs usually after the binding of the ligand, i.e., TNF (α or β), to the receptor, that is responsible for the commencement of the cascade of reactions that ultimately result in the observed response of the cell to TNF.

As regards the above-mentioned cytocidal effect of TNF, in most cells studied so far, this effect is triggered mainly by the p55 TNF-R. Antibodies against the extracellular domain (ligand binding domain) of the p55 TNF-R can themselves trigger the cytocidal effect (see EP 412486) which correlates with the effectivity of receptor cross-linking by the antibodies, believed to be the first step in the generation of the intracellular signaling process. Further, mutational studies (Brakebusch et al., 1992; Tartaglia et al., 1993) have shown that the biological function of the p55 TNF-R depends on the integrity of its intracellular domain. Accordingly it has been suggested that the initiation of intracellular signaling leading to the cytocidal effect of TNF occurs as a consequence of the association of two or more intracellular domains of the p55 TNF-R. Moreover, TNF (α and β) occurs as a homotrimer, and as such, has been suggested to induce intracellular signaling via the p55 TNF-R by way of its ability to bind to and to cross-link the receptor molecules, i.e., cause receptor aggregation.

Another member of the TNF/NGF superfamily of receptors is the FAS receptor (FAS-R) which has also been called the FAS antigen, a cell-surface protein expressed in various tissues and sharing homology with a number of cell-surface receptors including TNF-R and NGF-R. The FAS-R mediates cell death in the form of apoptosis (Itoh et al., 1991), and appears to serve as a negative selector of autoreactive T cells, i.e., during maturation of T cells, FAS-R mediates the apoptopic death of T cells recognizing self-antigens. It has also been found that mutations in the FAS-R gene (lpr) cause a lymphoproliferation disorder in mice that resembles the human autoimmune disease systemic lupus erythematosus (SLE) (Watanabe-Fukunaga et al., 1992). The ligand for the FAS-R appears to be a cell-surface associated molecule carried by, amongst others, killer T cells (or cytotoxic T lymphocytes—CTLs), and hence when such CTLs contact cells carrying FAS-R, they are capable of inducing apoptopic cell death of the FAS-R-carrying cells. Further, monoclonal antibodies have been prepared that are specific for FAS-R, these monoclonal antibodies being capable of inducing apoptopic cell death in cells carrying FAS-R, including mouse cells transformed by cDNA encoding human FAS-R (Itoh et al., 1991).

A number of approaches have been made by the applicants (see for example, European Application Nos. EP 186833, EP 308378, EP 398327 and EP 412486) to regulate the deleterious effects of TNF by inhibiting the binding of TNF to its receptors using anti-TNF antibodies or by using soluble TNF receptors to compete with the binding of TNF to the cell surface-bound TNF-Rs. Further, on the basis that TNF-binding to its receptors is required for the TNF-induced cellular effects, approaches by applicants (see for example EP 568925) have been made to modulate the TNF effect by modulating the activity of the TNF-Rs.

Briefly, EP 568925 relates to a method of modulating signal transduction and/or cleavage in TNF-Rs whereby peptides or other molecules may interact either with the receptor itself or with effector proteins interacting with the receptor, thus modulating the normal function of the TNF-Rs. In EP 568925, there is described the construction and characterization of various mutant p55 TNF-Rs, having mutations in the extracellular, transmembrane, and intracellular domains of the p55 TNF-R. In this way, regions within the above domains of the p55 TNF-R were identified as being essential to the functioning of the receptor, i.e., the binding of the ligand (TNF) and the subsequent signal transduction and intracellular signaling which ultimately results in the observed TNF-effect on the cells. Further, there is also described a number of approaches to isolate and identify proteins, peptides or other factors which are capable of binding to the various regions in the above domains of the TNF-R, which proteins, peptides and other factors may be involved in regulating or modulating the activity of the TNF-R. A number of approaches for isolating and cloning the DNA sequences encoding such proteins and peptides; for constructing expression vectors for the production of these proteins and peptides; and for the preparation of antibodies or fragments thereof which interact with the TNF-R or with the above proteins and peptides that bind various regions of the TNF-R., are also set forth in EP 568925. However, EP 568925 does not specify the actual proteins and peptides which bind to the intracellular domains of the TNF-Rs (e.g., p55 TNF-R), nor does it describe the yeast two-hybrid approach to isolate and identify such proteins or peptides which bind to the intracellular domains of TNF-Rs. Similarly, in EP 568925 there is no disclosure of proteins or peptides capable of binding the intracellular domain of FAS-R.

While it is known that the tumor necrosis factor (TNF) receptors, and the structurally-related receptor FAS-R, trigger in cells, upon stimulation by leukocyte-produced ligands, destructive activities that lead to their own demise, the mechanisms of this triggering are still little understood. Mutational studies indicate that in FAS-R and the p55 TNF receptor (p55-R) signaling for cytotoxicity involve distinct regions within their intracellular domains (Brakebusch et al., 1992; Tartaglia et al., 1993; Itoh and Nagata, 1993). These regions (the 'death domains') have sequence similarity. The 'death domains' of both FAS-R and p55-R tend to self-associate. Their self-association apparently promotes that receptor aggregation which is necessary for initiation of signaling (see Song et al., 1994; Wallach et al., 1994; Boldin et al., 1995), and at high levels of receptor expression can result in triggering of ligand-independent signaling (Boldin et al., 1995).

Like other receptor-induced effects, cell death induction by the TNF receptors and FAS-R occurs via a series of protein-protein interactions, leading from ligand-receptor binding to the eventual activation of enzymatic effector functions, which in the case studies have elucidated non-enzymatic protein-protein interactions that initiate signaling for cell death: binding of trimeric TNF or the FAS-R ligand molecules to the receptors, the resulting interactions of their intracellular domains (Brakebusch et al., 1992; Tartaglia et al., 1993; Itoh and Nagata, 1993) augmented by a propensity of the death-domain motifs to self-associate (Boldin et al., 1995a), and induced binding of two cytoplasmic proteins (which can also bind to each other) to the receptors' intracellular domains—MORT-1 (or FADD) to FAS-R (Boldin et al., 1995b; Chinnaiyan et al., 1995; Kischkel et al., 1995) and TRADD to p55-R (Hsu et al., 1995; Hsu et al., 1996).

Three proteins that bind to the intracellular domain of FAS-R and p55-R at the 'death domain' region involved in cell-death induction by the receptors through hetero-association of homologous regions and that independently are also capable of triggering cell death were identified by the yeast two-hybrid screening procedure. One of these is the protein, MORT-1 (Boldin et al. 1995b), also known as FADD (Chinnaiyan et al., 1995) that binds specifically to FAS-R. The second one, TRADD (see also Hsu et al., 1995, 1996), binds to p55-R, and the third, RIP (see also Stanger et al., 1995), binds to both FAS-R and p55-R. Besides their binding to FAS-R and p55-R, these proteins are also capable of binding to each other, which provides for a functional "cross-talk" between FAS-R and p55-R. These bindings occur through a conserved sequence motif, the 'death domain module' common to the receptors and their associated proteins. Furthermore, although in the yeast two-hybrid test MORT-1 was shown to bind spontaneously to FAS-R, in mammalian cells, this binding takes place only after stimulation of the receptor, suggesting that MORT-1 participates in the initiating events of FAS-R signaling. MORT-1 does not contain any sequence motif characteristic of enzymatic activity, and therefore, its ability to trigger cell death does not seem to involve an intrinsic activity of MORT-1 itself, but rather, activation of some other protein(s) that bind MORT-1 and act further downstream in the signaling cascade. Cellular expression of MORT-1 mutants lacking the N-terminal part of the molecule has been shown to block cytotoxicity induction by FAS/APO1 (FAS-R) or p55-R (Hsu et al., 1996; Chinnaiyan et al., 1996), indicating that this N-terminal region transmits the signaling for the cytocidal effect of both receptors through protein-protein interactions.

Thus, the 'death domain' motifs of the receptors p55-R and FAS-R as well as their three associated proteins MORT-1, RIP and TRADD appear to be the sites of protein-protein interactions. The three proteins MORT-1, RIP and TRADD interact with the p55-R and FAS-R intracellular domains by the binding of their death domains to those of the receptors, and for both RIP and TRADD their death domains also self-associate, (although MORT-1 differs in this respect in that its death domain does not self-associate). Further, MORT-1 and TRADD bind differentially to FAS-R and p55-R and also bind to each other. Moreover, both MORT-1 and TRADD bind effectively to RIP. Accordingly, it would seem that the interaction between the three proteins MORT-1, RIP and TRADD is an important part of the overall modulation of the intracellular signaling mediated by these proteins. Interference of the interaction between these three intracellular proteins will result in modulation of the effects caused by this interaction. For example, inhibition of TRADD binding to MORT-1 may modulate the FAS-R-p55 TNF-R interaction. Likewise, inhibition of RIP in addition to the above inhibition of TRADD binding to MORT-1 may further modulate FAS-R-p55 TNF-R interaction.

Monoclonal antibodies raised against the 'death domain' of p55-R, specifically against the binding site of sites of TRADD and RIP can also be used to inhibit or prevent binding of these proteins and thus cause modulation of the interaction between FAS-R and p55-R.

It has also recently been found that besides the above noted cell cytotoxicity activities and modulation thereof mediated by the various receptors and their binding proteins including FAS-R, p55-R, MORT-1, TRADD, RIP, MACH, Mch4, and G1, a number of these receptors and their binding proteins are also involved in the modulation of the activity of the nuclear transcription factor NF-κB, which is a key mediator of cell survival or viability, being responsible for the control of expression of many immune- and inflammatory-response genes. For example, it has been found that TNF-α can actually stimulate activation of NF-κB and thus TNF-α is capable of inducing two kinds of signal in cells, one eliciting cell death and another that protects cells against death induction by inducing gene expression via NF-κB (see Beg and Baltimore, 1996; Wang et al., 1996; Van Antwerp et al., 1996). A similar dual effect for FAS-R has also been reported (see reference to this effect as stated in above Van Antwerp et al., 1996). It would therefore appear that there exists a delicate balance between cell death and cell survival upon stimulation of various types of cells with TNF-α and/or the FAS-R ligand, the ultimate outcome of the stimulation depending on which intracellular pathway is stimulated to a greater extent, the one leading to cell death (usually by apoptosis), or the one leading to cell survival via activation of NF-κB.

In addition, the present inventors have also recently further elucidated the possibly pathway by which members of the TNF/NGF receptor family activate NF-κB (see Malinin et al., 1997 and the various relevant references set forth therein; and co-owned, co-pending Israel Patent Application Nos. IL 117800 and IL 119133). Briefly, it arises that several members of the TNF/NGF receptor family are capable of activating NF-κB through a common adaptor protein, TRAF2. A newly elucidated protein kinase called NIK (see above Malinin et al., 1997 and IL 117800 and IL 119133) is capable of binding to TRAF2 and of stimulating NF-κB activity. In fact, it was shown (see aforesaid Malinin et al. and IL applications) that expression in cells of kinase-deficient NIK mutants results in the cells being incapable of having stimulation of NF-κB in a normal endogenous manner and also in the cell having a block in induction of NF-κB activity by TNF, via either FAS-R, and a block in NF-κB induction by TRADD, RIP and MORT-1 (which are adaptor proteins that bind these p55-R and/or FAS-R receptors). All of the receptors p55-R, p75-R, FAS-R and their adaptor proteins MORT-1, TRADD and RIP bind directly or indirectly to TRAF2, which by its binding ability to NIK apparently modulates the induction of NF-κB.

Of the above modulator proteins involved in the fine balance between cell death and survival following stimulation of FAS-R and/or p55-R, the protein RIP appears to have an important role. RIP (see Stanger et al., 1995 and also Malinin et al., 1997) has a 'death domain' in its C-terminal region which enables it to induce cell cytotoxicity in an independent way and also by association with the death domains of MORT-1, p55-R, FAS-R and TRADD. RIP also has a protein kinase domain at its N-terminal region and an intermediate domain which is believed to enable its intersection (binding) with TRAF2 and thereby its involvement in NF-κB induction. Accordingly, details concerning the characteristics and sequences (DNA and amino acid) of RIP are set forth in the above noted publications (in particular, Stanger et al., 1995) which are incorporated herein in their entirety by reference.

TNF is also one of the cytokines involved in initiation and modulation of the host anti-viral defense. Similarly, viruses have evolved to express genes whose proteins regulate activity of the cytokines, and these cytokine-regulatory viral proteins are thought to promote persistence of the virus within the animal host. One of the best-studied examples of such a protein is E3-14.7K from the group C human adenoviruses (Ad) of types 2 and 5 which acts as a strong antagonist of TNF-mediated cytolysis.

With the aim of isolating molecular components of the TNF signaling cascade that become targets for E3-14.7K upon viral infection, a human E3-14.7K binding protein was recently isolated by two hybrid screening (FIP-2 for Fourteen-K Interacting Protein, Li. Y. et al. 1998). FIP-2 was found to be non-toxic on its own, and to reverse the protective effect of E3-14.7K on cytotoxicity, induced by over-expression of TNFR-1 or RIP, without binding to either of the two above-mentioned proteins. FIP-2 was found to have some homology to RAP-2, the protein of the present invention. The degree of overall similarity between RAP-2 and FIP-2 nevertheless is fairly low, as can be seen from the global alignment of the two amino acid sequences (FIG. 3). The homology however becomes more significant in specific regions towards the C-terminus of the proteins, culminating in virtual identity of the 30 C-terminal amino acids. It is noteworthy that, besides the abovementioned C-terminal domain, the putative Leucine Zipper motif in FIP-2 is largely preserved in RAP-2 (except for an Ile to Ala substitution).

A similar sequence named HYPL—encoding a protein related to Huntington's disease that appears to be a distant homolog of RAP-2 was recently submitted in GenBank under the title "huntingtin interacting protein, HYPL" (accession number AF049614). However, a publication describing the function of the protein not yet been published A recent publication by Yamaoka S. et al. (1998), reports the identification of a murine RAP-2 homolog. The murine homolog NEMO (for NF-κB Essential Modulator) was identified in a search for the key molecules that regulate the activation of NF-κB signaling. A flat cellular variant of HTLV-I Tax-transformed rat fibroblasts was characterized, denominated 5R, which was unresponsive to all tested NF-κB-activating stimuli (LPS, PMA, IL-I, TNF), and performed its genetic complementation. As a result of this procedure, a cDNA encoding the NEMO 48 kD protein was recovered. Based on this data, this protein is said to be absent from 5R cells, is part of the high molecular weight Iκ B-kinase complex, and is requested for its formation. In vitro, NEMO can homo-dimerize and directly interacts with IKKβ.

Israel patent specification No. 120485 discloses a RIP-associated protein, termed RAP, which specifically binds to RIP and inhibits NF-κB induction.

Israel patent specificaion No. 123758 and this application relate to another RIP-associated protein termed RAP-2, which has the same or similar activities.

RAP-2 according to the invention is also called 303 or RAP-303 or RAT-303. For consistency's sake, it will be called RAP-2 herein.

SUMMARY OF THE INVENTION

It is an object of the invention to provide a novel protein RAP-2, including all isoforms, analogs, fragments or derivatives thereof, capable of binding to the RIP protein (herein after 'RIP'). As RIP is capable of interacting directly or indirectly with the intracellular mediators of inflammation, cell cytotoxicity/cell death, such as p55-R and FAS-R and their associated adaptor or modulator proteins such as, for example, MORT-1, TRADD, MACH, Mch4, G1 and others, the novel proteins of the present invention by binding to RIP are therefore capable of affecting the intracellular signaling process initiated by the binding of the FAS ligand to its receptor, and TNF to its receptor (p55-R), and as such the new proteins of the present invention are modulators of the p55-R and FAS-R-mediated effect on cells. RIP is also capable of interacting with TRAF2 and thereby is capable of interacting directly or indirectly with NIK and as such RIP acts as a modulator of inflammation and of cell survival pathways involving NF-κB induction, thus the new proteins of the present invention are modulators of RIP-related inflammation and cell survival activity. Likewise, by way of the FAS-R, p55-R and their modulator proteins MORT-1 and TRADD being capable of inducing NF-κB and cell survival either directly or indirectly by binding to RIP or by binding to TRAF2, to which RIP binds, the proteins of the present invention may also be mediators of cell survival processes by way of operating via common or related intracellular signaling pathways in which the various above proteins operate to induce cell survival. Similarly, as p75-R binds to TRAF2 to which RIP binds, the novel proteins of the invention may also be modulators of RIP-related mediation of p75-R mediated activity.

Another object of the invention is to provide antagonists (e.g., antibodies, peptides, organic compounds, or even some isoforms) to the above novel RAP-2 proteins, isoforms, analogs, fragments and derivatives thereof, which may be used to inhibit the signaling process, or, more specifically, the inflammation cell-cytotoxicity, or cell-survival processes, when desired.

A further object of the invention is to use the above novel RAP-2 proteins, isoforms, analogs, fragments and derivatives thereof, to isolate and characterize additional proteins or factors, which may be involved in regulation of receptor activity, e.g., other proteins which may bind to RAP-2 proteins and influence their activity, and/or to isolate and identify other receptors further upstream or downstream in the signaling process(es) to which these novel proteins, analogs, fragments and derivatives bind, and hence, in whose function they are also involved.

The invention this also provides RAP-2 binding proteins which are capable of modulating/mediating RAP-2 function.

A still further object of the invention is to provide inhibitors which can be introduced into cells to bind or interact with RAP-2 and possible RAP-2 isoforms which inhibitors may act to inhibit RIP-associated activity in cell cytotoxic processes and hence, when desired, to enhance cell survival, or which may act to inhibit RIP-associated activity in cell-survival processes and hence, when desired, to enhance cell cytotoxicity.

Moreover, it is an object of the present invention to use the above-mentioned novel RAP-2 proteins, isoforms and analogs, fragments and derivatives thereof as antigens for the preparation of polyclonal and/or monoclonal antibodies thereto. The antibodies, in turn, may be used, for example, for the purification of the new proteins from different sources, such as cell extracts or transformed cell lines.

Furthermore, these antibodies may be used for diagnostic purposes, e.g., for identifying disorders related to abnormal functioning of cellular effects mediated by the p55-R, FAS-R or other related receptors.

A further object of the invention is to provide pharmaceutical compositions comprising the above novel RAP-2 proteins, isoforms, or analogs, fragments or derivatives thereof, as well as pharmaceutical compositions comprising the above noted antibodies or other antagonists.

In accordance with the present invention, a novel protein RAP-2 has been isolated. RAP-2 is capable of binding to, or interacting with, RIP, and hence is a modulator or mediator of RIP intracellular activity. RIP is involved in the modulation or mediation of intracellular signaling pathways, e.g. the cell cytotoxicity or cell death associated pathway in which RIP has cytotoxic activity by itself and in association, directly or indirectly, with a number of other cell-death associated proteins, such as, for example, MORT-1, TRADD, MACH, Mch4, G1, p55-R and FAS-R, with which RIP can associate or bind to in a direct or indirect fashion via the 'death domain' motif/module present in RIP and in all the aforesaid proteins; another pathway being the inflammation, cell survival or viability pathway in which RIP may have an activation role, directly or indirectly by virtue of the presence of a kinase motif or domain present in RIP and RIP's ability to be capable of binding to TRAF2 which can bind NIK which, in turn, is directly involved in activation of NF-κB which plays a central role in inflammation and cell survival. Further, p55-R is also capable of interaction with TRADD and TRAF2 (via TRADD) and is also implicated in NF-κB activation and thereby in the cell survival pathway, and hence RIP by being capable of binding to or interacting with, FAS-R, TRADD and p55-R (via TRADD) as well as with TRAF2 may also be implicated in the modulation of inflammation, cell survival activation by these proteins. Accordingly, RIP is a modulator or mediatior of these pathways, and likewise, the new RAP-2 of the present invention by binding to RIP is a modulator or mediator of these intracellular pathways.

RAP-2 has been isolated and cloned using the yeast two-hybrid system, sequenced and characterized, and as is detailed herein below, RAP-2 appears to be a highly specific RIP-binding protein and hence a specific RIP modulator/mediator. RAP-2 does not bind to TRADD, MORT-1, p55-R, p75-R and MACH. Further, it appears that RAP-2 does not have a characteristic death domain module or motif, this being consistent with the finding that RAP-2 does not induce cell cytotoxicity on its own.

As will be used herein throughout, RIP activity is meant to include its activity in modulation/mediation in the inflammation and cell death/survival pathways. These activities are indicated hereinabove and hereinbelow as well as in all the above-mentioned publications and patent applications, the full contents of which are incoroporated herein by reference. Likewise, as used herein throughout RAP-2 activity is meant to include its modulation/mediation of RIP activity by virtue of its specific binding to RIP, this modulation/mediation of RIP by RAP-2 including modulation/mediation of the inflammation, cell death and cell survival pathways in which RIP is involved directly or indirectly, and as such RAP-2 may be considered as an indirect modulator/mediator of all the above mentioned proteins and possibly a number of others which are involved in inflammation, cell death or cell survival and to which RIP binds, or with which RIP interacts in a direct or indirect fashion.

This invention also discloses two novel RAP-2 binding proteins, identified by two hybrid screening using the full length RAP-2 protein sequence as bait.

Applying the full-length RAP-2 protein as bait in two-hybrid screen a novel RAP-2-interacting protein denoted hereabove or hereafter clone #10 (or clone #10-encoded protein or RAT-binding protein #10 or RBP-10). The sequence of the cDNA obtained was further extended by common sequencing methods known in the art towards the 5' end, to reconstitute a partial open reading frame of the protein which however lacks a start codon.

Two-hybrid assay of the binding repertoire of clone #10 revealed that this protein, not only binds RAP-2, but exhibits also a rather strong affinity to TRAF2. Clone #10 however does not bind to RIP, TRADD, MORT1, MACH, TNFR-1, TIP60 and NIK as well as to several control proteins (for example lamin and cyclinD). It cannot however be excluded that binding of clone #10 to NIK might be found in mammalian cells, considering the peculiarities of NIK's behaviour in yeast. Clone #10 was shown to bind RAP-2 within the C-terminal 200 a.a. of the latter, i.e. a region not necessarily associated with the binding of RIP, TIP60, NIK and IKKβ. This sequence, however inaccurate, enabled us to carry out several rounds of GenBank searches aiming at identification of homologues of clone #10. The only protein that exhibited a substantial degree of similarity to the protein encoded by Clone #10 was F40F12.5—a hypotetical molecule from *C.Elegans*, to which no physiological role is assigned.

Interestingly, F40F12.5 was found to display some similarity to several members of the widely conserved family of ubiquitin-directed proteases. These enzymes counterbalance the destructive effect of the ubiquitination machinery, which is known to be in charge of the majority of protein degradation events in a cell. While ubiquitin ligases are responsible for attaching the poly-ubiquitin tree to a protein predestiied for degradation, ubiquitin proteases prevent an effective branching of the growing tree. Such presumption regarding the function of F40F12.5 based on the similarity to the abovementioned ubiquitin-directed proteases however is questionable, as it has not yet been examined whether this particular protein posesses any enzymatic activity toward ubiquitin polymers. Furthermore a couple of points make such a coincidence quite unlikely:

a) Residues which are believed to constitute the core catalytic region in either subclass of ubiquitin proteases are not conserved in either F40F12.5, or in Clone #10;

b) Except from their catalytic sites, enzymes of the ubiquitin-directed protease family derived from various species (from bacteria to human) display virtually no sequence similarity while F40F12.5 and clone #10 dispaly a certain degree of homology.

It thus appears that RAP-2 is a specific RIP-binding protein and hence a modulator/mediator of RIP intracellular activity. The RAP-2 binding proteins, by their ability to bind RAP-2, have indirect influence on RIP and are thus also modulators/mediators of RIP intracellular activity.

Thus, as RAP-2 apparently has a role in modulating/mediating inflammation, cell survival and/or cell death activities in which RIP is involved directly or indirectly, especially those related to cytotoxicity and inflammation caused or induced by various stimuli including those transmitted via receptors of the TNF/NGF receptor family and possibly others as well. (For a scheme of RIP's involvement in these intracellular events and hence RAP-2's involvement, see FIG. 1 in Malinin et al., 1997).

RAP-2 may also serve as an inhibitor of cell cytotoxicity and inflammation by virtue of its being present as part of a complex of other proteins, e.g. RIP and proteins bound to RIP, and as such may affect the cytotoxicity or inflammatory effects of these other proteins (e.g. p55-R, FAS-R, MACH, Mch4, G1 and MORT-1), ultimately resulting in an inhibition of their cytotoxic activity or their activity in inflammation.

RAP-2 may yet also serve as an enhancer or augmentor of cell cytotoxicity and inflammation and thus by augmenting the activity of other proteins, e.g. RIP and other proteins bound to RIP as noted above aiding in the recruitment of these proteins by RIP, the recruitment serving to augment the cytotoxic activity of the various proteins or to augment their inflammatory effects.

Likewise, in an analogous fashion RAP-2 may also serve as an inhibitor or an augmentor of the cell-survival pathway as noted above by virtue of RIP's involvement in this pathway.

Accordingly, the present invention provides a DNA sequence encoding a RIP-associated protein (RAP-2), isoforms, analogs or fragments thereof, capable of binding to RIP and modulating or mediating the intracellular activity of RIP, said intracellular activity being a modulation/mediation of inflammation and/or cell death and/or cell survival.

In particular, the present invention provides a DNA sequence selected from the group consisting of:

(a) a cDNA sequence derived from the coding region of a native RAP-2 protein;

(b) DNA sequences capable of hybridization to a sequence of (a) under moderately stringent conditions and which encode a biologically active RAP-2 protein; and (c) DNA sequences which are degenerate as a result of the genetic code to the DNA sequences defined in (a) and (b) and which encode a biologically active RAP-2 protein.

Another specific embodiment of the above DNA sequence of the invention is a DNA sequence comprising at least part of the sequence encoding at least one isoform of the RAP-2 protein. Another embodiment of the above DNA sequence is the sequence encoding the RAP-2 protein as depicted in FIG. 1. Yet another embodiment is the DNA sequence shown in FIG. 2.

The present invention provides RAP-2 proteins, and analogs, fragments or derivatives thereof encoded by any of the above sequences of the invention, said proteins, analogs, fragments and derivatives being capable of binding to RIP and modulating/mediating its biological activity in cell death and/or cell survival pathways intracellularly.

A specific embodiment of the invention is the RAP-2 protein, analogs, fragments and derivatives thereof. The RAP-2 protein sequence as deduced from the DNA sequences of FIGS. 1 and 2 is shown in FIG. 3. Another embodiment is any isoform of the RAP-2 protein, analogs, fragments and derivatives thereof.

Also provided by the present invention are replicable expression vehicles comprising the above DNA, these replicable expression vehicles being capable of being expressed in suitable eukaryotic or prokaryotic host cells; transformed eukaryotic or prokaryotic host cells containing such replicable expression vehicles; and a method for producing the RAP-2 protein, or analogs, fragments or derivatives of the invention by growing such transformed host cells under conditions suitable for the expression of said protein, analogs, fragments or derivatives, effecting post-translational modifications of said protein as necessary for obtaining said protein and extracting said expressed protein, analogs, fragments or derivatives from the culture medium of said transformed cells or from cell extracts of said transformed cells. The above definitions are intended to include all isoforms of the RAP-2 protein.

In another aspect, the present invention also provides antibodies or active derivatives, or fragments thereof specific for the RAP-2 protein, and analogs, fragments and derivatives thereof, of the invention.

By yet another aspect of the invention, there are provided various uses of the above DNA sequences or the proteins which they encode, according to the invention, which uses include amongst others:

(i) A method for the modulation of the intracellular inflammation, cell death and/or cell survival pathways modulated or mediated by the protein RIP, comprising treating said cells with one or more RAP-2 proteins, isoforms, analogs, fragments or derivatives thereof, capable of binding to RIP wherein said treating of said cells comprises introducing into said cells said one or more proteins, isoforms, analogs, fragments or derivatives thereof in a form suitable for intracellular introduction thereof, or introducing into said cells a DNA sequence encoding said one or more proteins, isoforms, analogs, fragments or derivatives in the form of a suitable vector carrying said sequence, said vector being capable of effecting the insertion of said sequence into said cells in a way that said sequence is expressed in said cells.

(ii) A method for the modulation of the inflammation, cell death and/or cell survival pathways mediated by ligands of the TNF family by effect on cells via the action of the RIP protein, according to (i) above, wherein said treating of cells comprises introducing into said cells said RAP-2 protein, or isoforms, analogs, fragments or derivatives thereof, in a form suitable for intracellular introduction, or introducing into said cells a DNA sequence encoding said G1 protein, or isoforms, analogs, fragments or derivatives in the form of a suitable vector carrying said sequence, said vector being capable of effecting the insertion of said sequence into said cells in a way that said sequence is expressed in said cells.

(iii) A method as in (ii) above wherein said treating of said cells is by transfection of said cells with a recombinant animal virus vector comprising the steps of:
  (a) constructing a recombinant animal virus vector carrying a sequence encoding a viral surface protein (ligand) that is capable of binding to a specific cell surface receptor on the surface of a FAS-R- or p55-R-carrying cell and a second sequence encoding a protein selected from RAP-2 protein, and isoforms, analogs, fragments and derivatives thereof, that when expressed in said cells is capable of modulating/mediating the intracellular inflammation, cell death and/or cell survival pathways; and
  (b) infecting said cells with said vector of (a).

(iv) A method for modulating the inflammation, cell death and/or cell survival pathways mediated by the ligands of the TNF family effect on cells via the action of the RIP protein comprising treating said cells with antibodies or active fragments or derivatives thereof, according to the invention, said treating being by application of a suitable composition containing said antibodies, active fragments or derivatives thereof to said cells, wherein when at least part of the RAP-2 protein is exposed on the extracellular surface, said composition is formulated for extracellular application, and when said RAP-2 proteins are entirely intracellular, said composition is formulated for intracellular application.

(v) A method for modulating the inflammation, cell death and/or cell survival pathways mediated by the ligands of the TNF family effect on cells via the action of the RIP protein comprising treating said cells with an oligonucleotide sequence encoding an antisense sequence of at least part of the RAP-2 protein sequence of the invention, said oligonucleotide sequence being capable of blocking the expression of the RAP-2 protein.

(vi) A method as in (ii) above for treating tumor cells or HIV-infected cells or other diseased cells, comprising (a) constructing a recombinant animal virus vector carrying a sequence encoding a viral surface protein capable of binding to a specific tumor cell surface receptor or HIV-infected cell surface receptor or receptor carried by other diseased cells and a sequence encoding a protein selected from RAP-2 protein, analogs, fragments and derivatives of the invention, that when expressed in said tumor, HIV-infected, or other diseased cell is capable of killing said cell via the action of the RIP protein; and (b) infecting said tumor or HIV-infected cells or other diseased cells with said vector of (a).

(vii) A method for modulating the cell death and/or cell survival pathways mediated by ligands of the TNF family effect on cells via the action of the RIP protein comprising applying the ribozyme procedure in which a vector encoding a ribozyme sequence capable of interacting with a cellular mRNA sequence encoding a RAP-2 protein according to the invention, is introduced into said cells in a form that permits expression of said ribozyme sequence in said cells, and wherein when said ribozyme sequence is expressed in said cells it interacts with said cellular mRNA sequence and cleaves said mRNA sequence resulting in the inhibition of expression of said RAP-2 protein in said cells.

(viii) A method selected from the above methods according to the invention, wherein said RAP-2 protein encoding sequence comprises at least one of the RAP-2 isoforms, analogs, fragments and derivatives of any thereof according to the invention which are capable of binding to RIP.

(ix) A method for isolating and identifying proteins, according to the invention capable of binding to the RIP protein, comprising applying the yeast two-hybrid procedure in which a sequence encoding said RIP protein or is carried by one hybrid vector and sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said RIP protein.

(x) A method according to any of the (i)–(ix) above wherein said RAP-2 protein is any one of the isoforms of RAP-2, analogs, fragments and derivatives of any thereof.

(xi) A method according to any of the above (i)–(x) wherein the RAP-2 protein or any of its isoforms, analogs, fragments or derivatives is involved in the modulation of the cellular effect mediated or modulated by any other mediator or inducer to which said RAP-2 protein, isoform, analog, fragment or derivative is capable of binding directly or indirectly.

The present invention also provides a pharmaceutical composition for the modulation of inflammation, the cell death and/or cell survival pathways mediated by the TNF family effect on cells via the action of the RIP protein or the effect of any other mediator or inducer on cells as noted above, comprising, as active ingredient any one of the following (i) a RAP-2 protein according to the invention, and biologically active fragments, analogs, derivatives of mixtures thereof;

(ii) a recombinant animal virus vector encoding a protein capable of binding a cell surface receptor and encoding a RAP-2 protein or biologically active fragments or analogs, according to the invention;

(iii) an oligonucleotide sequence encoding an anti-sense sequence of the RAP-2 protein sequence according to the invention, wherein said oligonucleotide may be the second sequence of the recombinant animal virus vector of (ii) above.

The present invention also provides:

I. a method for the modulation of the inflammation, intracellular cell death and/or cell survival pathways modulated/mediated by the RIP protein, or the effect of any other mediator or inducer, or any other NF-κB inducer or inhibitor, on cells comprising treating said cells in accordance with a method of any one of (i)–(x) above, with RAP-2 proteins, isoforms, analogs, fragments or derivatives thereof or with sequences encoding RAP-2 proteins, isoforms, analogs or fragments thereof, said treatment resulting in the enhancement or inhibition of said RIP-mediated effect, and thereby also of the FAS-R or p55-R-mediated effect, or of said other mediator or inducer, or other NF-κB inducer or inhibitor.

II. a method as above wherein said RAP-2 protein, analog, fragment or derivative thereof is that part of the RAP-2 protein which is specifically involved in binding to RIP, or said other mediator or inducer, or other NF-κB inducer or inhibitor, or said RAP-2 protein sequence encodes that part of RAP-2 protein which is specifically involved in binding to RIP, or said other mediator or inducer, or other NF-κB inducer or inhibitor.

III. a method as above wherein said RAP-2 protein is any one of the RAP-2 isoforms, said isoforms capable of enhancing the RIP-associated effect.

IV. a method as above wherein said RAP-2 protein is any one of the RAP-2 isoforms, said isoforms capable of inhibiting the RIP-associated effect, or other mediator or inducer associated effect on cells and thereby also of inhibiting the FAS-R- or p55-R-associated effect on cells, or the other cytotoxic mediator or inducer effect on cells.

V. a method as above wherein said RAP-2 protein, isoform, analog, fragment or derivative capable of enhancing or inhibiting the RIP-associated effect on the inflammation and cell survival pathway by way of direct or indirect inhibition of NF-κB or direct or indirect activation of JNK or p38 kinase.

Isolation of the RAP-2 proteins, their identification and characterization may be carried out by any of the standard screening techniques used for isolating and identifying proteins, for example, the yeast two-hybrid method, affinity chromatography methods, and any of the other well-known standard procedures used for this purpose.

In yet another aspect of the invention, the RAP-2 protein itself, or an isoform, fragment or derivative thereof, is used as bait in a yeast two-hybrid screen for proteins binding thereto.

Proteins which bind to RAP-2, isoforms, fragments or derivatives thereof, are also part of the present invention.

Other aspects and embodiments of the present invention are also provided as arising from the following detailed description of the invention.

It should be noted that, where used throughout, the following terms: "Modulation/Mediation of the RIP, or FAS-ligand, or TNF effect on cells"; and any other such "Modulation/Mediation" mentioned in the specification are understood to encompass in vitro as well as in vivo treatment and, in addition, also to encompass inhibition or enhancement/augmentation.

BRIEF DESCRIPTION OF THE FIGURES

FIG. 1 (A, B) (SEQ ID NO:1) shows the nucleotide sequence of RAP-2, the start and stop codons being underlined. The arrow indicates the start of the 1.5 Kb clone obtained by two hybrid screening;

FIG. 2 (A, B) (SEQ ID NO:2) shows the nucleotide sequence of clone #41072 (see Example 1), the start and stop codons being underlined;

FIG. 3A (/1, /2) shows the deduced amino acid sequences of the human (20.4 full, SEQ ID NO:4; and Human shrt, SEQ ID NO:7) and murine (NEMO full, SEQ ID NO:5; and Mouse part, SEQ ID NO:6) splice variants of RAP-2 and B(/1, /2) shows the published sequence of FIP-2 (SEQ ID NO:8) aligned with human 20.4 (SEQ ID NO:4) using the software package available at the BCM Search Launcher (Baylor College of Medicine, Houston, Tex.). Homologous amino acids are boxed, identical amino acids are gray-shaded. Asterisks in (B) denote a putative leucine-zipper (LZ)-like motif in FIP-2.

FIG. 7 shows that RAP-2 strongly potentiates signal-induced phosphorylation of c-Jun without interfering with JNK1/2 activation level.

(A) Total cellular lysates of HEK-293T cells, transfected with the indicated expression constructs together with either pcDNA3-carrier denoted in the figure by a minus sign (−) or with pcRAP-2 denoted in the figure by a plus sign (+), were identified by Western blot analysis with anti phospho-Jun antibodies as described in Example 5. The control membrane shown on the lower panel was re-probed with anti-total-c-Jun Abs (NEB);

(B) Activated JNK1/2 from HEK-293T cells transfected with either pcDNA3 or pcRAP-2, treated with hrTNFα for increasing periods of time were detected by Western blotting of total lysates with Abs to phospho-JNK as detailed in Example 5.

(C) HEK-293T cells, co-transfected with empty vector, pcRAP-2 and pcRIP in various combinations together with HA-JNK1-expressing plasmid. JNK1 was then immunoprecipitated via its N-terminal HA-tag and its ability to phosphorylate bacterially-produced purified GST-Jun was determined in an in vitro kinase assay. Reaction products were analyzed by SDS-PAGE. GST-Jun is marked by an arrowhead.

Figure 8A:
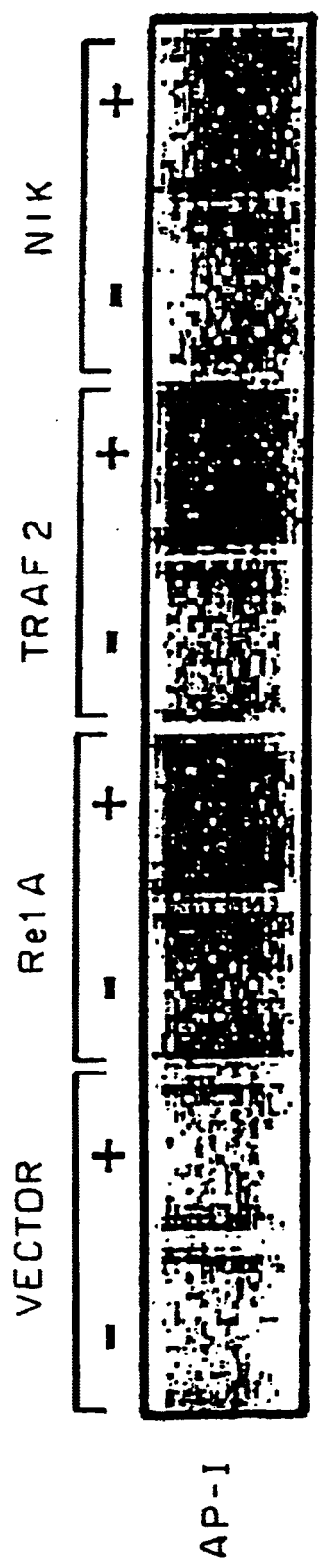
Figure 8B:
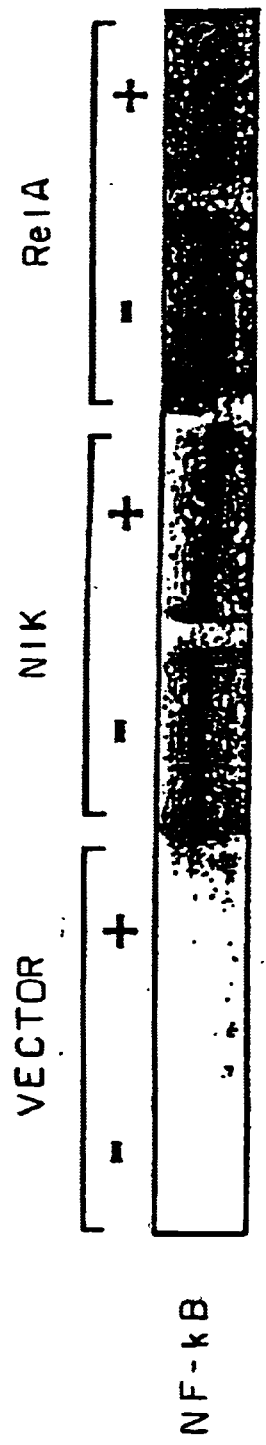

FIG. 8 shows that RAP-2 does not compete with NF-κB and AP-1 for binding to DNA. HEK-293T were transfected with the indicated proteins either alone (−) or together with pcRAP-2 (+). Nuclear extracts prepared from the cells were co-incubated with the 32P-labeled oligonucleotides comprising classical recognition sequences for AP-1(A) or NF-κB (B). Reaction products were analyzed by non-denaturing PAGE.

Figure 6B:
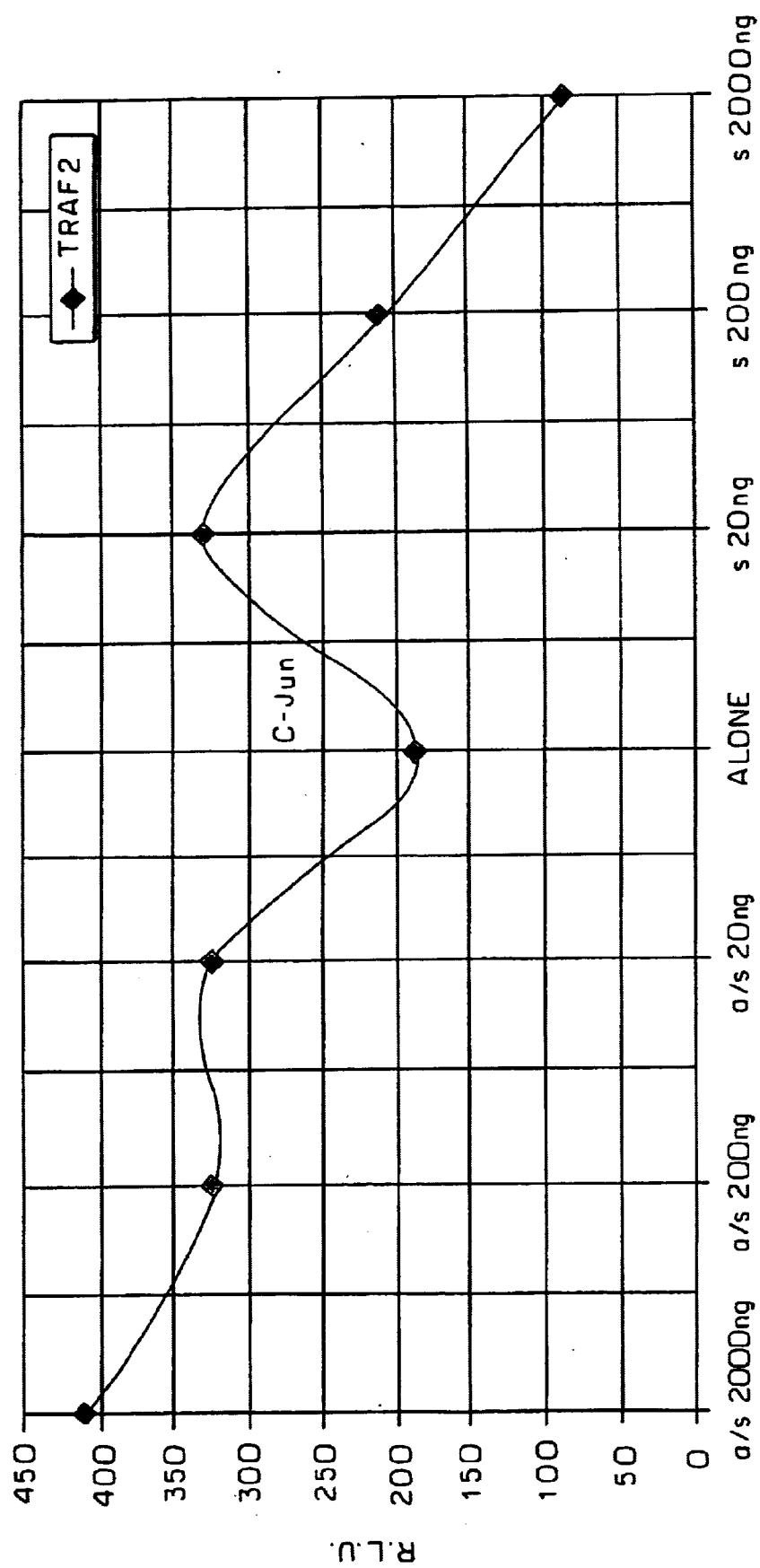
FIG. 6 shows that RAP-2 exhibits similar repressive behavior toward NF-κB and c-Jun in a wide concentration range. TRAF2 was transiently expressed in HEK-293T cells along with the various indicated amounts of either pcRAP-2 (sense) or pcRAP-2-a/s (antisense) constructs. For assessment of NF-κB (A) and c-Jun (B) activation pHIVLTR-Luc and pGAL4-Luc reporter plasmids were included respectively. Luciferase assay was performed as described for FIG. 5 in Example 4.
Figure 9A:
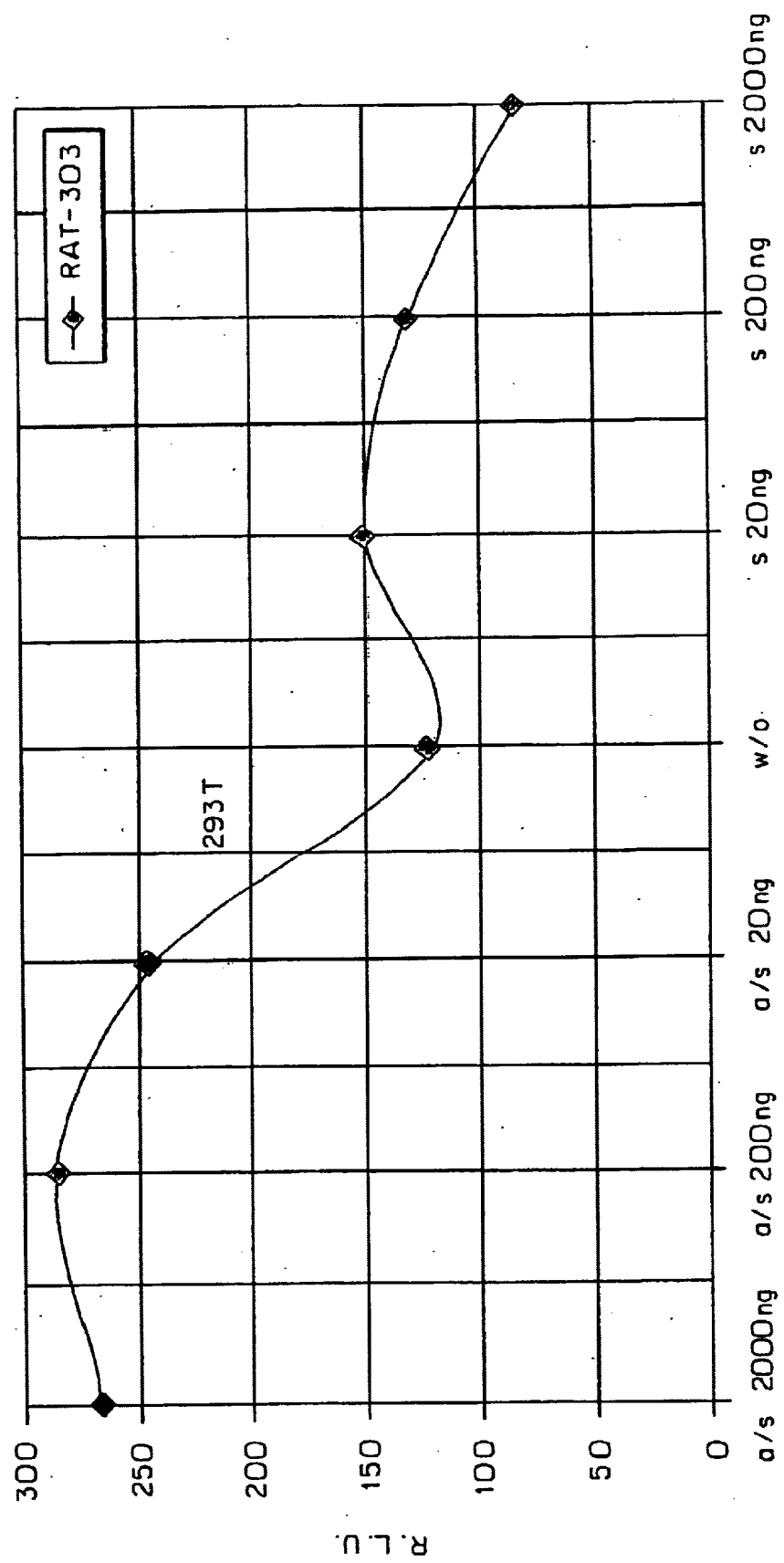
Figure 9B:
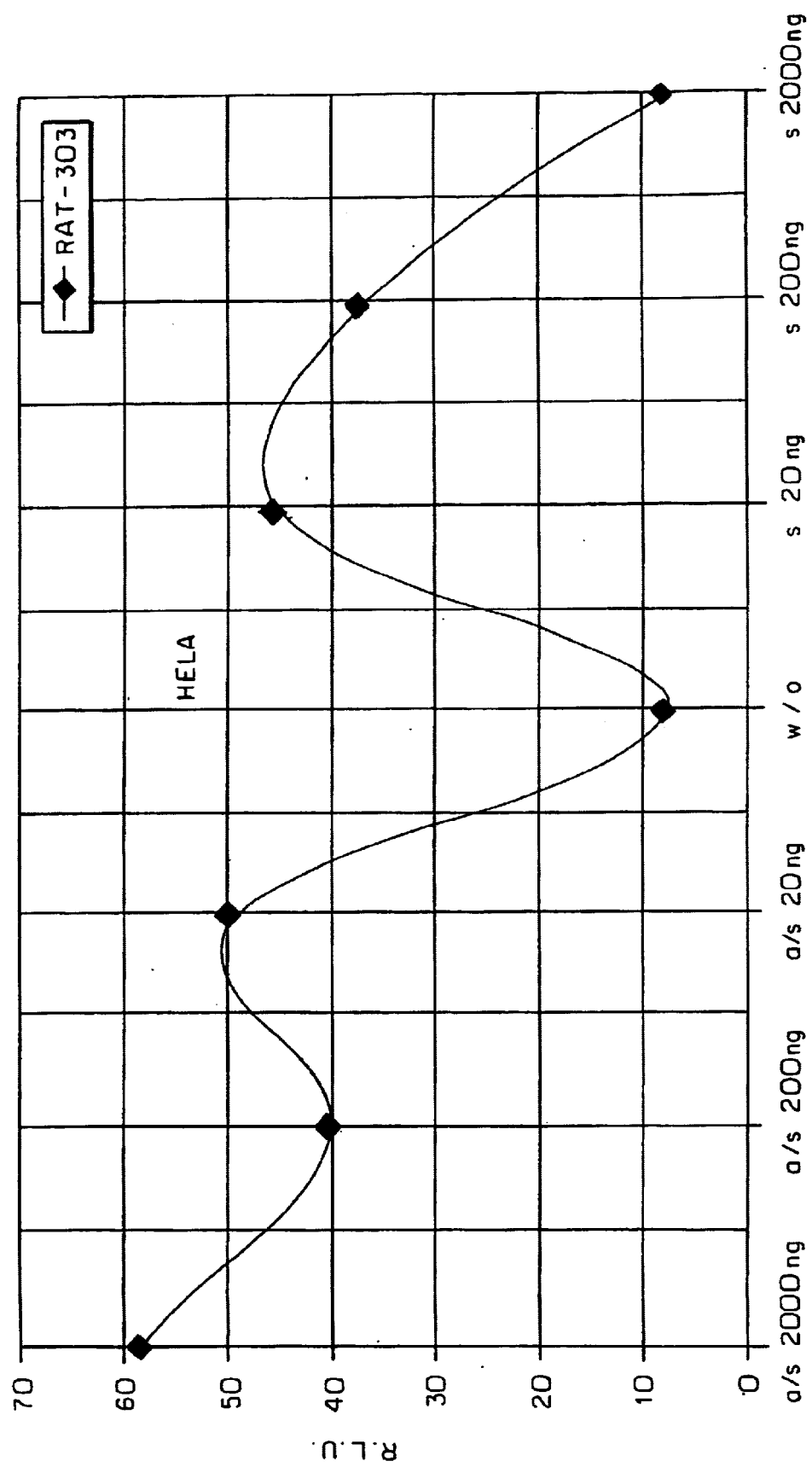

FIG. 9 shows that RAP-2 affects the basal level of NF-κB in (A) HEK-293T and (B) HeLa cells transiently transfected with variable amount of either RAP-2 (sense) or RAP-2-antisense (a/s). All manipulations were performed as described for FIG. 6 in Example 4.

FIG. 10 (A, B) (SEQ ID NO: 3) shows the partial nucleotide sequence of clone #10.

Figure 11A:
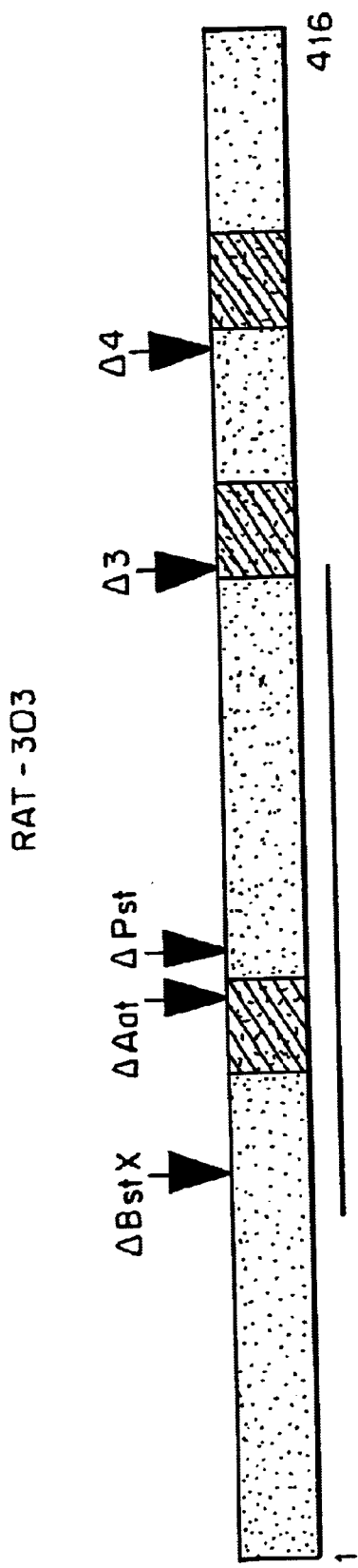
Figure 11B:
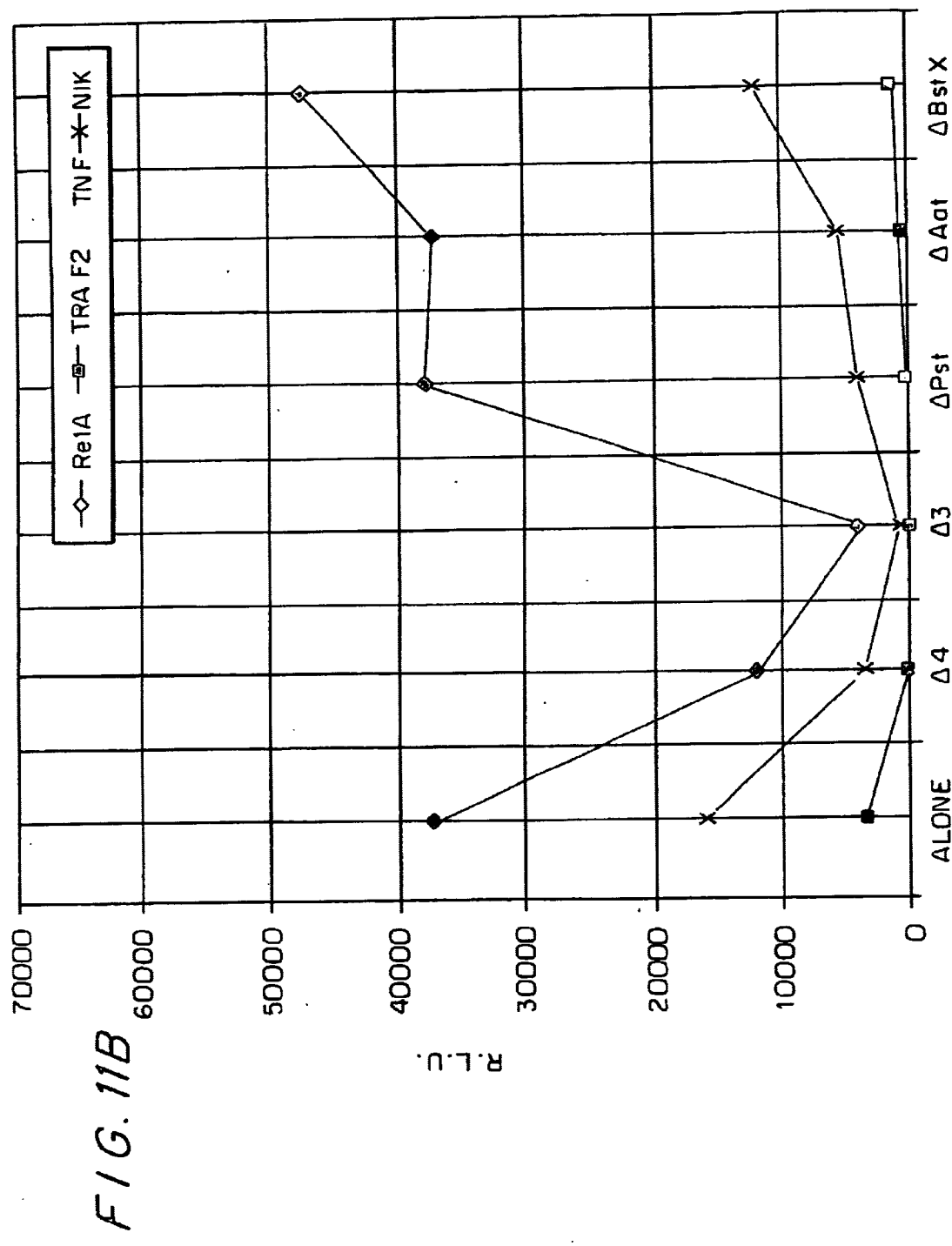

FIG. 11 shows the functional properties of serial deletions of RAP-2. In A, there is a schematic representation of the consecutive C-terminal deletions of RAP-2. All truncations share the intact RAP-2 N-terminus, while their C-terminal ends are designated by arrowheads. The RIP, NIK, IKKβ ans TIP60 binding region is underlined. Three hatched boxes correspond to the putative leucine-zipper-like motifs. B shows the effect of overexpression of the deletion constructs described in A on NF-κB activation in HEK-293T cells by RelA, TRAF2 TNF and NIK using the HIV-LTR luciferase reporter plasmid for NF-κB. Activation of the reporter gene luciferase activity is expressed in Relative Luciferase Units (R.L.U.).

Figure 12A:
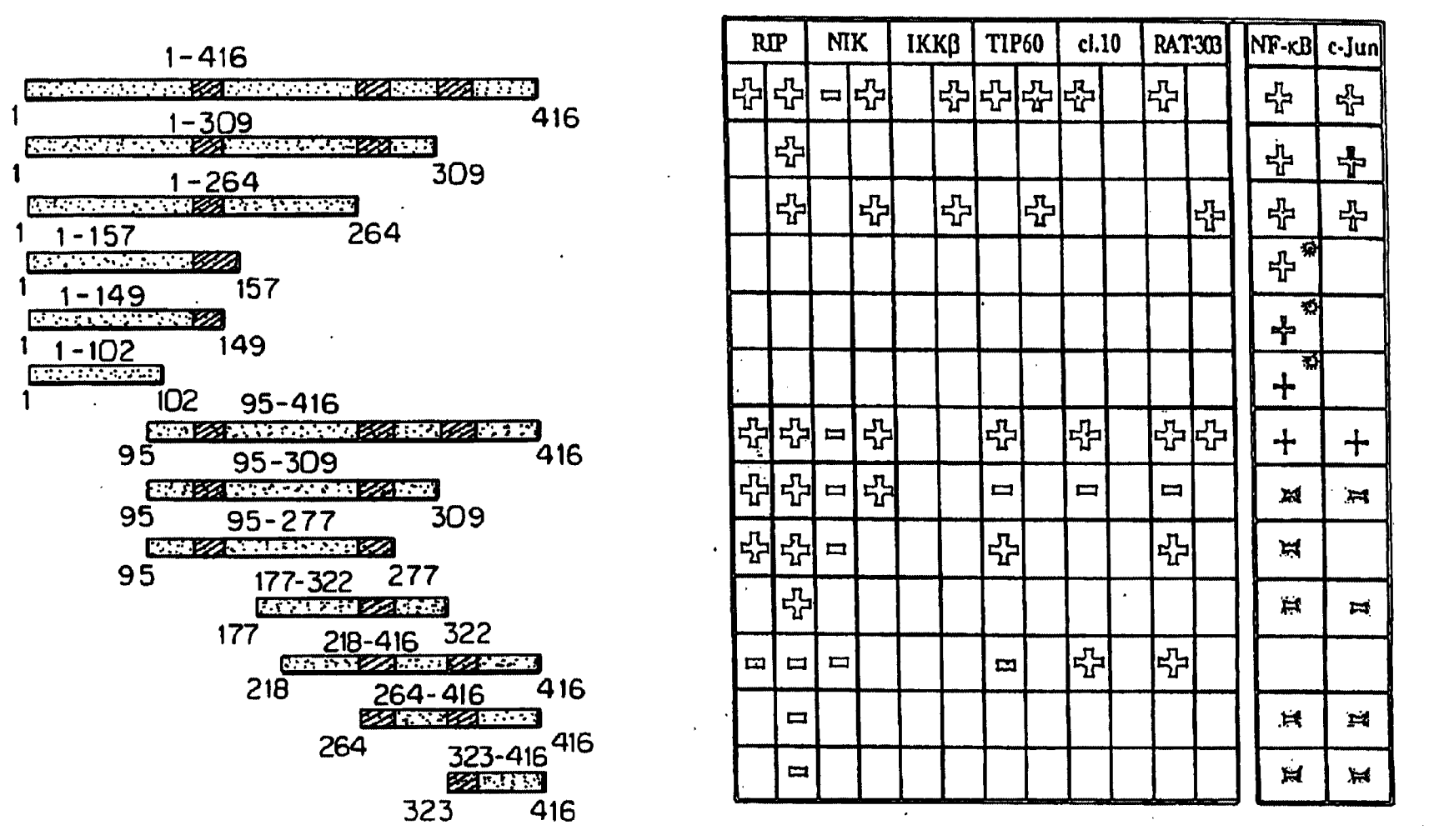

FIG. 12 shows mapping of RAP-2 functional and binding regions.

(A) Various deletions of RAP-2 were tested for their ability to bind the indicated proteins within transfected yeast (odd columns) and mammalian HEK-293T cells (even columns). The two rightmost columns show the ability of the same deletions transfected at high amounts as detailed in example 9 into HEK-293T cells, to inhibit NF-κB activation and potentiate c-Jun hyper-phosphorylation (c-Jun) in response to TNF-α treatment. Boldness of the crosses is proportional to the intensity of a given effect. Asterisks indicate that the observed effects of the labeled constructs towards Rel-A stimnulation, are distinct (see FIG. 11B).

(B) Summary of the chart representing localization of the binding (upper part) and functional (bottom part) regions of RAP-2 as inferred from the deletion analysis shown in (A), aligned along the protein backbone. The hatched parts indicate possible location of borders of the corresponding minimal regions.

Figure 13:
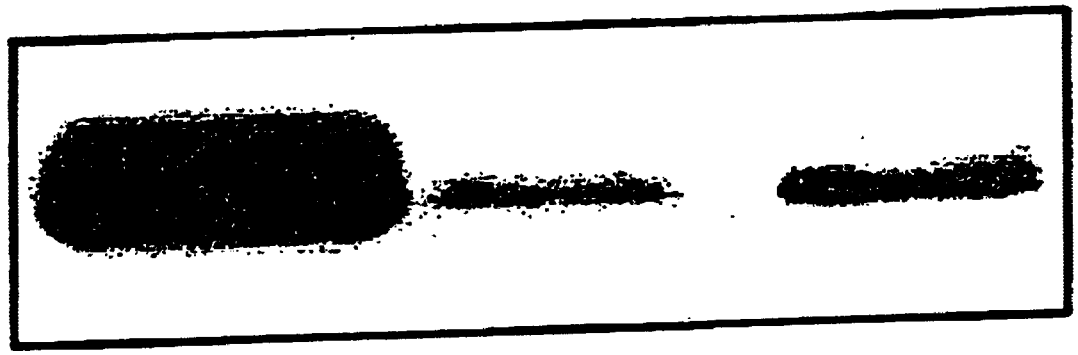

FIG. 13 shows that ser-148 in RAP-2 is essential for its ability to induce c-Jun hyper phosphorylation at ser-63.

A Western blot is shown in which wt means wild type, S148A means that the ser at position 148 was replaced with an ala, and vector is the empty control vector.

DETAILED DESCRIPTION OF THE INVENTION

The present invention relates, in one aspect, to novel RAP-2 proteins which are capable of binding to the RIP protein and thereby of mediating or modulating the intracellular activity of RIP especially where RIP is involved in modulation or mediation of inflammation, the cell death and/or cell survival pathways as detailed herein above. Thus RAP-2 may inhibit RIP activity in the cell death/inflammation survival pathway, RAP-2 may enhance RIP activity in the inflammation or cell death survival pathway, or it may enhance RIP activity in one of these pathways while inhibiting it in the other.

More particularly, in accordance with the present invention, a new protein RAP-2 is provided. RAP-2 has been sequenced and characterized and it was found that RAP-2 is a RIP-binding protein having high specificity for RIP, but does not show binding towards a number of proteins known to be involved in the intracellular signaling pathways which lead to inflammation, cell death or to cell survival. RAP-2 also apparently has none of the domains common to proteins which are active in either of these pathways, i.e. RAP-2 does not have a 'death domain' motif or module, it does not have a kinase motif or domain and it does not have a plotease domain or motif. The RAP-2 sequence determined is also a unique sequence as arises from a comparison with sequences in a number of databases including the Genebank, Human Genome level 1 and 'dbest' databases. As detailed above (also with reference to all publications and patent applications as noted) RIP is involved in the inflammation, cell death and cell survival pathways intracellularly. Hence, regulation or control of the activity of RIP can regulate either or all of these pathways when such pathways are initiated, by for example, the binding of TNF or Fas-ligand to their receptors (for TNF, the p55-R in particular). RIP may play a key role in determining which pathway is activated to a greater extent and this by virtue of its being able to bind a number of cytotoxic proteins having death domains and also a number of proteins having kinase activity. Accordingly, proteins, such as the RAP-2 protein of the present invention, which can bind specifically to RIP may play an important role in modulating RIP activity and thereby modulating the extent of induction of the one pathway in comparison to the others. Thus, the RAP-2 protein of the present invention represents an important intracellular signal modulator or mediator.

In addition to the RAP-2 full-length protein of the present invention a shorter cDNA was cloned that was found to be composed of sequence "blocks" derived from several remote regions of the "full" cDNA, apparently resulting from alternative splicing of the same gene. The murine counterpart of the human RAP-2 was identified in a similar search of the mouse ESTs collection. The partial murine cDNA was found to be virtually identical to its human counterpart throughout the coding region.

The physiological relevance of the RIP-RAP-2 interaction was further confirmed in transfected HEK-293T and HeLa cells. However, formation of such a complex did not result in RIP enzymatic activity, as evidenced by over-expressed RIP not phosphorylating RAP-2.

Transfection experiments in mammalian HEK-293T cells also resulted in stable formation of a RAP-2-NIK complex.

RAP-2 appears to be a crucial element of the NF-κB and c-Jun signal transduction pathways, as it binds NIK, IKKβ and TIP60 (a histone acetyltransferase) and modulates NF-κB and c-Jun dependent transcription. In fact, enhanced ectopic expression of RAP-2 leads to inhibition of the NF-κB response, while its depletion from the cell, by means of an antisense construct, results in enhanced NF-κB and c-Jun transactivation.

RAP-2 was also found to potentiate c-Jun hyperphosphorylation, which was not mediated by JNK activity. RAP-2 did not inhibit c-Jun and RelA binding to DNA. The binding and functional domains of RAP-2 were identified by sequential deletion analyses. These studies have indicated that the binding region for RIP, NIK and TIP60 overlaps and is found within amino acids 95–264 of RAP-2. The downstream functional effects mediated by RAP-2 however were found to localize to the N-terminal domain of the protein, encompassing amino acids 1–264.

In view of the above RAP-2 appears to be a crucial element of the signal-attenuation circuit of the stress-response network: ectopic expression of the sense-encoding construct inhibits response, while expression of antisense-encoding construct enhances the response. In fact, RAP-2 is also known in the inventor's lab as RAT (RIP's Attenuator), and may therefore be herein also denoted as RAT and/or RAT-303 and/or clone 303.

The existence of multiple splice variants indicates that, at least in part, the net effect of RAP-2 under given conditions is likely to depend on the presence of certain sequence blocks, which are necessary for the protein binding/targeting/translocation/modification, in a prevalent isoform. For instance, if, indeed, binding of RAP-2 to TIP60 allows nuclear localization of the former, it could be hypothesized that variants of RAP-2 with spliced-out nuclear localization signals (NLS) might become defective, or, conversely, overly active in NF-κB/AP-1 repression. Sequence analysis does show that RAP-2 harbors several clusters of positively charged amino acids (E, K, and R) characteristic of most of the known NLSs.

RAP-2 binding to RIP has been mapped to a region of the RAP-2 protein that begins between amino acids 177–218 and ends at amino acid 264. The RIP binding domain within RAP-2 did not overlap neither the IKKβ nor the NIK binding sites.

Binding to TIP60, a member of a family of nuclear proteins called histone acetyltransferases, apparently maps within the region spanning amino acids 95–264. The region involved in homo-dimerization was found to localize in between amino acids 217–264.

The data accumulated suggest that all the functional effects of RAP-2 (namely NF-κB inhibition and induction of c-Jun hyper-phosphorylation) map to the same region.

The protein encoded by clone #10, apparently binds within a region beginning between amino acids 218–309 and ending at amino acid 416 and thus, its binding site may comprise overlapping regions with the binding sites for RIP, NIK, IKKβ and TIP60.

Furthermore, it is possible that the region sufficient for effective modulation of signaling by all inducers localizes to the N-terminal segment of the protein.

The region encompassed by amino acids 95–416 does have an effect although it is significantly weaker, as compared to the one caused by the full-length protein and, thus, may result from enforced aggregation of the endogenous RAP-2.

Moreover, with the exception of RelA, all effects induced in our experiments can be mediated by as few as approximately 100 N-terminal amino acids of RAP-2. In fact even the fragment encompassing amino acids 1–102 mediates a distinct effect, albeit fairly moderate.

On the other hand, suppression of RelA-mediated effect requires a much longer portion of RAP-2. So far we could define the boundaries of this region within amino acids 1–264 which apparently endows the region between amino acids 157 and 264 with some specific, RelA-associated, binding properties.

In view of the above observations, it appears that:
  a. With the exception of RelA, RAP-2 binding to RIP, clone#10 and, most likely, to NIK and TIP60 are not required for the function of the protein, as inhibitor of over-expression induced NF-κB.
  b. The effect of RAP-2 on RelA over-expression-induced activation is obviously mediated, at least partly by different binding events. Essentially, all of the above-mentioned proteins may be found to contribute to the given activity, as deduced from the experiments carried out to date.

Due to the unique ability of FAS-R and the TNF receptors to cause cell death, as well as the ability of the TNF receptors to trigger various other tissue-damaging activities, aberration of the function of these receptors can be particularly deleterious to the organism. Indeed, both excessive and deficient function of these receptors have been shown to contribute to the pathological manifestations of various diseases. Identifying molecules that take part in the signaling activity of these receptors, and finding ways to modulate the function of these molecules, constitutes a potential clue for new therapeutical approaches to these diseases. In view of the suspected important role of RIP in FAS-R and p55-R toxicity, and hence the suspected important regulatory role of RAP-2 in FAS-R and TNF via modulation of RIP, it seems particularly important to design drugs that can block the cytotoxic function of RIP, possibly by way of blocking the binding of RAP-2 to RIP or otherwise inhibiting the interaction between RAP-2 and RIP under those conditions in which RAP-2 serves to enhance RIP-mediated cytotoxicity (as noted above RIP is cytotoxic on its own and in conjunction with other proteins that have death domain regions).

Likewise, it is also known (see above) that FAS-R and p55-R are involved in the activation of NF-κB and thereby of cell survival. Accordingly, when it is desired to kill cells, for example cancer cells, HIV-infected cells and the like, it would be desirable to enhance the cytotoxic effects of FAS-R and p55-R (and their associated proteins such as, for example, MORT-1, MACH, Mch4, G1, TRADD), while at the same time to inhibit their ability to induce NF-κB. Hence, when the RAP-2 interaction or binding to RIP results in an augmentation of RIP's possible role in enhancing NF-κB induction (possibly via TRAF2 and possibly via the kinase domain and/or intermediate domain of RIP), then it would be desirable to block this interaction between RAP-2 and RIP to inhibit, or at least to prevent augmentation, of NF-κB activation and thereby shift the balance of TNF- or FAS-ligand-induced effects to the side of cell cytotoxicity to ultimately provide for increased cell death.

Similarly, in the opposite situation (to that noted above) where RAP-2's binding to RIP actually causes inhibition of FAS-R and p55-R inflammatory or cytotoxic effects and it is desired to block these cytotoxic effects, e.g. in inflammation, various autoimmune diseases and the like where increased cell survival is sought, then it is important to design drugs which would enhance the interaction between RAP-2 and RIP to enhance the overall inhibition of cell death and shift the balance towards cell survival. It also follows in light of the above that in the event that RAP-2's interaction with RIP causes an inhibition in RIP's function in augmenting NF-RB activation, then when cell survival is desired, it is necessary to block this interaction between RAP-2 and RIP thereby enhancing RIP's activity in augmenting NF-κB activation.

In view of all of the aforementioned, it arises that RIP has a key role in the balance between induction or mediation of inflammation, cell death or cell survival pathways and hence RAP-2 has an equally important role by being a modulator of RIP. Influencing the RAP-2-RIP interaction/binding using various drugs or treatments as noted above and below will possibly allow for a shift in the intracellular signaling pathways from cell death to cell survival or vice versa as is desired.

The present invention also concerns the DNA sequence encoding a RAP-2 protein and the RAP-2 proteins encoded by the DNA sequences.

Moreover, the present invention further concerns the DNA sequences encoding biologically active analogs, fragments and derivatives of the RAP-2 protein, and the analogs, fragments and derivatives encoded thereby. The preparation of such analogs, fragments and derivatives is by standard procedure (see for example, Sambrook et al., 1989) in which in the DNA sequences encoding the RAP-2 protein, one or more codons may be deleted, added or substituted by another, to yield analogs having at least one amino acid residue change with respect to the native protein.

Of the above DNA sequences of the invention which encode a RAP-2 protein, isoform, analog, fragment or derivative, there is also included, as an embodiment of the invention, DNA sequences capable of hybridizing with a cDNA sequence derived from the coding region of a native RAP-2 protein, in which such hybridization is performed under moderately stringent conditions, and which hybridizable DNA sequences encode a biologically active RAP-2 protein. These hybridizable DNA sequences therefore include DNA sequences which have a relatively high homology to the native RAP-2 cDNA sequence and as such represent RAP-2-like sequences which may be, for example, naturally-derived sequences encoding the various RAP-2 isoforms, or naturally-occuring sequences encoding proteins belonging to a group of RAP-2-like sequences encoding a protein having the activity of RAP-2. Further, these sequences may also, for example, include non-naturally occuring, synthetically produced sequences, that are similar to the native RAP-2 cDNA sequence but incorporate a number of desired modifications. Such synthetic sequences therefore include all of the possible sequences encoding analogs, fragments and derivatives of RAP-2, all of which have the activity of RAP-2.

To obtain the various above noted naturally occuring RAP-2-like sequences, standard procedures of screening and isolation of naturally-derived DNA or RNA samples from various tissues may be employed using the natural RAP-2 CDNA or portion thereof as probe (see for example standard procedures set forth in Sambrook et al., 1989).

Likewise, to prepare the above noted various synthetic RAP-2-like sequences encoding analogs, fragments or derivatives of RAP-2, a number of standard procedures may be used as are detailed herein below concerning the preparation of such analogs, fragments and derivatives.

A polypeptide or protein "substantially corresponding" to RAP-2 protein includes not only RAP-2 protein but also polypeptides or proteins that are analogs of RAP-2.

Analogs that substantially correspond to RAP-2 protein are those polypeptides in which one or more amino acid of the RAP-2 protein's amino acid sequence has been replaced with another amino acid, deleted and/or inserted, provided that the resulting protein exhibits substantially the same or higher biological activity as the RAP-2 protein to which it corresponds.

In order to substantially correspond to RAP-2 protein, the changes in the sequence of RAP-2 proteins, such as isoforms are generally relatively minor. Although the number of changes may be more than ten, preferably there are no more than ten changes, more preferably no more than five, and most preferably no more than three such changes. While any technique can be used to find potentially biologically active proteins which substantially correspond to RAP-2 proteins, one such technique is the use of conventional mutagenesis techniques on the DNA encoding the protein, resulting in a few modifications. The proteins expressed by such clones can then be screened for their ability to bind to RIP and to modulate RIP activity in modulation/mediation of the intracellular pathways noted above.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of RAP-2 proteins include an analog wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of RAP-2 protein.

TABLE 1A

| Original Residue | Exemplary Substitution |
| --- | --- |
| Ala | Gly;Ser |
| Arg | Lys |
| Asn | Gln;His |
| Asp | Glu |
| Cys | Ser |
| Gln | Asn |
| Glu | Asp |
| Gly | Ala;Pro |
| His | Asn;Gln |
| Ile | Leu;Val |
| Leu | Ile;Val |
| Lys | Arg;Gln;Glu |
| Met | Leu;Tyr;Ile |
| Phe | Met;Leu;Tyr |
| Ser | Thr |
| Thr | Ser |
| Trp | Tyr |
| Tyr | Trp;Phe |

Alternatively, another group of substitutions of RAP-2 protein are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1–2 of Schulz et al., G. E., Principles of Protein Structure Springer-Verlag, New York, N.Y., 1798, and FIGS. 3–9 of Creighton, T. E., Proteins: Structure and Molecular Properties, W.H. Freeman & Co., San Francisco, Calif. 1983. Based on such an analysis, alternative conservative substitutions are defined herein as exchanges within one of the following five groups:

TABLE 1B

1. Small aliphatic, nonpolar or slightly polar residues: Ala, Ser, Thr (Pro, Gly);
2. Polar negatively charged residues and their amides: Asp, Asn, Glu, Gln;
3. Polar positively charged residues: His, Arg, Lys;
4. Large aliphatic nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. This however tends to promote the formation of secondary structure other than a-helical. Pro, because of its unusual geometry, tightly constrains the chain and generally tends to promote β-turn-like structures, although in some cases Cys can be capable of participating in disulfide bond formation which is important in protein folding. Note that Schulz et al., supra, would merge Groups 1 and 2, above. Note also that Tyr, because of its hydrogen bonding potential, has significant kinship with Ser, and Thr. etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. a-helix or β-sheet, as well as changes in biological activity, e.g., binding to RIP and/or mediation of RIP's effect on cell death.

Examples of production of amino acid substitutions in proteins which can be used for obtaining analogs of RAP-2 proteins for use in the present invention include any known method steps, such as presented in U.S. Pat. No. RE 33,653, U.S. Pat. Nos. 4,959,314, 4,588,585 and 4,737,462, to Mark et al.; U.S. Pat. No. 5,116,943 to Koths et al., U.S. Pat. No. 4,965,195 to Namen et al.; U.S. Pat. No. 4,879,111 to Chong et al.; and U.S. Pat. No. 5,017,691 to Lee et al.; and lysine substituted proteins presented in U.S. Pat. No. 4,904,584 (Shaw et al.).

Besides conservative substitutions discussed above which would not significantly change the activity of RAP-2 protein, either conservative substitutions or less conservative and more random changes, which lead to an increase in biological activity of the analogs of RAP-2 proteins are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

Acceptable RAP-2 analogs are those which retain at least the capability of binding to RIP, and thereby, as noted above mediate the activity of RIP in the intracellular pathways as noted above. In such a way, analogs can be produced which have a so-called dominant-negative effect, namely, an analog which is defective either in binding to RIP, or in subsequent signaling or other activity following such binding. Such analogs can be used, for example, to inhibit the effect of RIP, or to inhibit the NF-κB inducing (direct or indirect) effect of RIP, depending on which of these activities is the major one modulated by the interaction of RAP-2 and RIP (see above), and this by such analogs competing with the natural RAP-2 for binding to RIP.

At the genetic level, these analogs are generally prepared by site-directed mutagenesis of nucleotides in the DNA encoding the RAP-2 protein, thereby producing DNA encoding the analog, and thereafter synthesizing the DNA and expressing the polypeptide in recombinant cell culture. The analogs typically exhibit the same or increased qualitative biological activity as the naturally occurring protein, Ausubel et al., Current Protocols in Molecular Biology, Greene Publications and Wiley Interscience, New York, N.Y., 1987–1995; Sambrook et al., Molecular Cloning: A Laboratory Manual, Cold Spring Harbor Laboratory, Cold Spring Harbor, N.Y., 1989.

Preparation of a RAP-2 protein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of a RAP-2 protein. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., DNA 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, Editor A. Walton, Elsevier, Amsterdam (1981), the disclosure of which is incorporated herein by reference. These phage are readily available commercially and their use is generally well known to those skilled in the art. Alternatively, plasmid vectors that contain a single-stranded phage origin of replication (Veira et al., Meth. Enzymol. 153:3, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as E. coli polymerase I Klenow fragment, to complete the synthesis of the mutation-bearing strand. Thus, a mutated sequence and the second strand bears the desired mutation. This heteroduplex vector is then used to transform appropriate cells, such as E. coli JM101 cells, and clones are selected that include recombinant vectors bearing the mutated sequence arrangement.

After such a clone is selected, the mutated RAP-2 protein sequence may be removed and placed in an appropriate vector, generally a transfer or expression vector of the type that may be employed for transfection of an appropriate host.

Accordingly, gene or nucleic acid encoding for a RAP-2 protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding RAP-2 protein or a fragment thereof to be custom designed for ligation other sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4.683,195, 4,683,202, 4,800,159, 4,965,188, to Mullis et al.; U.S. Pat. Nos. 4,795,699 and 4,921,794 to Tabor et al.; U.S. Pat. No. 5,142,033 to Innis; U.S. Pat. No. 5,122,464 to Wilson et al.; U.S. Pat. No. 5,091,310 to Innis; U.S. Pat. No. 5,066,584 to Gyllensten et al.; U.S. Pat. No. 4,889,818 to Gelfand et al.; U.S. Pat. No. 4,994,370 to Silver et al.; U.S. Pat. No. 4,766,067 to Biswas; U.S. Pat. No. 4,656,134 to Ringold; and Innis et al., eds., PCR Protocols: A Guide to Method and Applications) and RNA mediated amplification which uses anti-sense RNA to the target sequence as a template for double stranded DNA synthesis (U.S. Pat. No. 5,130,238 to Malek et al., with the tradename NASBA); and immuno-PCR which combines the use of DNA amplification with antibody labeling (Ruzicka et al., Science 260:487 (1993); Sano et al., Science 258:120 (1992); Sano et al., Biotechniques 9:1378 (1991)), the entire contents of which patents and reference are entirely incorporated herein by reference.

In an analogous fashion, biologically active fragments of RAP-2 proteins (e.g. those of any of the RAP-2 or its isoforms) may be prepared as noted above with respect to the analogs of RAP-2 proteins. Suitable fragments of RAP-2 proteins are those which retain the RAP-2 capability and which can modulate or mediate the biological activity of RIP or other proteins associated with RIP directly or indirectly. Accordingly, RAP-2 protein fragments can be prepared which have a dominant-negative or a dominant-positive effect as noted above with respect to the analogs. It should be noted that these fragments represent a special class of the analogs of the invention, namely, they are defined portions of RAP-2 proteins derived from the full RAP-2 protein sequence (e.g., from that of any one of the RAP-2 or its isoforms), each such portion or fragment having any of the above-noted desired activities. Such fragment may be, e.g., a peptide.

Similarly, derivatives may be prepared by standard modifications of the side groups of one or more amino acid residues of the RAP-2 protein, its analogs or fragments, or by conjugation of the RAP-2 protein, its analogs or fragments, to another molecule e.g. an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity as RAP-2 proteins.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

RAP-2 is a protein or polypeptide, i.e. a sequence of amino acid residues. A polypeptide consisting of a larger sequence which includes the entire sequence of a RAP-2 protein, in accordance with the definitions herein, is intended to be included within the scope of such a polypeptide as long as the additions do not affect the basic and novel characteristics of the invention, i.e., if they either retain or increase the biological activity of RAP-2 protein or can be cleaved to leave a protein or polypeptide having the biological activity of RAP-2 protein. Thus, for example, the present invention is intended to include fusion proteins of RAP-2 protein with other amino acids or peptides.

The new RAP-2 protein, their analogs, fragments and derivatives thereof, have a number of possible uses, for example:

(i) RAP-2 protein, its analogs, fragments and derivatives thereof, may be used to modulate the function of RIP in either of the inflammation, cell death or the cell survival pathways as noted above. For example, if RAP-2 can modulate RIP's effect on activation of NF-κB, JNK (Jun kinase) or p38 kinase, both such RAP-2 effects leading to enhance such a RAP-2-RIP effect when it would be desirable in anti-tumor, anti- or pro-inflammatory, anti-HIV applications, etc. In this case the RAP-2 protein, its analogs, fragments or derivatives thereof, which modulate inflammation, enhance the cytotoxic effect, or block the cell survival effect, may be introduced to the cells by standard procedures known per se. For example, when the RAP-2 protein is entirely intracellular (as suspected) and should be introduced only into the cells where the FAS-R ligand or TNF or other cytotoxic protein effect, mediated by RIP, is desired, a system for specific introduction of this protein into the cells is necessary. One way of doing this is by creating a recombinant animal virus, e.g., one derived from Vaccinia, to the DNA of which the following two genes will be introduced: the gene encoding a ligand that binds to cell surface proteins specifically expressed by the cells, e.g., ones such as the AIDs (HIV) virus gp120 protein which binds specifically to some cells (CD4 lymphocytes and related leukemias), or any other ligand that binds specifically to cells carrying a FAS-R or p55-R, such that the recombinant virus vector will be capable of binding such FAS-R- or p55-R-carrying cells; and the gene encoding the RAP-2 protein. Thus, expression of the cell-surface-binding protein on the surface of the virus will target the virus specifically to the tumor cell or other FAS-R- or p55-R-carrying cell, following which the RAP-2 protein encoding sequence will be introduced into the cells via the virus, and once expressed in the cells, will result in enhancement of the RIP mediation of the FAS-R ligand or TNF effect or independent RIP. Construction of such recombinant animal virus is by standard procedures (see for example, Sambrook et al., 1989). Another possibility is to introduce the sequences of the RAP-2 protein (e.g., any one of the RAP-2 or its isoforms) in the form of oligonucleotides which can be absorbed by the cells and expressed therein.

(ii) They may be used to inhibit the FAS-R ligand or TNF or related protein effect, mediated by RIP or independent RIP effect, e.g., in cases such as tissue damage in septic shock, graft-vs.-host rejection, or acute hepatitis, in which it is desired to block the FAS-R ligand or TNF induced FAS-R or p55-R intracellular signaling or independent RIP effect, or other protein-mediated signaling and at the same time to increase the cell survival pathway. In this situation, it is possible, for example, to introduce into the cells, by standard procedures, oligonucleotides having the anti-sense coding sequence for the RAP-2 protein, which would effectively block the translation of mRNAs encoding the RAP-2 protein and thereby block its expression and lead to the inhibition of the FAS-R ligand or TNF- or RIP or other protein-effect. Such oligonucleotides may be introduced into the cells using the above recombinant virus approach, the second sequence carried by the virus being the oligonucleotide sequence.

Likewise, as noted above, depending on the nature of the RAP-2-RIP interaction, it may be possible by the ways of (i) and (ii) above to enhance or inhibit cell inflammation and survival pathways where desired.

Another possibility is to use antibodies specific for the RAP-2 protein to inhibit its intracellular signaling activity.

Yet another way of inhibiting the RIP-mediated effects or RIP independent effect is by the recently developed ribozyme approach. Ribozymes are catalytic RNA molecules that specifically cleave RNAs. Ribozymes may be engineered to cleave target RNAs of choice, e.g., the mRNAs encoding the RAP-2 protein of the invention. Such ribozymes would have a sequence specific for the RAP-2 protein mRNA and would be capable of interacting therewith (complementary binding) followed by cleavage of the mRNA, resulting in a decrease (or complete loss) in the expression of the RAP-2 protein, the level of decreased expression being dependent upon the level of ribozyme expression in the target cell. To introduce ribozymes into the cells of choice (e.g., those carrying FAS-R or p55-R), any suitable vector may be used, e.g., plasmid, animal virus (retrovirus) vectors, that are usually used for this purpose (see also (i) above, where the virus has, as second sequence, a cDNA encoding the ribozyme sequence of choice). (For reviews, methods etc. concerning ribozymes see Chen et al., 1992; Zhao and Pick, 1993; Shore et al., 1993; Joseph and Burke, 1993; Shimayama et al., 1993; Cantor et al., 1993; Barinaga, 1993; Crisell et al., 1993 and Koizumi et al., 1993). This approach is suitable when the RAP-2-RIP interaction enhances cell cytotoxicity in situations when it is desired to block this cytotoxicity, or when the RAP-2-RIP interaction inhibits NF-κB activation in the same situation when it is desired to block this inhibition to increase such NF-κB activation, i.e. in both cases it is desired to increase cell survival as in (ii) above.

(iii) The RAP-2 protein, its analogs, fragments or derivatives may also be used to isolate, identify and clone other proteins of the same class, i.e., those binding to RIP or to functionally related receptors or proteins, involved in the intracellular signaling process. In this application the above noted yeast two-hybrid system may be used, or there may be used a recently developed system employing non-stringent Southern hybridization followed by PCR cloning (Wilks et al., 1989). In the Wilks et al. publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequence of the RAP-2 protein to identify and clone those of related RIP-binding proteins.

(iv) Yet another approach to utilizing the RAP-2 protein, or its analogs, fragments or derivatives thereof, of the invention is to use them in methods of affinity chromatography to isolate and identify other proteins or factors to which they are capable of binding, e.g., other proteins or factors involved in the intracellular signaling process. In this application, the RAP-2 protein, its analogs, fragments or derivatives thereof, of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the RAP-2 protein, or its analogs, fragments or derivatives thereof of the invention, can be eluted, isolated and characterized.

(v) As noted above, the RAP-2 protein, or its analogs, fragments or derivatives thereof, of the invention may also be used as immunogens (antigens) to produce specific antibodies thereto. These antibodies may also be used for the purposes of purification of the RAP-2 protein (e.g., RAP-2 or any of its isoforms) either from cell extracts or from transformed cell lines producing RAP-2 protein, or its analogs or fragments. Further, these antibodies may be used for diagnostic purposes for identifying disorders related to abnormal functioning of the RIP-mediated FAS-R ligand or TNF system, or independent RIP activities, e.g., overactive or underactive FAS-R ligand- or TNF-induced cellular effects mediated by RIP or RIP's own specific cellular effects. Thus, should such disorders be related to a malfunctioning intracellular signaling system involving the RIP protein, or various other, above noted RIP-binding proteins or RAP-2 protein itself, such antibodies would serve as an important diagnostic tool.

It should also be noted that the isolation, identification and characterization of the RAP-2 protein of the invention may be performed using any of the well known standard screening procedures. For example, one of these screening procedures, the yeast two-hybrid procedure as is set forth herein below, was used to identify the RIP protein (see Stanger et al., 1995) and subsequently the various RAP-2 proteins of the invention (besides various other new proteins of the above and below noted co-owned co-pending patent applications). Likewise as noted above and below, other procedures may be employed such as affinity chromatography, DNA hybridization procedures, etc. as are well known in the art, to isolate, identify and characterize the RAP-2 protein of the invention or to isolate, identify and characterize additional proteins, factors, receptors, etc. which are capable of binding to the RAP-2 proteins of the invention.

As set forth hereinabove, the RAP-2 protein may be used to generate antibodies specific to RAP-2 proteins, e.g., RAP-2 and its isoforms. These antibodies or fragments thereof may be used as set forth hereinbelow in detail, it being understood that in these applications the antibodies or fragments thereof are those specific for RAP-2 proteins.

Based on the findings in accordance with the present invention that RAP-2 binds specifically to RIP and as such is a mediator/modulator of RIP and can thus mediate/modulate RIP's activity in inflammation, cell death or cell survival pathways in ways that RIP functions independently or in conjunction with other proteins (e.g. FAS-R, p55-R, MORT-1, MACH, Mch4, G1 and TRADD in cell death pathways, or with TRAF2 in cell survival pathways) it is of importance to design drugs which may enhance or inhibit the RAP-2-RIP interaction, as desired and depending on which of these pathways are enhanced/inhibited by the RAP-2-RIP interaction. There are many diseases in which such drugs can be of great help. Amongst others, acute hepatitis in which the acute damage to the liver seems to reflect FAS-R ligand-mediated death of the liver cells; autoimmune-induced cell death such as the death of the β Langerhans cells of the pancreas, that results in diabetes; the death of cells in graft rejection (e.g., kidney, heart and liver); the death of oligodendrocytes in the brain in multiple sclerosis; and AIDS-inhibited T cell suicide which causes proliferation of the AIDS virus and hence the AIDS disease.

It is possible that RAP-2 or one or more of its possible isoforms may serve as "natural" inhibitors of RIP in one or more of the above pathways and these may thus be employed as the above noted specific inhibitors of RIP. Likewise, other substances such as peptides, organic compounds, antibodies, etc. may also be screened to obtain specific drugs which are capable of inhibiting the RAP-2-RIP interaction.

A non-limiting example of how peptide inhibitors of the RAP-2-RIP interaction would be designed and screened is based on previous studies on peptide inhibitors of ICE or ICE-like proteases, the substrate specificity of ICE and strategies for epitope analysis using peptide synthesis. The minimum requirement for efficient cleavage of peptide by ICE was found to involve four amino acids to the left of the cleavage site with a strong preference for aspartic acid in the P1 position and with methylamine being sufficient to the right of the P1 position (Sleath et al., 1990; Howard et al., 1991; Thomberry et al., 1992). Furthermore, the fluorogenic substrate peptide (a tetrapeptide), acetyl-Asp-Glu-Val-Asp-a-(4-methyl-coumaryl-7-amide) abbreviated Ac-DEVD-AMC, corresponds to a sequence in poly (ADP-ribose) polymerase (PARP) found to be cleaved in cells shortly after FAS-R stimulation, as well as other apoptopic processes (Kaufmann, 1989; Kaufmann et al., 1993; Lazebnik et al., 1994), and is cleaved effectively by CPP32 (a member of the CED3/ICE protease family) and MACH proteases (and likewise also possibly by G1 proteases—see for example co-owned co-pending IL 120367).

As Asp in the P1 position of the substrate appears to be important, tetrapeptides having Asp as the fourth amino acid residue and various combinations of amino acids in the first three residue positions can be rapidly screened for binding to the active site of the proteases using, for example, the method developed by Geysen (Geysen, 1985; Geysen et al., 1987) where a large number of peptides on solid supports were screened for specific interactions with antibodies. The binding of MACH proteases to specific peptides can be detected by a variety of well known detection methods within the skill of those in the art, such as radiolabeling of the G1 proteases, etc. This method of Geysen's was shown to be capable of testing at least 4000 peptides each working day.

In a similar way the exact binding region or region of homology which determines the interaction between RAP-2 and RIP can be elucidated and then peptides may be screened which can serve to block this interaction, e.g. peptides synthesized having a sequence similar to that of the binding region or complementary thereto which can compete with natural RAP-2 for binding to RIP.

Drug or peptide inhibitors, which are capable of inhibiting inflammation or the cell death activity of RAP-2 by inhibiting the RAP-2-RIP interaction can be conjugated or complexed with molecules that facilitate entry into the cell.

U.S. Pat. No. 5,149,782 discloses conjugating a molecule to be transported across the cell membrane with a membrane blending agent such as fusogenic polypeptides, ion-channel forming polypeptides, other membrane polypeptides, and long chain fatty acids, e.g. myristic acid, palmitic acid. These membrane blending agents insert the molecular conjugates into the lipid bilayer of cellular membranes and facilitate their entry into the cytoplasm.

Low et al., U.S. Pat. No. 5,108,921, reviews available methods for transmembrane delivery of molecules such as, but not limited to, proteins and nucleic acids by the mechanism of receptor mediated endocytotic activity. These receptor systems include those recognizing galactose, mannose, mannose 6-phosphate, transferrin, asialoglycoprotein, transcobalamin (vitamin B12), α-2 macroglobulins, insulin and other peptide growth factors such as epidermal growth factor (EGF). Low et al. teaches that nutrient receptors, such as receptors for biotin and folate, can be advantageously used to enhance transport across the cell membrane due to the location and multiplicity of biotin and folate receptors on the membrane surfaces of most cells and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

In addition, it is known in the art that fusing a desired peptide sequence with a leader/signal peptide sequence to create a "chimeric peptide" will enable such a "chimeric peptide" to be transported across the cell membrane into the cytoplasm.

As will be appreciated by those of skill in the art of peptides, the peptide inhibitors of the RAP-2-RIP interaction according to the present invention is meant to include peptidomimetic drugs or inhibitors, which can also be rapidly screened for binding to RAP-2/RIP protease to design perhaps more stable inhibitors.

It will also be appreciated that the same means for facilitating or enhancing the transport of peptide inhibitors across cell membranes as discussed above are also applicable to the RAP-2 or its isoforms themselves as well as other peptides and proteins which exert their effects intracellularly.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which populations contains substantially similar epitope binding sites. MAbs may be obtained by methods known to those skilled in the art. See, for example Kohler and Milstein, Nature, 256:495–497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992–1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules of which different portions are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., Proc. Natl. Acad. Sci. USA 81:3273–3277 (1984); Morrison et al., Proc. Natl. Acad. Sci. USA 81:6851–6855 (1984); Boulianne et al., Nature 312:643–646 (1984); Cabilly et al., European Patent Application 125023 (published Nov. 14, 1984); Neuberger et al., Nature 314:268–270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., J. Immunol. 137:1066–1074 (1986); Robinson et al., International Patent Application No. WO8702671 (published May 7, 1987); Liu et al., Proc. Natl. Acad. Sci USA 84:3439–3443 (1987); Sun et al., Proc. Natl. Acad. Sci USA 84:214–218 (1987); Better et al., Science 240:1041–1043 (1988); and Harlow and Lane, ANTIBODIES:A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the RAP-2 proteins, analogs, fragments or derivatives thereof, of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above RAP-2 protein, or analogs, fragments and derivatives thereof.

The anti-Id mAbs thus have their own idiotypic epitopes, or "idiotopes" structurally similar to the epitope being evaluated, such as GRB protein-a.

The term "antibody" is also meant to include both intact molecules as well as fragments thereof, such as, for example, Fab and F(ab')2, which are capable of binding antigen. Fab and F(ab')$_2$ fragments lack the Fc fragment of intact antibody, clear more rapidly from the circulation, and may have less non-specific tissue binding than an intact antibody (Wahl et al., J. Nucl. Med. 24:316–325 (1983)).

It will be appreciated that Fab and F(ab')$_2$ and other fragments of the antibodies useful in the present invention may be used for the detection and quantitation of the RAP-2 protein according to the methods disclosed herein for intact antibody molecules. Such fragments are typically produced by proteolltic cleavage, using enzymes such as papain (to produce Fab fragments) or pepsin (to produce F(ab')$_2$ fragments).

An antibody is said to be "capable of bindingc" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the RAP-2 protein in a sample or to detect presence of cells which express the RAP-2 protein of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the RAP-2 protein of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the RAP-2 protein, but also its distribution on the examined tissue. Using the present invention, those of ordinary skill will readily perceive that any of wide variety of histological methods (such as staining procedures) can be modified in order to achieve such in situ detection.

Such assays for the RAP-2 protein of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the RAP-2 protein, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomeras, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholin-esterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, N.Y. (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as 152E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The RAP-2 proteins of the invention may be produced by any standard recombinant DNA procedure (see for example, Sambrook, et al., 1989 and Ansabel et al., 1987–1995, supra) in which suitable eukaryotic or prokaryotic host cells well known in the art are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs, fragments and derivatives, and thus the vectors encoding them also include vectors encoding analogs and fragments of these proteins, and the transformed hosts include those producing such analogs and fragments. The derivatives of these proteins, produced by the transformed hosts, are the derivatives produced by standard modification of the proteins or their analogs or fragments.

The present invention also relates to pharmaceutical compositions comprising recombinant animal virus vectors encoding the RAP-2 proteins, which vector also encodes a virus surface protein capable of binding specific target cell (e.g., cancer cells) surface proteins to direct the insertion of the RAP-2 protein sequences into the cells. Further pharmaceutical compositions of the invention comprises as the active ingredient (a) an oligonucleotide sequence encoding an anti-sense sequence of the RAP-2 protein sequence, or (b) drugs that block the RAP-2-RIP interaction.

Pharmaceutical compositions according to the present invention include a sufficient amount of the active ingredient to achieve its intended purpose. In addition, the pharmaceutical compositions may contain suitable pharmaceutically acceptable carriers comprising excipients and auxiliaries which facilitate processing of the active compounds into preparations which can be used pharmaceutically and which can stabilize such preparations for administration to the subject in need thereof as well known to those of skill in the art.

The RAP-2 protein and its isoforms or isotypes are suspected to be expressed in different tissues at markedly different levels and apparently also with different patterns of isotypes in an analogous fashion to the expression of various other proteins involved in the intracellular signaling pathways as indicated in the above listed co-owned co-pending patent applications. These differences may possibly contribute to the tissue-specific features of response to the Fas/APO1-ligand and TNF. As in the case of other CED3/ICE homologs (Wang et al., 1994; Alnemri et al., 1995), the present inventors have previously shown (in the above mentioned patent applications) that MACH isoforms that contain incomplete CED3/ICE regions (e.g., MACHα3) are found to have an inhibitory effect on the activity of co-expressed MACHα1 or MACHα2 molecules; they are also found to block death induction by Fas/APO1 and p55-R. Expression of such inhibitory isoforms in cells may constitute a mechanism of cellular self-protection against Fas/APO1- and TNF-mediated cytotoxicity. A similar inhibitory effect of at least some G1 isoforms is also suspected (G1 being a recently isolated new Mch4- and possibly MACH-binding protein, and also MORT-1-binding protein that has MORT MODULES and a protease domain—see co-owned co-pending IL 120367). The wide heterogeneity of MACH isoforms, and likewise the suspected, analogous heterogeneity of G1 isoforms, which greatly exceeds that observed for any of the other proteases of the CED3/ICE family, should allow a particularly fine tuning of the function of the active MACH isoforms, and by analogy also the active G1 isoforms. Hence, as noted above, the RAP-2 proteins or possible isoforms may have varying effects in different tissues as regards their interaction with RIP and their influence thereby on the balance between activation of cell death or cell survival pathways, as described above.

It is also possible that some of the possible RAP-2 isoforms serve other functions. For example, RAP-2 or some RAP-2 isoforms may also act as docking sites for molecules that are involved in other, non-cytotoxic effects of Fas/APO1 and TNF receptors via interaction with RIP or even independently of RIP.

Due to the unique ability of Fas/APO1 and TNF receptors to cause inflammation, cell death, as well as the ability of the TNF receptors to trigger other tissue-damaging activities, aberrations in the function of these receptors could be particularly deleterious to the organism. Indeed, both excessive and deficient functioning of these receptors have been shown to contribute to pathological manifestations of various diseases (Vassalli, 1992; Nagata and Golstein, 1995). Identifying the molecules that participate in the signaling activity of the receptors, and finding ways to modulate the activity of these molecules, could direct new therapeutic approaches. Other aspects of the invention will be apparent from the following examples.

The invention will now be described in more detail in the following non-limiting examples and the accompanying drawings.

It should also be noted that the procedures of:

i) two-hybrid screen and two-hybrid β-galactosidase expression test; (ii) induced expression, metabolic labeling and immunoprecipitation of proteins; (iii) in vitro binding; (iv) assessment of the cytotoxicity; and (v) Northern and sequence analyses, (see also Boldin et al., 1995b) 2, 3 (see also Boldin et al., 1996) and 4, below, with respect to MORT-1 and a MORT-1 binding protein, (e.g. MACH), as well as the newly isolated protein G1 (see IL 120367) are equally applicable (with some modifications) for the corresponding isolation, cloning and characterization of RAP-2 and its possible isoforms of the present invention. These procedures are thus to be construed as the full disclosure of the same procedures used for the isolation, cloning and characterization of RAP-2 in accordance with the present invention, as detailed e.g. in the same or equivalent form in the co-owned co-pending Israel Application Nos. 114,615, 114,986, 115,319, 116588, 117,932, and 120367 as well as the corresponding PCT application No. PCT/US96/10521. Further, as regards the NIK protein and its role in activating NF-κB and hence cell survival and the role played by TRAF2 in this cell survival pathway, for example the interaction between TRAF2 and RIP and other proteins, these have been detailed by the present inventors in co-pending co-owned IL 117800, IL 119133 and Malinin et al., 1997.

EXAMPLE 1

Cloning and Isolation of the RAP-2 Protein which Binds to the RIP Protein

Two-hybrid Screening, Sequencing and Preliminary Analysis

Using the two-hybrid screen with RIP as the bait (see e.g. Fields and Song, 1989, WO/96/18641) in a B-cell library, a clone of about 1.5 Kb size was isolated. This 1.5 Kb clone (see arrow in FIGS. 1 and 2) was used for screening a phage cDNA library, yielding an about 2.0 Kb clone, the sequence of which is shown in FIG. 1.

By employing EST matching with the sequence of the 1.5 Kb clone, an EST fragment was obtained which constitutes the 3' end of I.M.A.G.E. consortium clone # 41072 (Research Genetics Institute). Of this clone, which originates from a fetal brain library, only two small sequence fragments at its 3' and 5' ends are published. After obtaining the clone it was sequenced and it turned out that even these published sequence fragments contained errors. The sequenced clone (FIG. 2), was found to be identical to the clone of FIG. 1 in its coding region, but showed differences in the 5'-noncoding region. It is therefore assumed that both cDNAs are alternatively spliced forms of the same gene.

Analysis of the sequence shows that like RAP, RAP-2 protein apparently does not have a 'death domain', it does not have a MORT MODULE, it does not have a protease domain like those of the ICE family, it does not have a kinase domain, nor does it have TRAF domains (see above noted co-pending, co-owned patent applications and the various references, especially Malinin et al., 1997 with respect to all the various domains present in the intracellular signaling pathways). Nor were any considerable motifs found to be present within the given sequence, except for three leucine zipper (LZ)—'like' blocks evenly distributed along the protein coding region. These were termed 'like', because two of them contain Leu to Val, Met or Ile substitutions. Although usually considered conservative, it is not clear if such changes within the leucine zipper domain allow the protein to retain its functional activity i.e. binding to other LZs. Binding studies revealed that RAP-2 essentially binds to RIP, RAP-2 being unable to bind to TRADD, MORT-1, p55-R, p75-R and MACH (in studies performed to date). These results support the fact that RAP-2 is apparently devoid of 'death domains' and MORT MODULES.

Therefore, it appears that RAP-2 is a specific RIP-binding protein that interacts/binds to RIP in a very specific way. Thus RAP-2 appears to be a specific modulator/mediator of RIP intracellular activity having an important role in RIP's modulation/mediation of the inflammation and the cell death/cell survival pathways.

Briefly, a clone of the RAP-2 was obtained by two-hybrid screening of a human B-cell cDNA library using the full length RIP protein as 'bait'. The RIP sequence was available from previous publications (e.g. Stanger et al., 1995) and as present in the GenBank database under accession No. U 25994 which is the human RIP sequence (also present was the mouse RIP sequence under accession No. U 25995). Using this sequence information appropriate PCR-primers were designed by OLIGO4™ software and the DNA fragment corresponding to the coding part of RIP was obtained by PCR using as template cDNA from the total RNA Human Fibroblast Cell library (using standard procedures). This coding part of RIP was then cloned into the pGBT-9 vector (Clontech) and used as bait, as noted above, in the two-hybrid screening procedure. In this two-hybrid screen a clone was obtained coding for a RIP-binding protein that interacts with RIP.

Figure 3A:
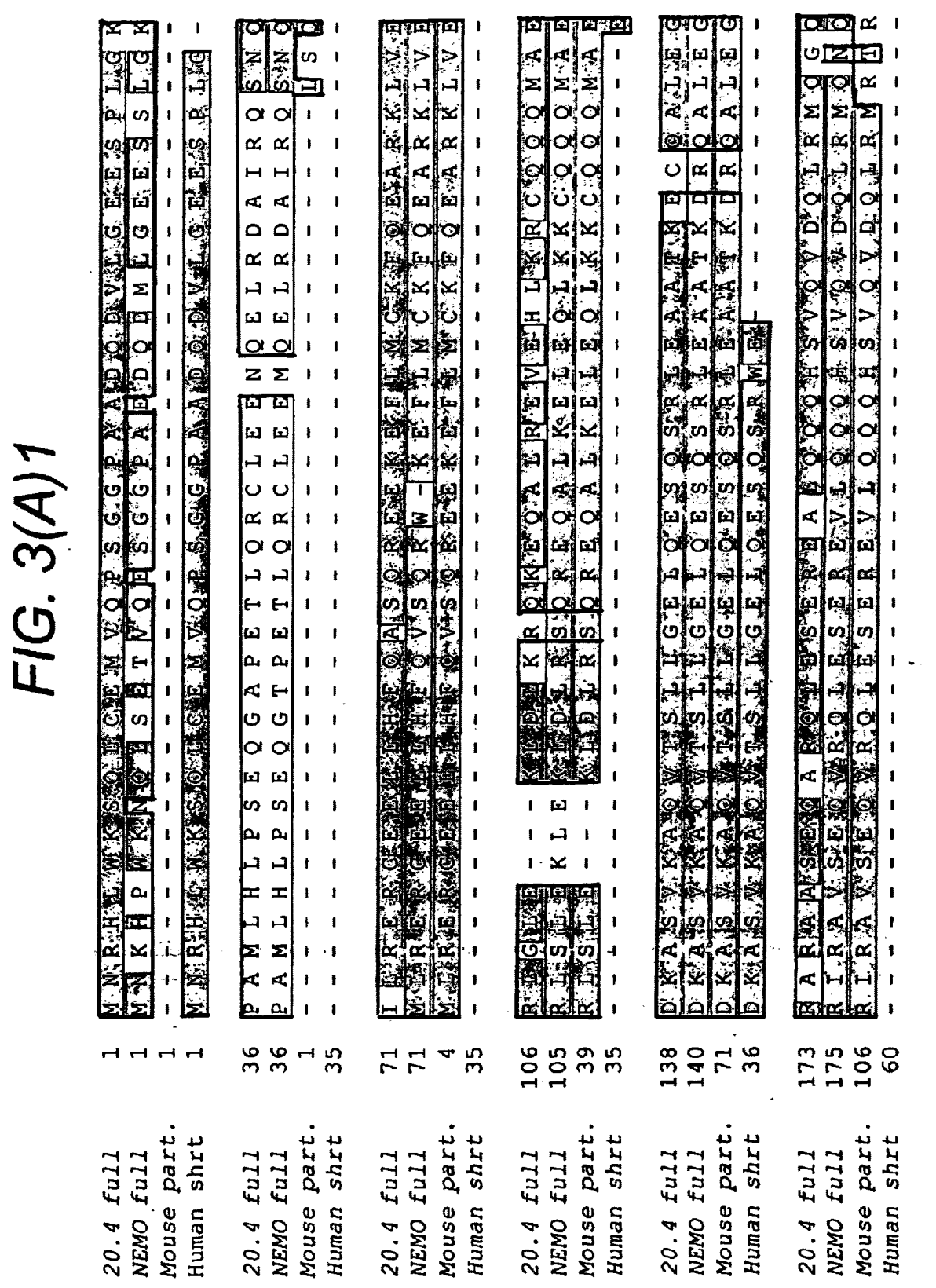
Figure 3B:
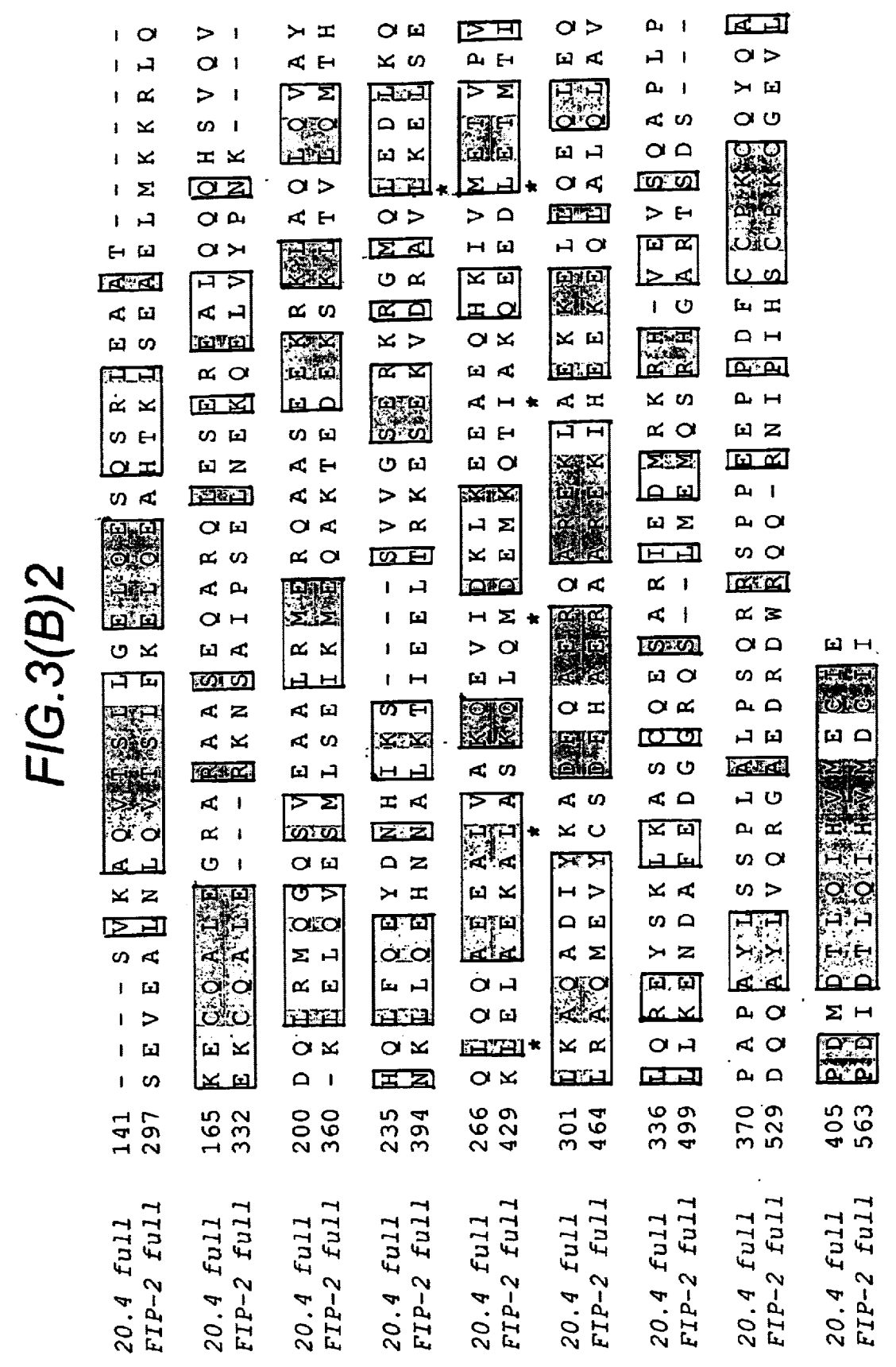

This clone, as noted above, was used to screen a phage cDNA library and an EST databank. It can be seen from FIGS. 1 and 2 that the coding sequences of the two clones are identical, while the 5'-non coding regions differ. Thus we are probably concerned with alternatively spliced forms. The clones are of about 2.0 Kb with an ORF (open reading frame) of about 1.5 Kb, which account for a molecular weight of about 50 Kd for the protein itself. The deduced amino acid sequence of RAP-2 is shown in FIG. 3.

Analysis of the above sequences of the RAP-2 clone and sequences in the 'dbest' database, Human Genome Database level 1 and GenBank database revealed that the RAP-2 sequence was a unique (novel) sequence as no known sequence showed any significant homology to this RAP-2 sequence. After filing of IL 123758, from which this application claims priority, Yamaoka S. et al. (1998), reported the characterization of a murine cDNA encoding a 48 kD protein, which was designated NEMO (for NF-κB Essential Modulator). (See background)

Additional database (in silico) searches identified FIP-2—a protein with unknown functions originally cloned, by Li Y. et al. (1998, see background).

As can be seen from the global alignment of the RAP-2 and the FIP-2 sequences (FIG. 3B), the degree of overall similarity is fairly low (it is therefore not surprising the sequence was not identified using scans based on global algorithms). The homology between RAP-2 and FIP-2 increases towards the C-terminus of the proteins, culminating in virtual identity of the C-terminal 30 amino acids. Noteworthy, beside the latter region, the putative LZ-motif in FIP-2 is largely preserved in RAP-2 (except for an Ile/Ala substitution).

An additional shorter RAP-2 cDNA of approximately 0.5 kb was also identified (ID: 1469996) and which will be designated hereafter Human shrt. This variant comprised coding sequence "blocks" deriving from several remote regions of the 1.5 kb "full" cDNA, probably derived from alternative splicing of the same gene.

Figure 4A:
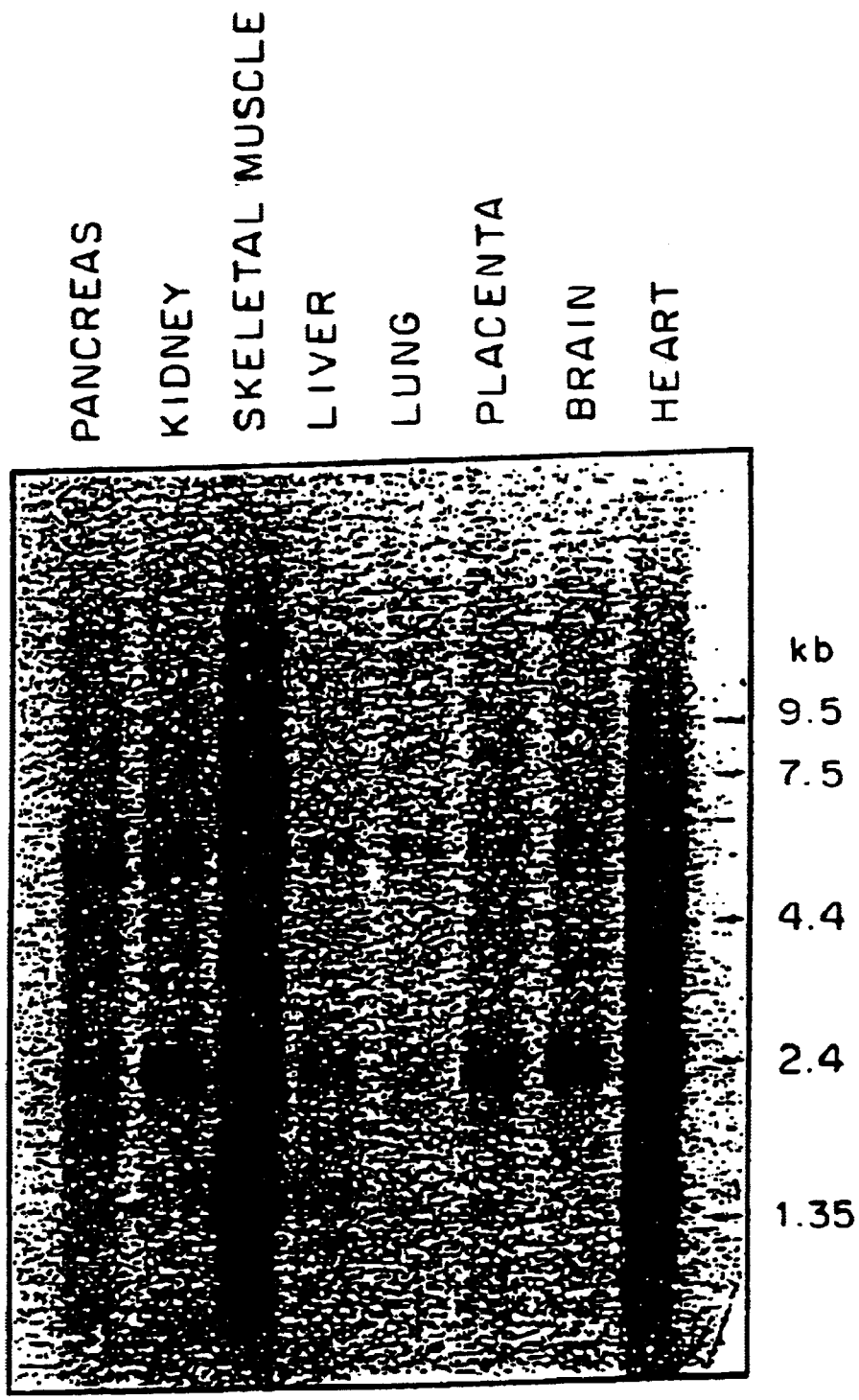
FIG. 4 describes the molecular characterization of RAP-2. In A Northern blot hybridization of Human MTN Blot I (Clontech) with a DNA fragment of RAP-2. In B RAP-2 binding to RIP is analysed as detailed in Example 3. In C NIK-RAP-2 interaction was detected as in (B), except that anti-FLAG antibodies were used for Western blotting followed by immunoprecipitation with anti-His6. An arrow marks the position of the immunoprecipitated proteins.

Northern hybridization analysis of a Multiple Tissue Northern blot (Clontech) with a 0.9 kb BgIII-fragment of RAP-2 cDNA, exposed a complex pattern of RAP-2 mRNA. At least 5 different mRNAs, ranging in size from <1 kb up to >7 kb, were detected with more or less ubiquitous prevalence of the 2.5 kb and 6 kb variants (FIG. 4A).

EXAMPLE 2

Identification of the Murine RAP-2

A similar search of the mouse ESTs collection established at TIGR revealed a partial cDNA of 1.6 kb (Mouse part. ID:76101 1, FIG. 3) probably corresponding to the mouse RAP-2, since it is virtually identical (95%) to its human counterpart throughout the coding region (see FIG. 3).

Nevertheless the differences between the human and murine RAP-2 and NEMO sequences extends beyond what can be unequivocally attributed to a regular inter-species difference. In fact, a missing block of 7 amino acid (position 249 in 20.4) from murine RAP-2 and from the NEMO sequence and the insertion of 3 amino acids (KLE at position 111) in the NEMO open reading frame as compared to the full-length human variant and to the partial murine sequence are only the most noticeable examples. (FIG. 3). These however could result in functional repercussions on the activity of the protein. The functional properties reported for NEMO in fact, appeared to be the opposite of those found for human RAP-2, although the fractionation analysis reported for NEMO confirms that it localizes to the signalsome.

EXAMPLE 3

RIP Binding to RAP-2 in Mammalian Cells

Figure 4B:
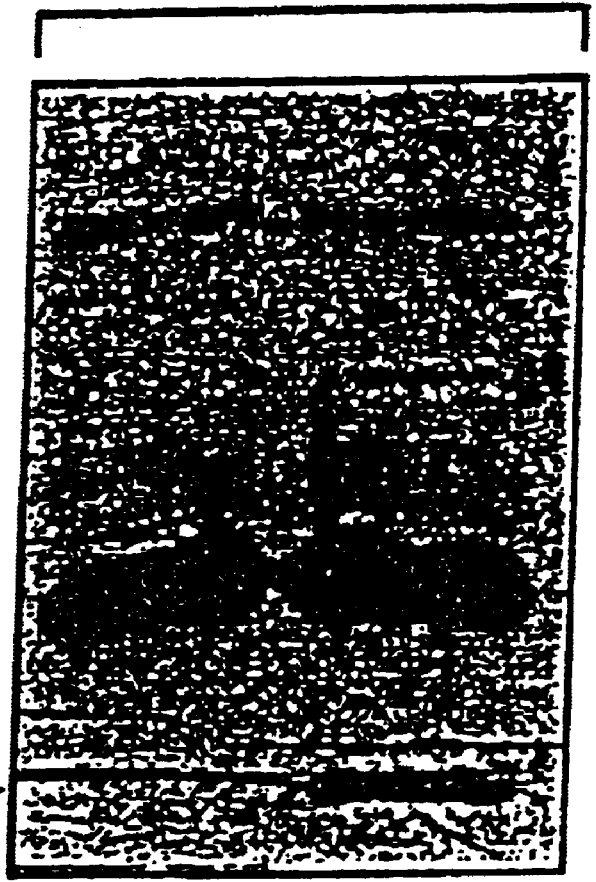

Further proof of the physiological relevance of the RAP-2-RIP interaction was obtained in transfected HEK-293T and HeLa cells. Indeed, these two proteins could be easily co-precipitated from cellular lysates of HEK-293 (ATCC No. CRL 1573) cells transfected as indicated below each lane in FIG. 4B and immunoprecipitated with anti-FLAG mAbs (Kodak). Immunocomplexes were then analysed for the presence of HIS-RAP-2 by conventional Westen blot procedure with anti-His6 mAbs (Sigma) (FIG. 4B and data not shown). However, formation of such a complex did not result in RIP enzymatic activity: to the extent we could judge by an in vitro immunocomplex kinase assay, over-expressed RIP did not phosphorylate RAP-2 (not shown).

Binding assay tests were performed to determine whether RAP-2 binds to any of the other known intracellular signaling proteins. In these tests the proteins TRADD, MORT-1, p55-R, p75-R, MACH were tested for their ability to bind to RAP-2. However, it was found that RAP-2 was incapable of binding to any of these proteins. RAP-2 also did not bind to any of the control proteins, e.g. lamin, cyclin D.

All of the above results therefore indicate that the new RAP-2 protein possibly interacts with RIP in a very specific manner and as such it represents a specific modulator/mediator of RIP.

EXAMPLE 4

Figure 4C:
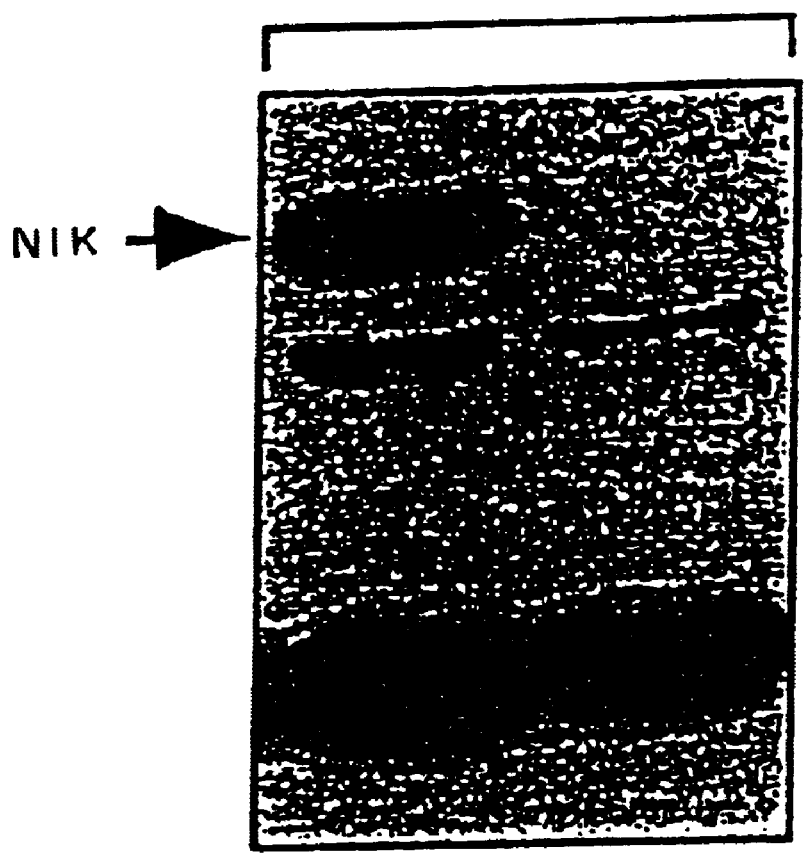
Figure 5A:
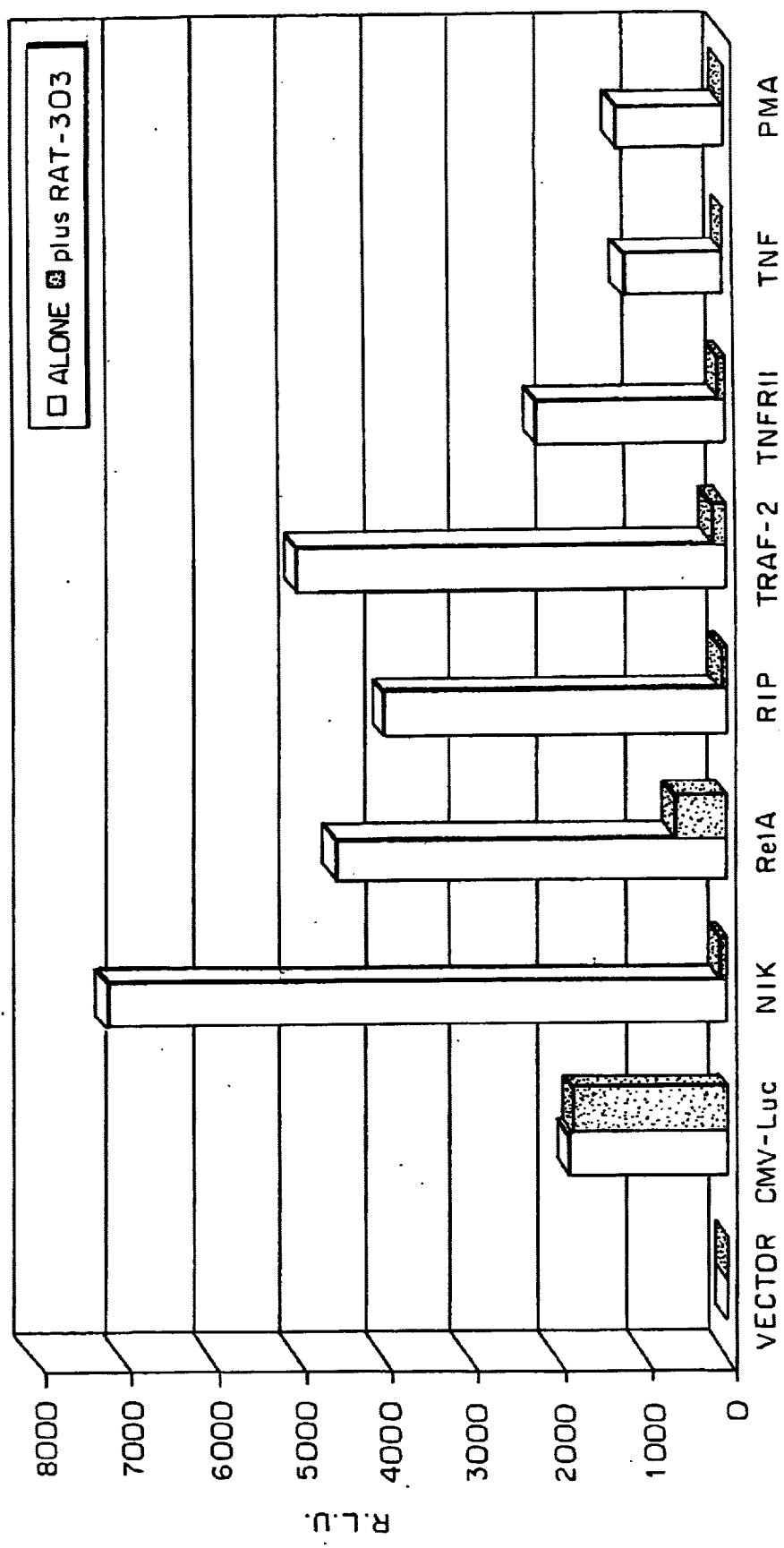
FIG. 5 is a graphic representation of the massive down-regulation of NF-κB and c-Jun activation by various stimuli, by ectopic expression of RAP-2 as described in Example 4. HEK-293T cells were transiently transfected with the reporter plasmid (HIVLTR-Luc or CMV-Luc for NF-κB(A) and GAL4-Luc for c-Jun (B) activation assays), and with an expression vector for the indicated inducer and either the empty vehicle (pcDNA3—marked alone in the figure) or a plasmid encoding the full-length RAP-2 (pcRAP-2—marked plus in the figure). Activation of the reporter gene luciferase activity is expressed in Relative Luciferase Units (R.L.U.).
Figure 5B:
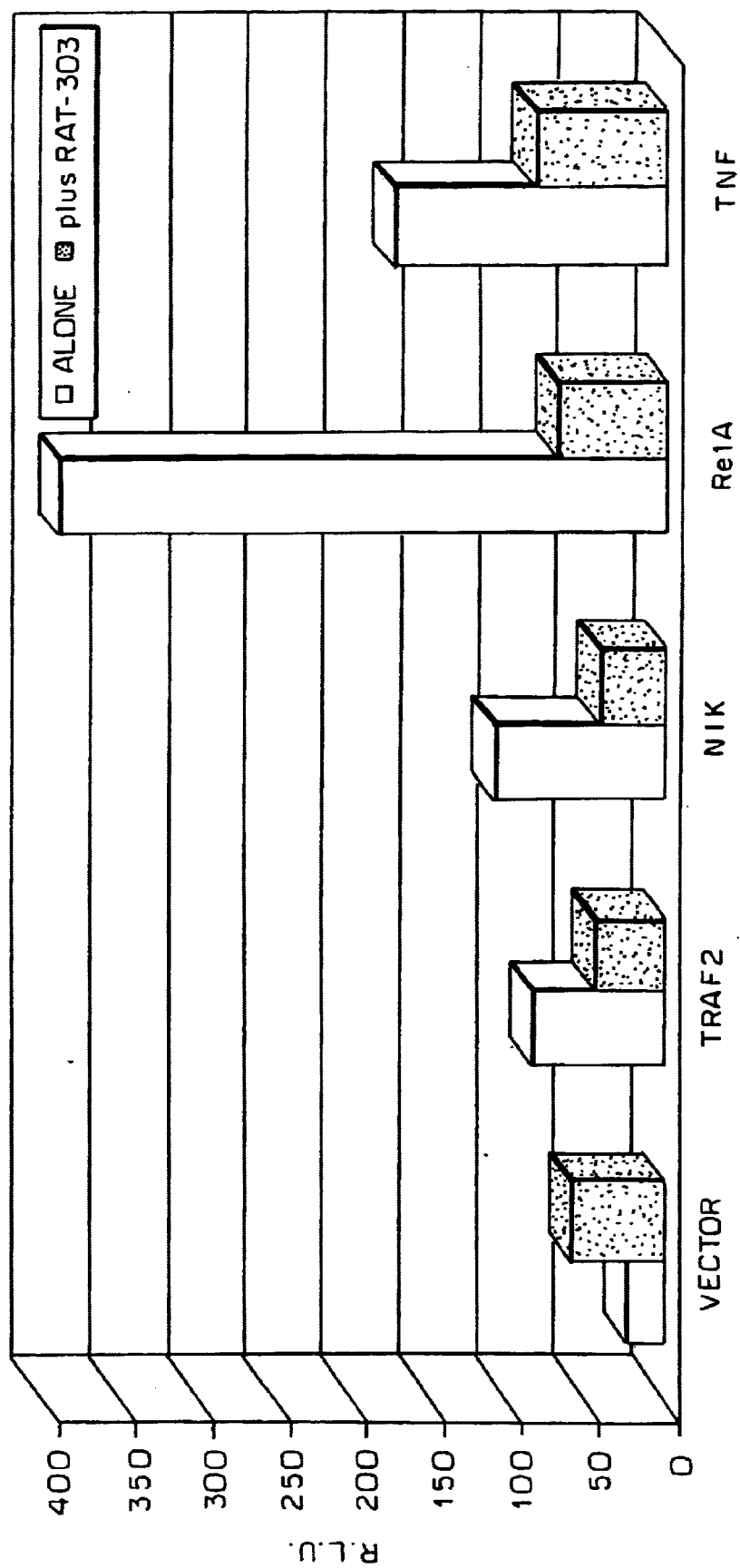

RAP-2 Interacts with NIK and Modulates the NF-κB and c-Jun-dependent Transcription Although no RAP-2-NIK interaction was detected in the two-hybrid tests in yeast (see above) transfection experiments of HEK-293T mammalian cells indicated stable formation of this complex. NIK-RAP-2 interaction was detected as described in Example 3 except that anti-FLAG antibodies were used for Western followed by immunoprecipitation with anti-His6 (FIG. 4C). Such discrepancy between binding in yeast and in mammalian cells was not surprising, since full-length NIK tends to loose its binding properties when expressed in yeast.

In view of the fact that in vivo both RIP and NIK are believed to be indispensable mediators of TNTF-induced NF-κB activation, we examined whether overexpression of RAP-2 in cell culture is capable of interfering with this particular signaling pathway. An initial set of experiments was carried out in HEK-293T cells transiently transfected with reporter plasmids comprised of the luciferase gene under control of the HIV-LTR minimal promoter. In a similar setup, RAP-2 was initially found to downregulate, almost back to the basal level, reporter activation caused by both over-expression of various known NF-κB-inducers involved in TNF signaling (NIK, TRAF2, RIP, etc.) and treatement of the cells by external stimuli (TNF and PMA, FIG. 5A). HEK-293T cells were transiently transfected with the reporter plasmid (HIVLTR-Luc or CMV-Luc for NF-κB (5A) and GAL4-Luc for c-Jun (5B) activation assays), and with an expression vector for the indicated inducer and either the empty vehicle (pcDNA3) or a plasmid encoding the full-length RAP-2 (pcRAP-2). Remarkably, the fact that RAP-2 is able to exert its effects as far down the signal transduction pathway as RelA, implies that part of this protein action could be common to various, and otherwise divergent, signaling pathways (see below). At the same time, κB-independent (CMV early promoter-driven) transcription of luciferase was not compromised (FIG. 5A), and we thus believe that possible generic disarrangement of the basal transcription/translation machinery by RAP-2 can be ruled out. These results were subsequently, fully confirmed in HeLa cells (not shown).

However, as further titration assays revealed, the actual phenomenon was far more complex. In fact, when TRAF2 was transiently expressed in HEK-293T cells along with the various amounts of pcRAP-2 indicated in FIG. 6, RAP-2 drastically changed its behavior at low concentrations (around 20 ng/$10^6$ cells), enhancing TRAF2 NF-κB induced transcription (see FIG. 6A). Moreover, by replacing the original insert with one in the reverse orientiation, an effective RAP-2 antisense-expressing vehicle was designed and TRAF2 was transiently expressed in HEK-293T cells along with the various indicated amounts of pcRAP-2-a/s (antisense) constructs, and the effect of progressive depletion of RAP-2 was analysed, leading to the outlining of a concentration-related diagram. The overall trend of the plot indicates that cell responsiveness is roughly inversely correlated to the amount of transfected RAP-2 DNA, except for a characteristic region which befalls about a 'zero'-point corresponding to the nominal endogenous level of the protein (FIG. 6). It should be noted that down-regulating the expression of a given gene by introduction of an antisense is presumably more refined, as opposed to a sense over-expression. An antisense in fact does not involve artificial production of any foreign protein within the cell, and therefore, clearly underscores the validity of the RAP-2 inhibitory capacity. Nevertheless, it should be noted that the above-mentioned leap at low concentrations is mirrored, not inversed, into the antisense half of the chart (FIG. 6).

To assess the diversity of transcriptional systems in which RAP-2 could be involved, we shifted to the study of c-Jun, a nuclear factor whose role in establishing and maintaining an adequate stress-response is proven to be almost as crucial as that of NF-κB. Using components of the commercial 'Path Detect' system (Stratagene), we confirmed a similar bi-phase performance of RAP-2 in relation to several recognized activators of AP-1 in HEK-293T and HeLa cells (see FIGS. 5B & 6B).

EXAMPLE 5

RAP-2 Potentiates c-Jun Hyper-phosphorylation, Without Altering JNK Activity To study the mechanism underlying such a profound effect on transcription, it was essential to determine the precise level at which normal signaling crumbles. It is acknowledged that the trans-activation potential of c-Jun is regulated by extracellular signal-induced phosphorylation of two serine residues ($^{63}$Ser & $^{73}$Ser) of its amino-terminal activation domain. The JNK/SAPK protein kinases responsible for the abovementioned phosphorylation constitute a fairly distant subset of the MAP kinase family and are themselves activated via phosphorylation at $^{183}$Thr and $^{185}$Tyr mediated by further upstream dual-specificity kinases. Therefore, phosphorylation status of the appropriate sites within both c-Jun and JNKs can be used as a marker reflecting the activation state of the protein. Western blot analysis with lysates of transiently transfected HEK-293T cells revealed that, notwithstanding impairment of c-Jun-mediated transcription, RAP-2 markedly potentiated phosphorylation of endogenous c-Jun at $^{63}$Ser induced by a number of stimuli (see FIG. 7A). Total cellular lysates of HEK-293T cells, transfected with the indicated expression constructs together with either pcDNA3-carrier denoted in FIG. 7 by a minus sign (−) or with pcRAP-2 denoted in the same figure by a plus sign (+), were resolved on SDS-PAGE, transferred onto the ECL-membrane and probed with anti-phospho-$^{63}$Ser-c-Jun Abs (NEB). The membrane shown on the lower panel of FIG. 7A was re-probed with anti-total-c-Jun Abs as control (NEB).

The total amount of c-Jun however, remained unchanged excluding elevation of c-Jun levels as a possible source of modification. Antibodies specific to the phosphorylated form of JNK1/2, did not detect any substantial increase in amount of these activated kinases in response to RAP-2 over-expression indicating that the additional phosphorylation of c-Jun did not result from a RAP-2-dependent boost of JNKs activity (FIG. 7B). Activated JNK1/2 from HEK-293T cells transfected with either pcDNA3 or pcRAP-2, treated with hrTNFα for increasing periods of time were detected by Western blotting of total lysates with phospho-($^{183}$Thr/$^{185}$Tyr)-JNK Abs (NEB) as shown in FIG. 7.

In further support of the latter notion, in vitro kinase assay with immunoprecipitated JNK1 and purified GST-c-Jun as a substrate produced essentially the same result (FIG. 7C). HEK-293T cells, were co-transfected with empty vector, pcRAP-2 and pcRIP in various combinations together with HA-JNK1-expressing plasmid. JNK1 was then immunopre-cipitated via its N-terminal HA-tag and its ability to phos-phorylate bacterially-produced purified GST-Jun was deter-mined by $^{32}$P-incorporation in an in vitro kinase assay. Reaction products were analyzed by SDS-PAGE as shown in FIG. 7.

RAP-2 becomes phosphorylated when RAP-2-IKK1 complex, immunoprecipitated from transfected HEK293 cells, is incubated under in vitro phosphorylation conditions. A search for the functional role of the phosphorylation of RAP-2 revealed that mutation of one particular serine in this protein (in position 148) fully abolishes the activation of Jun phosphorylation by it. As illustrated in FIG. 13, while overexpression of the wild type RAP-2 resulted in a massive increase in Jun phosphosylation, overexpression of RAP2 (S148A) did not affect at all the phosphorylation of Jun. The effect of RAP2 on NF-κB, however, was not affected at all by this mutation. These findings indicate that phosphoryla-tion of serine 148 in RAP2 is specifically involved in its effect on Jun phosphorylation.

EXAMPLE 6

RAP-2 Does not Inhibit c-Jun and RelA Binding to DNA

In view of the fact that the experiments reported in Example 5 did not reveal the cytosolic modulating target of RAP-2 over-expression of NF-κB- and AP-1-signaling cascades, we investigated the integrity of the nuclear pro-cesses required for transcription. Electro mobility shift assay (EMSA) performed with nuclear extract of transfected HEK-293T cells unequivocally demonstrated that RAP-2 did not interfere with binding of c-Jun and RelA to the oligonucleotides corresponding to their classical recognition sequences (FIG. 8). In fact, a several-fold enhancement in efficiency of the DNA/AP-1 complex formation in RAP-2-transfected cells was observed. Furthermore, no interaction was observed between RAP-2 and c-Jun/RelA that could result in sterical obstruction of activation domains of the latter. It is suggested that, if any, the effect of the entrance of RAP-2 into nucleus is targeted at some point downstream of the enhancer-binding events.

EXAMPLE 7

RAP-2 Interacts In-vivo with Histone Acetyltransferase TIP60

TIP60 (GeneBank U 74667) belongs to the recently described family of nuclear proteins called histone acetyl-transferases (HATs). The enzymatic activity of these pro-teins is associated with the state of chromatin structure in nucleosomal complexes. HATs are frequently associated with certain elements of the transcriptional apparatus and are capable of modulating the rate of transcription. HATs act by relaxing a chromatin package in the vicinity of initiation sites by means of transferring acetyl groups onto specific lysine residues of histones, thereby promoting access of various related factors to DNA. It is apparently one of those auxiliary nuclear proteins, meant to facilitate cross talk between the enhancer-binding factors and RNA polymerase II. We thus investigated whether TIP60 could complex with RAP-2. Immunoprecipitation from HeLa cells followed by two-hybrid tests conclusively showed that RAP-2 strongly interacts with TIP60 in both systems. Nevertheless, we were not able to see any considerable alteration of RAP-2-mediated effect on NF-κB and c-Jun upon co-expression of TIP60 in HEK-293T cells (not shown). The same lack of changes was observed in the control experiment, i.e. stimulation±TIP60 (w/o RAP-2), leading to the conclusion that the short time readout (20–30hrs after transfection), probably precludes the chances of the reporter DNA to become chromatinized, leaving no sufficient time for HAT-like enzymes to perform.

EXAMPLE 8

Clone#10—a Novel Proteins Interacting with RAP-2

Applying the full-length RAP-2 protein as bait in two-hybrid screen of a B-cell cDNA library, we have isolated a novel protein interacting with RAP-2 denoted hereafter clone #10 or clone #10-encoded protein or RAT-binding protein #10 or RBP-10 (FIG. 10). The original clone (about 2.2 kb) was found to encode a putative polypeptide of apparent MW of 60 kDa. However, the putative ATG first codon is apparently missing from this sequence. Despite its considerable length, the obtained cDNA has therefore to be expanded further towards the 5' end to reconstitute the entire open reading frame.

Two-hybrid assay of the binding repertoire of clone #10 revealed that this protein, besides RAP-2, has rather strong affinity for TRAF2. Clone #10 however does not bind to RIP, TRADD, MORT1, MACH, TNFR-1, TIP60 and NIK as well as to several control proteins (for example lamin and cyclin). It cannot, however, be excluded that binding of clone#10 to NIK might be found in mammalian cells, considering the peculiarities of NIK's behaviour in yeast. Clone #10 was shown to bind RAP-2 within the C-terminal 200 a.a. of the latter. i.e. a region not necessarily associated with the binding of RIP, TIP60, NIK and IKKβ.

Coexpression of Clone #10 with TRAF-2 in mammalian 293T cells prevented TRAF2-mediated activation of NF-κB, whereas coexpression of clone #10 with NIK strongly elevated NF-κB activation by the latter. These findings could indicate an important regulatory function of clone #10. The distinct modulating effects observed could probably imply existance of different, non-overlapping sites of the protein action within a cell.

Several rounds of GenBank searches aiming at identifi-cation of close RBP-10-homologues led to the identification of F40F12.5 (accession number S42834)—a hypotetical protein from C.Elegans, to which no physiological role was assigned. Interestingly, F40F2.5 was found to display some similarity to several members of the widely conserved family of ubiquitin-directed proteases. These enzymes counterbalance the destructive effect of the ubiquitination machinery, which is known to be in charge of the majority of protein degradation events in a cell. While ubiquitin ligases are responsible for attaching the poly-ubiquitin tree to a protein predestined for degradation, ubiquitin proteases prevents an effective branching of the growing tree. Such presumption regarding the function of F40F12.5 based on the similarity to the abovementioned ubiquitin-directed proteases however appears to be questionable as it has not yet been examined whether this particular protein posesses any enzymatic activity toward ubiquitin polymers. Furthermore a couple of points appear to make such a coincidence quite unlikely:

- a) Residues which are believed to constitute the core catalitic region in either subclasses of ubiquitin proteases are not conserved neither in F40F12.5, nor in RBP-10;
- b) Except from their catalytic sites, enzymes of the ubiquitin-directed protease family derived from various species (from bacteria to human) display virtually no sequence similarity while F40F12.5 and clone #10 dispaly a certain degree of homology.

EXAMPLE 9

Clone #84: a RAP-2 Interacting Protein

An additional RAP-2 binding protein was identified by applying the full-length RAP-2 protein as bait in the two-hybrid screen of the B-cell cDNA library and termed clone #84.

Clone #84 was found to specifically bind to the full length RAP-2 while displaying no interaction with any other protein analyzed including TRAF2, MORT1, TRADD, RIP, NIK, TIP60 and Lamin. The partial 5'-sequence of clone #84 was found to be identical to the sequence of a previously cloned cDNA encoding the Cell Growth Regulatory protein CGR19, identified as a transcript up-regulated specifically in cells harboring functional p53 protein (Madden S. et al. 1996, accession # U66469). Sequence analysis of CGR19 led to the identification of a $C_3HC_4$-Zink Finger motif (also referred to as a RING finger) at its C terminal domain. Expression of CGR19 was found to supress growth of several cell lines. The involvement of CGR19 protein in NF-κB regulation by means of binding to RAP-2 could possibly indicate modulation of the cell cycle regulatory network by members of the TNF-R family.

EXAMPLE 10

Structure-functional Relationship of RAP-2

A. Binding Regions

By employing consecutive deletion analysis, the binding regions within RAP-2 were mapped and RIP, NIK, TIP60-binding as well as the self-association domain(s) were identified (FIG. 11).

Binding to RIP has been mapped to a region of the RAP-2 protein that begins between amino acids 177–218 and ends at amino acid 264.

So far neither the IKKβ nor the NIK binding sites (amino acids 95–264) and (amino acids 1–264) respectively were found to overlap RIP's binding site within RAP-2 (FIG. 11).

Binding to TIP60 apparently maps within the region spanning amino acids 95–264. The lack of interaction with the deletion fragment spanning amino acids 95–309, could most likely be the result of a specific obstructive conformation pertaining to this particular deletion.

A similar discrepancy in binding to the deletion fragments can be noted for binding of clone #10 and for self-association of RAP-2. As opposed to TIP60, however, the fact that full-length RAP-2 binds to the deletion fragment containing amino acids 218–416 as well as to the deletion fragment containing amino acids 1–264, implies that the region involved in homo-dimerization localizes in between amino acids 217–264.

The protein encoded by clone #10, with the above-mentioned exception, apparently binds within a region beginning between amino acids 218–309 and ending at amino acid 416 and thus, its binding site may comprise overlaping regions with the binding sites for RIP, d NIK, IKKβ and TIP60 (FIG. 11).

B. Functional Regions.

To the extent of our present knowledge, all the functional effects of RAP-2 (namely NF-κB inhibition and induction of c-Jun hyper-phosphorylation) map to the same region (FIG. 11).

Furthermore, it is possible that the region sufficient for effective modulation of signaling by all the inducers used in these experiments localizes to the N-terminal segment of the protein.

The region encompassed by amino acids 95–416 did have an effect, although it was significantly weaker as compared to the one caused by the full-length protein and, thus, may result from enforced aggregation of the endogenous RAP-2.

Figure 12B:
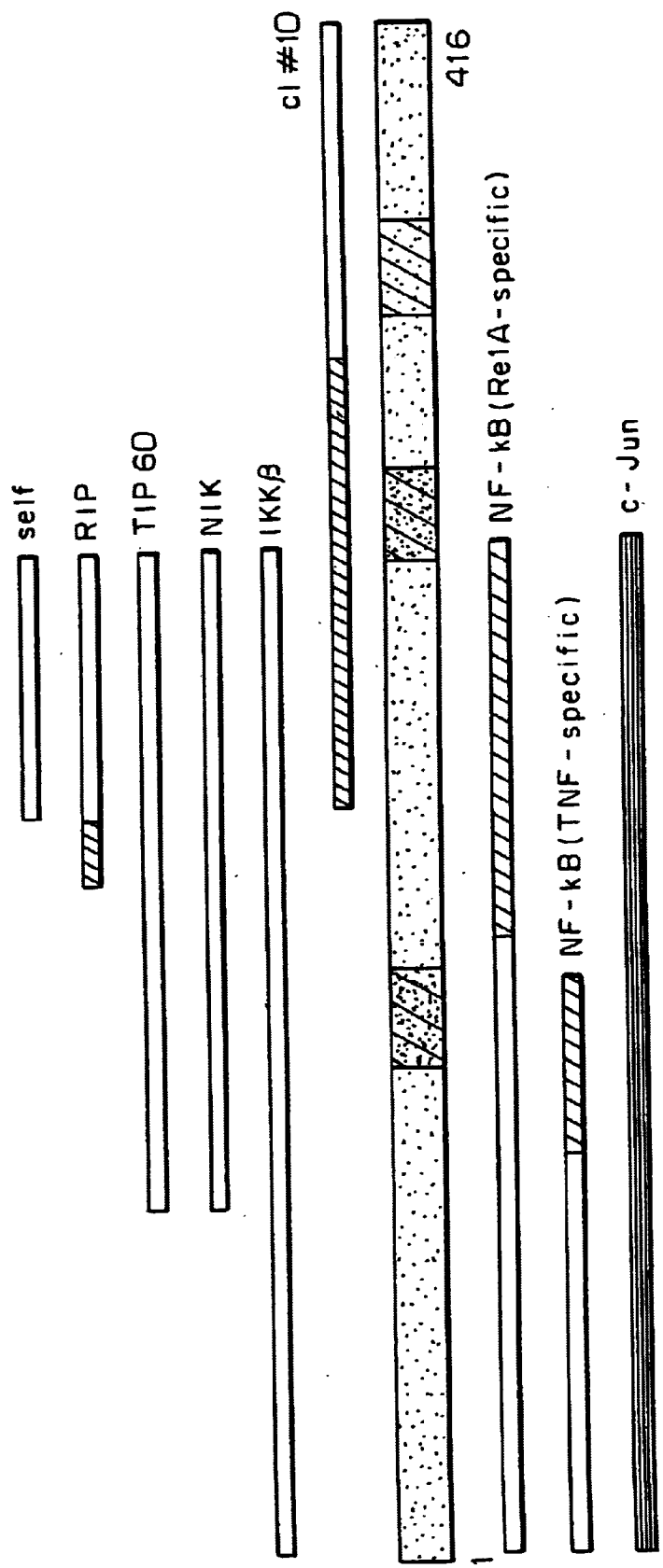

Moreover, with the exception of RelA, the effect of all inducers used in our experiments can be mediated by as few as approximately 100 N-terminal amino acids of RAP-2. In fact even the fragment encompassing amino acids 1–102 mediates a distinct effect, albeit fairly moderate (FIG. 12B).

On the other hand, successful induction of RelA requires a much longer portion of the RAP-2 protein. So far we could define the boundaries of this region to be in-between amino acids 1 to 264, which apparently endows the region between amino acids 157 and 264 with some specific, RelA-associated, binding properties.

C. Binding-function Relationship

From the results shown in FIGS. 11 and 12, it appears that:

a) With the exception of RelA, RAP-2 binding to RIP, clone #10 and, most likely, to NIK and TIP60 are not required for the function of the protein, as inhibitor of overexpression induced NF-κB.

b) The effect of RAP-2 on RelA over-expression-induced activation is obviously mediated, at least partly, by different binding events. Essentially, all of the above-mentioned proteins may be found to contribute to the given activity, as deduced from the experiments carried out to date.

The exact site of interaction between RAP-2 and RIP is yet to be determined but it seems that this site is one specific to RIP and RAP-2 and not shared by other proteins known to interact with RIP, e.g. MORT-1, TRADD, FAS-R and possibly also TRAF2 (see Malinin et al., 1997). It also arises that (from sequence analysis and comparison with sequences in various databases as noted above) that RAP-2 does not have a 'death domain', a MORT MODULE, a protease domain (e.g. ICE/CED3 motif), a kinase domain/motif nor TRAF domains. In line with this, biological activity analysis also revealed that RAP-2 apparently has the following characteristics:

(i) when overexpressed, RAP-2 strongly inhibits NF-κB activation by TNF or by overexpression of TRADD, RIP, TRAF-2, NIK or p65 NF-κB subunit;

(ii) RAP-2 potentiates c-Jun hyper-phosphorylation, without altering JNK activity.

(iii) RAP-2, as shown by deletion analysis, does not require the death domain of RIP, nor the kinase activity of RIP for binding to RIP;

(iv) based on the above deletion analysis, the binding region of RAP-2 to RIP was narrowed down to an N-terminal region of about 200 amino acids;

(v) RAP-2 binds to NIK in transfected mammalian cells, but not in yeast.

In view of the aforementioned RAP-2 therefore appears to be a highly specific RIP-binding protein and hence RIP modulator/mediator, that is likely to be involved in the RIP-mediated intracellular signaling pathways.

In light of the above it appears that RAP-2 is involved in modulation/mediation of RIP's activities. Intracellularly, these being RIP's involvement in the cell survival pathway (NF-κB activation, possibly via interaction with TRAF2) and its involvement in the inflammation and cell death pathway (independently via its 'death domain' or via interaction with other proteins such as MORT-1, TRADD, p55-R, FAS-R and associated proteases such as MACH, Mch4, G1 and the like). The possible ways in which RAP-2 may modulate/mediate RIP's activity are detailed hereinabove. For example the RAP-2-RIP interaction may lead to enhancement of either the cell death or cell survival pathways, or it may lead to the inhibition of either the cell death or cell survival pathways, this enhancement or inhibition possibly being dependent on the relative activities of other members of these two opposing intracellular pathways. RAP-2 may also act as a docking protein to provide for an aggregation of a number of RIP molecules and other RIP- or RAP-2- binding proteins, which aggregate may then function either in the direction of cell death or cell survival (or even both) depending on the relative activities/amounts of the other members of these pathways in the cell.

EXAMPLE 11

Preparation of Polyclonal Antibodies to RAP-2

Rabbits are initially injected subcutaneously with 5 μg of a pure preparation of RAP-2 emulsified in complete Freund's adjuvant. Three weeks later, they are injected again subcutaneously with 5 μg of the RAP-2 preparation in incomplete Freund's adjuvant. Two additional injections of RAP-2 as solution in PBS are given at 10 day intervals. The rabbits are bled 10 days after the last immunization. The development of antibody level is followed by radioimmuniassay. $^{125}$I-labeled RAP-2 is mixed with various dilutions (1:50, 1:500, 1:5,000 and 1:50,000) of the rabbit serum. A suspension of protein-G agarose beads (20 μl, Pharmacia) is added in a total volume of 200 μl. The mixture is left for 1 hour at room temperature, the beads are then washed 3 times and bound radioactivity is counted. Rabbit antiserum to human leptin is used as a negative control. The titer of the RAP-2 antiserum is measured as compared to that of the negative control.

EXAMPLE 12

Preparation of Monoclonal Antibodies to RAP-2

Female Balb/C mice (3 months old) are first injected with 2 μg purified RAP-2 in an emulsion of complete Freund's adjuvant, and three weeks later, subcutaneously in incomplete Freund's adjuvant. Three additional injections are given at 10 day intervals, subcutaneously in PBS. Final boosts are given intraperitoneally 4 and 3 days before the fusion to the mouse showing the highest binding titer as determined by IRIA (see below). Fusion is performed using NSO/1 myeloma cell line and lymphocytes prepared from both the spleen and lymph nodes of the animal as fusion partners. The fused cells are distributed into microculture plates and the hybridomas are selected in DMEM supplemented with HAT and 15% horse serum. Hybridomas that are found to produce antibodies to RAP-2 are subcloned by the limiting dilution method and injected into Balb/C mice that had been primed with pristane for the production of ascites. The isotypes of the antibodies are defined with the use of a commercially available ELISA kit (Amersham, UK).

The screening of hybridomas producing anti-RAP-2 monoclonal antibodies is performed as follows: Hybridoma supernatants are tested for the presence of anti-RAP-2 antibodies by an inverted solid phase radioimmunoassay (IRIA). ELISA plates (Dynatech Laboratories, Alexandria, Va.) are coated with Talon-purified IL-18BPa-His$_6$ (10 μg/ml, 100 μl/well). Following overnight incubation at 4° C., the plates are washed twice with PBS containing BSA (0.5%) and Tween 20 (0.05%) and blocked in washing solution for at least 2 hrs at 37° C. Hybridoma culture supernatants (100 μl/well) are added and the plates are incubated for 4 hrs at 37° C. The plates are washed 3 times and a conjugate of goat-anti-mouse horseradish peroxidase (HRP, Jackson Labs, 1:10,000, 100 μl/well) is added for 2 hrs at room temperature. The plates are washed 4 times and the color is developed by ABTS (2,2'-azino-bis (3-ethylbenzthiazoline-6-sulfonic acid, Sigma) with $H_2O_2$ as a substrate. The plates are read by an automatic ELISA reader. Samples giving OD that are at least 5 times higher than the negative control value are considered positive.

The RAP-2 antibodies can be employed for purification of RAP-2 by affinity chromatography.

EXAMPLE 13

ELISA Test

Microtiter plates (Dynatech or Maxisorb, by Nunc) are coated with anti-RAP-2 monoclonal antibody (serum free hybridoma supernatant or ascitic fluid immunoglobulins) overnight at 4° C. The plates are washed with PBS containing BSA (0.5%) and Tween 20 (0.05%) and blocked in the same solution for at least 2 hrs at 37° C. The tested samples are diluted in the blocking solution and added to the wells (100 μl/well) for 4 hrs at 37° C. The plates are then washed 3 times with PBS containing Tween 20 (0.05%) followed by the addition of rabbit anti-RAP-2 serum (1:1000, 100 μl/well) for further incubation overnight at 4° C. The plates are washed 3 times and a conjugate of goat-anti-rabbit horseradish peroxidase (HRP, Jackson Labs, 1:10,000, 100 μl/well) was added for 2 hrs at room temperature. The plates were washed 4 times and the color is developed by ABTS (2,2'-azino-bis (3-ethylbenzthiazoline-6-sulfonic acid, Sigma) with $H_2O_2$ as a substrate. The plates are read by an automatic ELISA reader.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Alnemri, E. S. et al. (1995) J. Biol. Chem. 270:4312–4317.
Barinaga, M. (1 993) Science 262:1512–1514.
Beg, A. A. and Baltimore, D. Science 274:782–784.
Beidler, J. et al., (1995) J. Biol. Chem. 270:16526–16528.
Berger, J. et al., (1988) Gene 66:1–10.
Beutler, B. and Cerami, C. (1987) NEJM: 316:379–385.
Bigda, J. et al. (1994) J. Exp. Med. 180:445–460.
Boldin, M. P. et al. (1995a) J. Biol. Chem. 270:337–341.
Boldin, M. P. et al. (1995b) J. Biol. Chem. 270:7795–7798.
Boldin, M. P. et al. (1996) Cell 85:803–815.
Brakebusch, C. et al. (1992) EMBO J., 11:943–950.
Brockhaus, M. et al. (1990) Proc. Natl. Acad. Sci. USA, 87:3127–3131.
Cantor, G. H. et al. (1993) Proc. Natl. Acad. Sci. USA 90:10932–6.
Cerreti, D. P. et al. (1992) Science 256:97–100.
Chen, C. J. et al. (1992) Ann. N.Y. Acad. Sci. 660:271–3.
Chinnaiyan et al. (1995) Cell 81:505–512.
Chinnaiyan et al. (1996) J. Biol. Chem. 271:4961–4965.
Cifone, M. G. et al. (1995) EMBO J. 14:5859–5868.
Clement, M. V. et al. (1994) J. Exp. Med. 180:557–567.
Crisell, P. et al., (1993) Nucleic Acids Res. (England) 21 (22):5251–5.
Current Protocols in Molecular Biology (Ausubel, F. M., Brent, R., Kingston, R. E., Moore, D. D., Seidman., J. G., Smith, J. A., Struhl, K., Albright, L. M., Coen, D. M. & Varki, A., eds.), (1994) pp. 8.1.1–8.1.6 and 16.7–16.7.8, Greene Publishing Associates, Inc. and Wiley & Sons, Inc., New York.
Dirks, W., et al., (1 993) Gene 128:247–249.
Durfee, T. et al. (1993) Genes Dev. 7:555–569.
Eischen, C. M. et al. (1994) J. Immunol. 153:1947–1954.
Ellis, H. M. et al. (1986) Cell 44:817–829.
Enari, M. et al. (1995) Nature 375:78–81.
Engelmann, H. et al. (1990) J. Biol. Chem., 265:1531–1536.
Faucheu, C. et al. (1995) EMBO J. 14:1914–1922.
Fernandes-Alnemri, T. et al. (1994) J. Biol. Chem. 269:30761–30764.
Fernandes-Alnemri, T. et al. (1995) Cancer Res. 55:2737–2742.
Fernandes-Alnemri, T. et al. (1996) Proc. Natl. Acad. Sci. USA 93:7464–7469.
Field, J. et al. (1988) Mol. Cell Biol. 8:2159–2165.
Fields, S. and Song, 0. (1989) Nature, 340:245–246.
Frangioni, J. V. and Neel, B.G. (1993) Anal. Biochem. 210:179–187.
Geysen, H. M. (1985) Immunol. Today 6:364–369.
Geysen, H. M. et al. (1987) J. Immunol. Meth. 102:259–274.
Gossen, M. and Boujard, H. (1992) Proc. Natl. Acad. Sci. USA, 89:5547–5551.
Grell, M. et al. (1994) Eur. J. Immunol. 24:2563–2566.
Heller, R. A. et al. (1990) Proc. Natl. Acad. Sci. USA, 87:6151–6155.
Henkart, P. A. (1996) Immunity 4:195–201.
Hohmann, H.-P. et al. (1989) J. Biol. Chem., 264:14927–14934.
Howard, A. D. et al. (1991) J. Immunol. 147:2964–2969.
Hsu, H. et al. (1995) Cell 81:495–504.
Hsu, H. et al. (1996) Cell 84:299–308.
Itoh, N. et al. (1991) Cell 66:233.
Itoh, N. and Nagata, S. (1993) J. Biol. Chem. 268:10932–7.
Joseph, S. and Burke, J. M. (1993) J. Biol. Chem. 268:24515–8.
Kamens, J. et al. (1995) J. Biol. Chem. 270:15250–15256.
Kaufmann, S. H. (1989) Cancer Res. 49:5870–5878.
Kaufmann, S. H. (1993) Cancer Res. 53:3976–3985.
Kischkel, F. C. et al. (1995) EMBO J. 14:5579–5588.
Koizumi, M. et al. (1993) Biol. Pharm. Bull (Japan) 16 (9):879–83.
Kumar, S. et al. (1994) Genes Dev. 8:1613–1626.
Kumar, S. (1995) Trends Biochem Sci. 20:198–202.
Lazebnik, Y. A. et al. (1994) Nature 371:346–347.
Leithauser, F. et al. (1993) Lab Invest. 69:415–429.
Li. Y. et al. (1998) Mol Cell Biol 18:1601–1610
Loetscher., H. et al. (1990) Cell, 61:351–359.
Los, M. et al. (1995) Nature 375:81–83.
Madden, S. L. et al. (1996) Cancer Res 56:5384–5390.
Malinin, N. L. et al. (1997) Nature 385:540–544.
Martin, S. J. et al. (1 995) J. Biol. Chem. 270:6425–6428.
Mashima, T. et al. (1995) Biochem. Biophys. Res. Commun. 209:907–915.
Miller, B. E. et al. (1995) J. Immunol. 154:1331–1338.
Milligan, C. E. et al. (1995) Neuron 15:385–393.
Miura, M. et al. (1995) Proc. Natl. Acad. Sci. USA 92:8318–8322.
Munday, N. A. et al. (1995) J. Biol. Chem. 270:15870–15876.
Muranishi, S. et al. (1991) Pharm. Research 8:649.
Musti A M, et al. (1997) Science 1997 275:400–402
Nagata, S. and Goistein, P. (1995) Science 267, 1449–1456.
Natoli, G. et al. (1997) J. Biol. Chem. 272, 26079–26082
Nicholson, D. W. et al. (1995) Nature 376:37–43.
Nophar, Y. et al. (1990) EMBO J., 9:3269–3278.
Piquet, P. F. et al. (1987) J. Exp. Med., 166:1280–89.
Ray et al. (1992) Cell 69:597–604.
Ruggiero, V. et al. (1987) Cell Immunol. 107:317–325.
Sambrook et al. (1989) Molecular Cloning: A Laboratory Manual, Cold Spring Harbor Laboratory Press, Cold Spring Harbor, N.Y.

Schall, T. J. et al. (1990) Cell, 61:361–370.
Schlegel, et al. (1996) J. Biol. Chem. 271:1841–1844.
Schulze-Osthoff, K. et al. (1994) EMBO J. 13:4587–4596.
Shimayama, T. et al., (993) Nucleic Acids Symp. Ser. 29:177–8
Shore, S. K. et al. (1993) Oncogene 8:3183–8.
Sleath, P. R. et al. (1990) J. Biol. Chem. 265:14526–14528.
Smith, C. A. et al. (1990) Science, 248:1019–1023.
Song, H. Y. et al. (1994) J. Biol. Chem. 269:22492–22495.
Srinivasula, S. M. et al. (1996) Proc. Natl. Acad. Sci. USA 93:14486–14491.
Stanger, B. Z. et al. (1995) Cell 81:513–523.
Tartaglia, L. A. et al. (1993) Cell, 74:845–853.
Tewari, M. et al. (1995) J. Biol. Chem. 270:3255–3260.
Tewari, M. et al. (1995a) J. Biol. Chem. 270:18738–18741.
Tewari, M. et al. (1995b) Cell 81:1–20.
Thornberry, N. A. et al. (1992) Nature 356:768–774.
Thornberry, N. A. et al. (1994) Biochemistry 33:3934–3940.
Tracey, J. T. et al. (1987) Nature, 330:662–664.
Van Antwerp, D. J. et al. (1996) Science 274:787–789.
Vandenabeele, P. et al. (1995) Trends Cell Biol. 5:392–400.
Vassalli, P. (1992) Ann. Rev. Immunol. 10:411–452.
Wallach, D. (1984) J. Immunol. 132:2464–9.
Wallach, D. (1986) In: Interferon 7 (Ion Gresser, ed.), pp. 83–122, Academic Press, London.
Wallach, D. et al. (1994) Cytokine 6:556.
Wang, L. et al. (1994) Cell 78:739–750.
Wang, C.-Y et al., (1996) Science 274:784–787.
Watanabe-Fukunaga, R. et al. (1992) Nature, 356:314–317.
Watanabe, F. R. et al. (1992) J. Immunol. 148:1274–1279.
Weitzen, M. et al. (1980) J. Immunol. 125:719–724.
Wilks, A. F. et al. (1989) Proc. Natl. Acad. Sci. USA, 86: 1603–1607.
Wong et al. (1994) J. Immunol. 152:1751–1755.
Xue, D. et al. (1995) Nature 377:248–251.
Yamaoka S, et al. (1998) Cell 93: 1231–1240.
Yonehara, S. et al. (1989) J. Exp. Med. 169:1747–1756.
Yuan, J. et al. (1993) Cell 75:641–652.
Zaccharia, S. et al. (1991) Eur. J. Pharmacol. 203:353–357.
Zhao, J. J. and Pick, L. (1993) Nature (England) 365:448–51.

We claim:

1. An isolated polypeptide which is capable of binding to RIP (receptor interacting protein), which polypeptide has the amino acid sequence of:
   (a) a RAP-2 (RIP-associated protein-2) protein whose sequence is that of SEQ ID NO: 4;
   (b) a fragment of (a) which is capable of binding to RIP,
   (c) an analog of (a) which differs from the sequence of (a) by no more than ten changes in the amino acid sequence of (a), each said change being a substitution, deletion and/or insertion of a single amino acid, which analog is capable of binding to RIP, or
   (d) a derivative of (a), (b), or (c) by modification of a functional group which occurs as a side chain or an N- or C-terminal group of one or more amino acid residues thereof without changing one amino acid to another of the twenty commonly occurring natural amino acids, which derivative is capable of binding to RIP.

2. A polypeptide in accordance with claim 1, wherein the sequence of (c) is an analog which differs from the sequence of (a) by the substitution, deletion or insertion of a single amino acid residue, which analog is capable of binding to RIP.

3. A polypeptide in accordance with claim 1, which has the amino acid sequence of SEQ ID NO:4.

4. A composition comprising a polypeptide according to claim 1 and a pharmaceutically acceptable carrier.

5. A polypeptide in accordance with claim 1(b).

6. An isolated polypeptide which is capable of binding to RIP (receptor interacting protein), which polypeptide has the amino acid sequence of:
   (a) a RAP-2 (RIP-associated protein-2) protein whose sequence is that of SEQ ID NO: 4;
   (b) a fragment of (a) which is capable of binding to RIP,
   (c) an analog of (a) which differs from the sequence of (a) by no more than ten changes in the amino acid sequence of (a), each said change being a substitution, deletion and/or insertion of a single amino acid, which analog is capable of binding to RIP.

7. A composition comprising a polypeptide according to claim 6 and a pharmaceutically acceptable carrier.

8. An isolated molecule comprising a DNA sequence encoding a polypeptide in accordance with claim 6.

9. A molecule in accordance with claim 8, wherein the DNA sequence encoding said RAP-2 protein of (a) is SEQ ID NO:1.

10. A vector comprising a molecule in accordance with claim 8.

11. A vector in accordance with claim 10 capable of being expressed in a eukaryotic host cell.

12. A vector in accordance with claim 10 capable of being expressed in a prokaryotic host cell.

13. An isolated transformed host cell containing a vector in accordance with claim 10.

14. A method for producing a polypeptide which is capable of binding to RIP, comprising:
   growing transformed host cells in accordance with claim 13 under conditions suitable for the expression of an expression product;
   thereby producing a polypeptide capable of binding to RIP; and
   isolating said polypeptide capable of binding to RIP.

* * * * *